(12) United States Patent
Rexach et al.

(10) Patent No.: US 10,663,938 B2
(45) Date of Patent: May 26, 2020

(54) POWER OPERATION OF INTELLIGENT DEVICES

(71) Applicant: Kohler Co., Kohler, WI (US)

(72) Inventors: Rafael Rexach, Sheboygan, WI (US); Jessica Schroeder, Sheboygan, WI (US); Miguel Arciniega, Sheboygan, WI (US); Ashley Springer, Sheboygan, WI (US); Shi Chao Zhang, Sheboygan, WI (US); Eric Plate, Plymouth, WI (US); Marwan Estiban, Mequon, WI (US)

(73) Assignee: KOHLER CO., Kohler, WI (US)

( * ) Notice: Subject to any disclaimer, the term of this patent is extended or adjusted under 35 U.S.C. 154(b) by 7 days.

(21) Appl. No.: 16/126,949

(22) Filed: Sep. 10, 2018

(65) Prior Publication Data

US 2019/0090056 A1    Mar. 21, 2019

Related U.S. Application Data

(60) Provisional application No. 62/559,199, filed on Sep. 15, 2017.

(51) Int. Cl.
*G05B 19/042* (2006.01)
*H04R 3/00* (2006.01)
(Continued)

(52) U.S. Cl.
CPC ............ *G05B 19/042* (2013.01); *A47K 17/00* (2013.01); *C02F 1/001* (2013.01); *C02F 1/50* (2013.01);
(Continued)

(58) Field of Classification Search
CPC ........ G05B 19/042; G05B 2219/23027; G05B 2219/23462; A47K 17/00; C02F 1/001;
(Continued)

(56) References Cited

U.S. PATENT DOCUMENTS

| 4,340,800 A | 7/1982 | Ueda et al. |
|---|---|---|
| 4,563,780 A | 1/1986 | Pollack |

(Continued)

FOREIGN PATENT DOCUMENTS

| CN | 2409562 Y | 12/2000 |
|---|---|---|
| CN | 1391690 A | 1/2003 |

(Continued)

OTHER PUBLICATIONS

European Search Report re Application No. EP18194377.0 dated Feb. 13, 2019; 7 pgs.

(Continued)

*Primary Examiner* — William A Jerez Lora
(74) *Attorney, Agent, or Firm* — Foley & Lardner LLP

(57) ABSTRACT

A voice controlled device comprises a plurality of microphones, a communication interface, and a controller. The plurality of microphones are configured to receive voice inputs from one or more users for operation of the voice controlled device. The communication interface is configured to receive sensor data from an external device, the sensor data describing an environment of the voice controlled device. The controller is configured to operate a first subset of the plurality of microphones in response to first sensor data and a second subset of the plurality of microphones in response to second sensor data.

11 Claims, 37 Drawing Sheets

(51) Int. Cl.

| | | |
|---|---|---|
| G06F 3/16 | (2006.01) | |
| H04R 5/04 | (2006.01) | |
| A47K 17/00 | (2006.01) | |
| G06F 1/3287 | (2019.01) | |
| G06F 1/3231 | (2019.01) | |
| H04R 5/027 | (2006.01) | |
| G06F 3/01 | (2006.01) | |
| H04R 3/04 | (2006.01) | |
| C02F 1/00 | (2006.01) | |
| C02F 1/50 | (2006.01) | |
| C02F 1/68 | (2006.01) | |
| G01N 33/18 | (2006.01) | |
| G01N 35/00 | (2006.01) | |
| H04R 1/40 | (2006.01) | |
| G10L 21/0208 | (2013.01) | |

(52) U.S. Cl.
CPC ......... *C02F 1/685* (2013.01); *G01N 33/1826* (2013.01); *G01N 35/00871* (2013.01); *G06F 1/3231* (2013.01); *G06F 1/3287* (2013.01); *G06F 3/017* (2013.01); *G06F 3/167* (2013.01); *H04R 3/005* (2013.01); *H04R 3/04* (2013.01); *H04R 5/027* (2013.01); *H04R 5/04* (2013.01); *C02F 2209/006* (2013.01); *C02F 2209/008* (2013.01); *C02F 2307/06* (2013.01); *G01N 2035/009* (2013.01); *G01N 2035/00881* (2013.01); *G05B 2219/23027* (2013.01); *G05B 2219/23462* (2013.01); *G10L 21/0208* (2013.01); *H04R 1/406* (2013.01); *H04R 2227/005* (2013.01)

(58) Field of Classification Search
CPC ...... C02F 1/50; C02F 1/685; C02F 2209/006; C02F 2209/008; C02F 2307/06; G01N 33/1826; G01N 35/00871; G01N 2035/00881; G01N 2035/009; G06F 1/3231; G06F 1/3287; G06F 3/167; H04R 3/005; H04R 5/027; H04R 5/04
USPC .................................. 381/110, 122, 124, 315
See application file for complete search history.

(56) References Cited

U.S. PATENT DOCUMENTS

| | | |
|---|---|---|
| 4,641,292 A | 2/1987 | Tunnell et al. |
| 4,776,016 A | 10/1988 | Hansen |
| 4,780,906 A | 10/1988 | Rajasekaran et al. |
| 5,519,809 A | 5/1996 | Husseiny et al. |
| 5,548,335 A | 8/1996 | Mitsuhashi et al. |
| 5,573,506 A | 11/1996 | Vasko |
| 5,603,127 A | 2/1997 | Veal |
| 5,675,633 A | 10/1997 | Kopp et al. |
| D393,808 S | 4/1998 | Lindsey et al. |
| 5,749,324 A | 5/1998 | Moore |
| 6,012,029 A | 1/2000 | Cirino et al. |
| 6,228,057 B1 | 5/2001 | Vasko |
| 6,253,184 B1 | 6/2001 | Ruppert |
| 6,317,717 B1 | 11/2001 | Lindsey et al. |
| 6,339,429 B1 | 1/2002 | Schug |
| 6,405,939 B1 | 6/2002 | Mazzenga et al. |
| 6,560,027 B2 | 5/2003 | Meine |
| 6,606,280 B1 | 8/2003 | Knittel |
| 6,658,389 B1 | 12/2003 | Alpdemir |
| 6,658,572 B1 | 12/2003 | Craig |
| 6,691,151 B1 | 2/2004 | Cheyer et al. |
| 6,708,152 B2 | 3/2004 | Kivimaki |
| 6,724,873 B2 | 4/2004 | Senna Da Silva |
| 6,763,226 B1 | 7/2004 | McZeal, Jr. |
| 6,920,654 B2 | 7/2005 | Noguchi et al. |
| 6,934,684 B2 | 8/2005 | Alpdemir et al. |
| 7,010,263 B1 | 3/2006 | Patsiokas |
| 7,031,439 B2 | 4/2006 | Baxter, Jr. |
| 7,031,477 B1 | 4/2006 | Mella et al. |
| 7,149,814 B2 | 12/2006 | Neufeld et al. |
| 7,218,311 B2 | 5/2007 | Akins |
| 7,263,953 B2 | 9/2007 | Sundararajan |
| 7,287,737 B2 | 10/2007 | Rossi |
| 7,362,490 B2 | 4/2008 | Park |
| 7,408,439 B2 | 8/2008 | Wang et al. |
| 7,455,412 B2 | 11/2008 | Rottcher |
| 7,477,207 B2 | 1/2009 | Estep |
| 7,503,065 B1 | 3/2009 | Packingham et al. |
| 7,522,065 B2 | 4/2009 | Falcon |
| 7,551,354 B2 | 6/2009 | Horsten et al. |
| 7,589,893 B2 | 9/2009 | Rottcher |
| 7,617,108 B2 | 11/2009 | Matsubara et al. |
| 7,629,400 B2 | 12/2009 | Hyman |
| 7,697,827 B2 | 4/2010 | Konicek |
| 7,706,553 B2 | 4/2010 | Brown |
| 7,742,883 B2 | 6/2010 | Dayton et al. |
| 7,761,885 B2 | 7/2010 | Labrou et al. |
| 7,797,769 B2 | 9/2010 | Ozenick |
| 7,805,260 B2 | 9/2010 | Mischel et al. |
| 7,822,613 B2 | 10/2010 | Matsubara et al. |
| 7,853,414 B2 | 12/2010 | Mischel et al. |
| 7,948,831 B2 | 5/2011 | Orcutt et al. |
| 8,005,682 B2 | 8/2011 | Archibald et al. |
| 8,028,355 B2 | 10/2011 | Reeder et al. |
| 8,099,247 B2 | 1/2012 | Mischel et al. |
| 8,112,037 B2 | 2/2012 | Ketari |
| 8,119,968 B2 | 2/2012 | Bigolin |
| 8,135,624 B1 | 3/2012 | Ramalingam et al. |
| 8,165,341 B2 | 4/2012 | Rhoads |
| 8,175,883 B2 | 5/2012 | Grant et al. |
| 8,365,767 B2 | 2/2013 | Davidson et al. |
| 8,428,654 B2 | 4/2013 | Oh et al. |
| 8,498,670 B2 | 7/2013 | Cha et al. |
| D691,029 S | 10/2013 | Didehvar |
| D691,031 S | 10/2013 | Harwanko |
| D693,209 S | 11/2013 | Walker et al. |
| 8,572,772 B2 | 11/2013 | Wolf et al. |
| 8,594,850 B1 | 11/2013 | Gourlay |
| D696,573 S | 12/2013 | Didehvar |
| 8,606,413 B2 | 12/2013 | Picton |
| 8,818,182 B2 | 8/2014 | Konicek |
| 8,824,879 B2 | 9/2014 | Konicek |
| 8,827,587 B2 | 9/2014 | Didehvar |
| 8,831,418 B2 | 9/2014 | Konicek |
| 8,831,677 B2 | 9/2014 | Villa-Real |
| 8,851,305 B2 | 10/2014 | Didehvar |
| 8,851,372 B2 | 10/2014 | Zhou et al. |
| 8,880,360 B2 | 11/2014 | Mischel et al. |
| 8,902,315 B2 | 12/2014 | Fisher et al. |
| 8,910,402 B2 | 12/2014 | Mischel et al. |
| 8,917,982 B1 | 12/2014 | Konicek |
| 8,921,473 B1 | 12/2014 | Hyman |
| 8,923,692 B2 | 12/2014 | Konicek |
| 8,978,228 B2 | 3/2015 | Didehvar et al. |
| 8,985,442 B1 | 3/2015 | Zhou et al. |
| 9,016,565 B2 | 4/2015 | Zhou et al. |
| 9,032,564 B2 | 5/2015 | Reeder et al. |
| 9,071,579 B1 | 6/2015 | Bender |
| 9,105,202 B2 | 8/2015 | Mischel, Jr. |
| 9,107,529 B2 | 8/2015 | Didehvar et al. |
| 9,131,795 B2 | 9/2015 | Didehvar et al. |
| 9,153,074 B2 | 10/2015 | Zhou et al. |
| 9,155,373 B2 | 10/2015 | Allen et al. |
| 9,164,518 B2 | 10/2015 | Houghton |
| D746,667 S | 1/2016 | Vaccaro |
| 9,271,592 B2 | 3/2016 | Didehvar et al. |
| 9,286,808 B1 | 3/2016 | Raley et al. |
| 9,287,722 B2 | 3/2016 | Williams et al. |
| 9,342,829 B2 | 5/2016 | Zhou et al. |
| 9,380,287 B2 | 6/2016 | Nistico et al. |
| 9,412,264 B2 | 8/2016 | Geerlings et al. |
| 9,465,389 B2 | 10/2016 | Hyde et al. |
| 9,489,671 B2 | 11/2016 | Zhou et al. |
| 9,557,808 B2 | 1/2017 | Shon et al. |
| 9,564,130 B2 | 2/2017 | Choi et al. |

(56) References Cited

U.S. PATENT DOCUMENTS

| | | |
|---|---|---|
| 9,574,331 B2 | 2/2017 | Wright |
| 9,578,159 B2 | 2/2017 | Muthukumar |
| 9,600,832 B2 | 3/2017 | Zhou |
| 9,665,124 B2 | 5/2017 | Kim et al. |
| 9,686,579 B2 | 6/2017 | Majid |
| 9,694,229 B2 | 7/2017 | Taft |
| 9,734,827 B2 | 8/2017 | Shin et al. |
| 10,282,166 B2 | 5/2019 | Fountaine |
| 2001/0055371 A1 | 12/2001 | Baxter, Jr. |
| 2002/0007510 A1 | 1/2002 | Mann |
| 2002/0021288 A1 | 2/2002 | Schug |
| 2002/0049589 A1 | 4/2002 | Poirier |
| 2002/0188571 A1 | 12/2002 | Pilgrim |
| 2003/0114202 A1 | 6/2003 | Suh et al. |
| 2003/0120183 A1 | 6/2003 | Simmons |
| 2003/0163324 A1 | 8/2003 | Abbasi |
| 2003/0206491 A1 | 11/2003 | Pacheco et al. |
| 2004/0001588 A1 | 1/2004 | Hairston |
| 2004/0040086 A1 | 3/2004 | Eisenberg et al. |
| 2004/0059573 A1 | 3/2004 | Cheong |
| 2004/0066710 A1 | 4/2004 | Yuen et al. |
| 2004/0117275 A1 | 6/2004 | Billera |
| 2004/0128137 A1 | 7/2004 | Bush et al. |
| 2004/0143440 A1 | 7/2004 | Prasad et al. |
| 2004/0193326 A1 | 9/2004 | Phillips et al. |
| 2004/0215464 A1 | 10/2004 | Nelson |
| 2004/0256009 A1 | 12/2004 | Valenzuela |
| 2005/0021341 A1 | 1/2005 | Matsubara et al. |
| 2005/0195309 A1 | 9/2005 | Kim et al. |
| 2006/0098264 A1 | 5/2006 | Park |
| 2006/0101116 A1 | 5/2006 | Rittman et al. |
| 2006/0271369 A1 | 11/2006 | Poirier |
| 2007/0067054 A1 | 3/2007 | Danish |
| 2007/0123251 A1 | 5/2007 | McElvaney |
| 2007/0182571 A1 | 8/2007 | Kennish |
| 2007/0260460 A1 | 11/2007 | Hyatt |
| 2008/0019489 A1 | 1/2008 | Lynn |
| 2008/0037727 A1 | 2/2008 | Sivertsen et al. |
| 2008/0146906 A1 | 6/2008 | Baker et al. |
| 2008/0154394 A1 | 6/2008 | Lin |
| 2008/0163416 A1 | 7/2008 | Go |
| 2008/0253589 A1 | 10/2008 | Trahms |
| 2008/0285886 A1 | 11/2008 | Allen |
| 2009/0021486 A1 | 1/2009 | Chaudhri et al. |
| 2009/0112603 A1 | 4/2009 | Archibald et al. |
| 2009/0117816 A1 | 5/2009 | Nakamura |
| 2009/0253463 A1 | 10/2009 | Shin et al. |
| 2009/0316285 A1 | 12/2009 | Bigolin |
| 2010/0076615 A1 | 3/2010 | Daniel et al. |
| 2010/0082351 A1 | 4/2010 | Lee |
| 2010/0180754 A1 | 7/2010 | Brown et al. |
| 2010/0207775 A1 | 8/2010 | Lenneman et al. |
| 2010/0258618 A1 | 10/2010 | Philbrick et al. |
| 2011/0133105 A1 | 6/2011 | Simon |
| 2011/0139269 A1 | 6/2011 | Rogers |
| 2011/0220425 A1 | 9/2011 | Denk et al. |
| 2012/0065972 A1 | 3/2012 | Strifler et al. |
| 2012/0253824 A1 | 10/2012 | Alcantara Talavera |
| 2012/0257123 A1 | 10/2012 | Lee |
| 2013/0033739 A1 | 2/2013 | Flatte et al. |
| 2013/0041665 A1 | 2/2013 | Jang et al. |
| 2013/0066636 A1 | 3/2013 | Singhal |
| 2013/0145272 A1 | 6/2013 | Boggie et al. |
| 2013/0151286 A1 | 6/2013 | Kablotsky et al. |
| 2013/0151422 A1 | 6/2013 | Berry et al. |
| 2013/0218562 A1 | 8/2013 | Igarashi |
| 2013/0237272 A1 | 9/2013 | Prasad |
| 2013/0347018 A1 | 12/2013 | Limp et al. |
| 2014/0001977 A1 | 1/2014 | Zacharchuk et al. |
| 2014/0055624 A1 | 2/2014 | Gaines et al. |
| 2014/0123057 A1 | 5/2014 | Eigner et al. |
| 2014/0128032 A1 | 5/2014 | Muthukumar |
| 2014/0142949 A1 | 5/2014 | Newman |
| 2014/0194262 A1 | 7/2014 | Cooper |
| 2014/0206479 A1 | 7/2014 | Marty et al. |
| 2014/0254896 A1 | 9/2014 | Zhou et al. |
| 2014/0278199 A1 | 9/2014 | Rajagopal et al. |
| 2014/0283291 A1 | 9/2014 | Austin |
| 2014/0337036 A1* | 11/2014 | Haiut .................. G10L 15/20 704/275 |
| 2015/0061387 A1 | 3/2015 | Daniel et al. |
| 2015/0085059 A1 | 3/2015 | Fisher et al. |
| 2015/0156030 A1* | 6/2015 | Fadell ................ H04L 12/2816 700/90 |
| 2015/0189068 A1 | 7/2015 | Mohan et al. |
| 2015/0190667 A1 | 7/2015 | Balandis et al. |
| 2015/0193193 A1 | 7/2015 | Khaira et al. |
| 2015/0253753 A1 | 9/2015 | Bennett et al. |
| 2015/0271557 A1 | 9/2015 | Tabe |
| 2015/0304300 A1 | 10/2015 | Bender |
| 2015/0309543 A1 | 10/2015 | Bleistern |
| 2015/0312453 A1 | 10/2015 | Gaines et al. |
| 2016/0019868 A1 | 1/2016 | Park et al. |
| 2016/0048990 A1 | 2/2016 | Seo et al. |
| 2016/0070085 A1 | 3/2016 | Mischel, Jr. |
| 2016/0076231 A1 | 3/2016 | Goel et al. |
| 2016/0076909 A1 | 3/2016 | Klicpera |
| 2016/0129464 A1 | 5/2016 | Frommer |
| 2016/0134966 A1* | 5/2016 | Fitzgerald ................ H04R 3/00 381/123 |
| 2016/0170542 A1 | 6/2016 | Park et al. |
| 2016/0189281 A1 | 6/2016 | Kurnit et al. |
| 2016/0206244 A1 | 7/2016 | Rogers |
| 2016/0220170 A1 | 8/2016 | Hasegawa et al. |
| 2016/0223518 A1 | 8/2016 | Yamaya et al. |
| 2016/0223519 A1 | 8/2016 | Yamaya et al. |
| 2016/0223548 A1 | 8/2016 | Kizuka et al. |
| 2016/0223549 A1 | 8/2016 | Kizuka et al. |
| 2016/0223550 A1 | 8/2016 | Hasegawa et al. |
| 2016/0223551 A1 | 8/2016 | Kizuka et al. |
| 2016/0223552 A1 | 8/2016 | Kizuka et al. |
| 2016/0224315 A1 | 8/2016 | Zhang et al. |
| 2016/0253150 A1 | 9/2016 | Williams et al. |
| 2016/0258144 A1 | 9/2016 | Tayenaka et al. |
| 2016/0261425 A1 | 9/2016 | Horton et al. |
| 2016/0267708 A1 | 9/2016 | Nistico et al. |
| 2016/0350589 A1 | 12/2016 | Chiu |
| 2016/0371977 A1 | 12/2016 | Wingate et al. |
| 2017/0039359 A1 | 2/2017 | Yang et al. |
| 2017/0046023 A1 | 2/2017 | Kumar et al. |
| 2017/0050201 A1 | 2/2017 | Deivasigamani et al. |
| 2017/0073070 A1 | 3/2017 | Xing |
| 2017/0076212 A1 | 3/2017 | Shams et al. |
| 2017/0103440 A1 | 4/2017 | Xing et al. |
| 2017/0115742 A1 | 4/2017 | Xing et al. |
| 2017/0124770 A1 | 5/2017 | Vats |
| 2017/0161720 A1 | 6/2017 | Xing et al. |
| 2017/0164162 A1 | 6/2017 | Zur et al. |
| 2017/0165481 A1 | 6/2017 | Menon |
| 2017/0172462 A1 | 6/2017 | Alghazi |
| 2017/0185383 A1 | 6/2017 | Sarkar et al. |
| 2017/0192402 A1 | 7/2017 | Karp et al. |
| 2017/0199649 A1 | 7/2017 | Kukkee |
| 2018/0352356 A1* | 12/2018 | Amir .................... G06F 1/3215 |
| 2019/0090056 A1 | 3/2019 | Rexach |
| 2019/0120809 A1 | 4/2019 | Rexach |
| 2019/0146438 A1 | 5/2019 | Rexach |
| 2019/0212976 A1 | 7/2019 | Fountaine |

FOREIGN PATENT DOCUMENTS

| | | | |
|---|---|---|---|
| CN | 1412687 | A | 4/2003 |
| CN | 2591682 | Y | 12/2003 |
| CN | 2717364 | Y | 8/2005 |
| CN | 1954292 | A | 4/2007 |
| CN | 2916783 | Y | 6/2007 |
| CN | 100345085 | C | 10/2007 |
| CN | 101226603 | A | 7/2008 |
| CN | 101231582 | A | 7/2008 |
| CN | 101320439 | A | 12/2008 |
| CN | 100461109 | C | 2/2009 |
| CN | 101822501 | A | 9/2010 |
| CN | 101893967 | A | 11/2010 |
| CN | 101959449 | A | 1/2011 |

(56) References Cited

FOREIGN PATENT DOCUMENTS

| | | | |
|---|---|---|---|
| CN | 201710242 U | 1/2011 |
| CN | 201725194 U | 1/2011 |
| CN | 201781110 U | 3/2011 |
| CN | 201879593 U | 6/2011 |
| CN | 201879594 U | 6/2011 |
| CN | 201916568 U | 8/2011 |
| CN | 201968563 U | 9/2011 |
| CN | 201977666 U | 9/2011 |
| CN | 102225015 A | 10/2011 |
| CN | 202003182 U | 10/2011 |
| CN | 202096129 U | 1/2012 |
| CN | 202112981 U | 1/2012 |
| CN | 102354184 A | 2/2012 |
| CN | 202128568 U | 2/2012 |
| CN | 202197903 U | 4/2012 |
| CN | 102434710 A | 5/2012 |
| CN | 301968512.7 S | 6/2012 |
| CN | 101822501 B | 7/2012 |
| CN | 102535886 A | 7/2012 |
| CN | 102561735 A | 7/2012 |
| CN | 202365692 U | 8/2012 |
| CN | 202397346 U | 8/2012 |
| CN | 202401786 U | 8/2012 |
| CN | 202401787 U | 8/2012 |
| CN | 302031727.6 S | 8/2012 |
| CN | 101947152 B | 9/2012 |
| CN | 202441079 U | 9/2012 |
| CN | 202509570 U | 10/2012 |
| CN | 202533867 U | 11/2012 |
| CN | 202589427 U | 12/2012 |
| CN | 102225015 B | 1/2013 |
| CN | 102872989 A | 1/2013 |
| CN | 202654384 U | 1/2013 |
| CN | 202758459 U | 2/2013 |
| CN | 202778764 U | 3/2013 |
| CN | 103006124 A | 4/2013 |
| CN | 103016814 A | 4/2013 |
| CN | 202858998 U | 4/2013 |
| CN | 202884299 U | 4/2013 |
| CN | 202893547 U | 4/2013 |
| CN | 103170413 A | 6/2013 |
| CN | 202962729 U | 6/2013 |
| CN | 203022964 U | 6/2013 |
| CN | 203074496 U | 7/2013 |
| CN | 203155431 U | 8/2013 |
| CN | 203169029 U | 9/2013 |
| CN | 203170465 U | 9/2013 |
| CN | 203175072 U | 9/2013 |
| CN | 203178709 U | 9/2013 |
| CN | 102488593 B | 11/2013 |
| CN | 203328599 U | 12/2013 |
| CN | 203366006 U | 12/2013 |
| CN | 103505113 A | 1/2014 |
| CN | 103533415 A | 1/2014 |
| CN | 203400793 U | 1/2014 |
| CN | 203475531 U | 3/2014 |
| CN | 103705154 A | 4/2014 |
| CN | 103792947 A | 5/2014 |
| CN | 103870265 A | 6/2014 |
| CN | 103876668 A | 6/2014 |
| CN | 203669066 U | 6/2014 |
| CN | 103955672 A | 7/2014 |
| CN | 103985387 A | 8/2014 |
| CN | 104000527 A | 8/2014 |
| CN | 203786891 U | 8/2014 |
| CN | 203789802 U | 8/2014 |
| CN | 203873652 U | 10/2014 |
| CN | 203914713 U | 11/2014 |
| CN | 203935117 U | 11/2014 |
| CN | 104246644 A | 12/2014 |
| CN | 204016111 U | 12/2014 |
| CN | 104348960 A | 2/2015 |
| CN | 204218777 U | 3/2015 |
| CN | 104500827 A | 4/2015 |
| CN | 104534675 A | 4/2015 |
| CN | 104545599 A | 4/2015 |
| CN | 104545600 A | 4/2015 |
| CN | 104563547 A | 4/2015 |
| CN | 204284631 U | 4/2015 |
| CN | 104602419 A | 5/2015 |
| CN | 104633947 A | 5/2015 |
| CN | 104640323 A | 5/2015 |
| CN | 104640324 A | 5/2015 |
| CN | 104656513 A | 5/2015 |
| CN | 104656877 A | 5/2015 |
| CN | 104657104 A | 5/2015 |
| CN | 204318598 U | 5/2015 |
| CN | 204379109 U | 6/2015 |
| CN | 204394369 U | 6/2015 |
| CN | 104754822 A | 7/2015 |
| CN | 104763836 A | 7/2015 |
| CN | 104766508 A | 7/2015 |
| CN | 104776587 A | 7/2015 |
| CN | 104792022 A | 7/2015 |
| CN | 104799734 A | 7/2015 |
| CN | 204440549 U | 7/2015 |
| CN | 104838353 A | 8/2015 |
| CN | 204533735 U | 8/2015 |
| CN | 104898744 A | 9/2015 |
| CN | 104930716 A | 9/2015 |
| CN | 104932297 A | 9/2015 |
| CN | 204600304 U | 9/2015 |
| CN | 204654752 U | 9/2015 |
| CN | 204665632 U | 9/2015 |
| CN | 204730475 U | 10/2015 |
| CN | 105078450 A | 11/2015 |
| CN | 105093951 A | 11/2015 |
| CN | 105093957 A | 11/2015 |
| CN | 105094133 A | 11/2015 |
| CN | 105100734 A | 11/2015 |
| CN | 105100736 A | 11/2015 |
| CN | 204738562 U | 11/2015 |
| CN | 204765320 U | 11/2015 |
| CN | 104173124 B | 12/2015 |
| CN | 105148421 A | 12/2015 |
| CN | 105159102 A | 12/2015 |
| CN | 105162237 A | 12/2015 |
| CN | 105186666 A | 12/2015 |
| CN | 204828975 U | 12/2015 |
| CN | 204911852 U | 12/2015 |
| CN | 204911859 U | 12/2015 |
| CN | 105223816 A | 1/2016 |
| CN | 105266692 A | 1/2016 |
| CN | 105281998 A | 1/2016 |
| CN | 204945654 U | 1/2016 |
| CN | 204945795 U | 1/2016 |
| CN | 204950724 U | 1/2016 |
| CN | 204971277 U | 1/2016 |
| CN | 204989805 U | 1/2016 |
| CN | 204992741 U | 1/2016 |
| CN | 204992742 U | 1/2016 |
| CN | 205004823 U | 1/2016 |
| CN | 102872989 B | 2/2016 |
| CN | 105310577 A | 2/2016 |
| CN | 105346483 A | 2/2016 |
| CN | 205014583 U | 2/2016 |
| CN | 205042029 U | 2/2016 |
| CN | 103876668 B | 3/2016 |
| CN | 205107493 U | 3/2016 |
| CN | 104000527 B | 4/2016 |
| CN | 105487414 A | 4/2016 |
| CN | 105528747 A | 4/2016 |
| CN | 205181198 U | 4/2016 |
| CN | 105561472 A | 5/2016 |
| CN | 105562244 A | 5/2016 |
| CN | 105563464 A | 5/2016 |
| CN | 205236027 U | 5/2016 |
| CN | 205247128 U | 5/2016 |
| CN | 105642458 A | 6/2016 |
| CN | 105650882 A | 6/2016 |
| CN | 205281285 U | 6/2016 |
| CN | 205334083 U | 6/2016 |
| CN | 205334086 U | 6/2016 |
| CN | 205334090 U | 6/2016 |

(56) References Cited

FOREIGN PATENT DOCUMENTS

| | | |
|---|---|---|
| CN | 205353614 U | 6/2016 |
| CN | 105739337 A | 7/2016 |
| CN | 105747959 A | 7/2016 |
| CN | 105756466 A | 7/2016 |
| CN | 105783275 A | 7/2016 |
| CN | 105785778 A | 7/2016 |
| CN | 205375038 U | 7/2016 |
| CN | 105822095 A | 8/2016 |
| CN | 105832222 A | 8/2016 |
| CN | 105840884 A | 8/2016 |
| CN | 105854185 A | 8/2016 |
| CN | 105902217 A | 8/2016 |
| CN | 105903584 A | 8/2016 |
| CN | 205409005 U | 8/2016 |
| CN | 205411012 U | 8/2016 |
| CN | 205427467 U | 8/2016 |
| CN | 205427473 U | 8/2016 |
| CN | 205428168 U | 8/2016 |
| CN | 205504075 U | 8/2016 |
| CN | 205518291 U | 8/2016 |
| CN | 205534396 U | 8/2016 |
| CN | 103533391 B | 9/2016 |
| CN | 105919488 A | 9/2016 |
| CN | 105928208 A | 9/2016 |
| CN | 105962818 A | 9/2016 |
| CN | 105971082 A | 9/2016 |
| CN | 205550618 U | 9/2016 |
| CN | 205550619 U | 9/2016 |
| CN | 205563996 U | 9/2016 |
| CN | 105996860 A | 10/2016 |
| CN | 106020293 A | 10/2016 |
| CN | 106027340 A | 10/2016 |
| CN | 106037560 A | 10/2016 |
| CN | 205637686 U | 10/2016 |
| CN | 205638101 U | 10/2016 |
| CN | 104143326 B | 11/2016 |
| CN | 106131340 A | 11/2016 |
| CN | 106139393 A | 11/2016 |
| CN | 106157418 A | 11/2016 |
| CN | 205745606 U | 11/2016 |
| CN | 106193201 A | 12/2016 |
| CN | 106200461 A | 12/2016 |
| CN | 106216152 A | 12/2016 |
| CN | 106255619 A | 12/2016 |
| CN | 205783854 U | 12/2016 |
| CN | 205796322 U | 12/2016 |
| CN | 205814236 U | 12/2016 |
| CN | 205822832 U | 12/2016 |
| CN | 205831560 U | 12/2016 |
| CN | 106264249 A | 1/2017 |
| CN | 106269321 A | 1/2017 |
| CN | 106302805 A | 1/2017 |
| CN | 106303052 A | 1/2017 |
| CN | 106354042 A | 1/2017 |
| CN | 106354185 A | 1/2017 |
| CN | 205851137 U | 1/2017 |
| CN | 205903997 U | 1/2017 |
| CN | 104545600 B | 2/2017 |
| CN | 106358811 A | 2/2017 |
| CN | 106384192 A | 2/2017 |
| CN | 106391361 A | 2/2017 |
| CN | 106406110 A | 2/2017 |
| CN | 106406356 A | 2/2017 |
| CN | 106462681 A | 2/2017 |
| CN | 205914308 U | 2/2017 |
| CN | 205966215 U | 2/2017 |
| CN | 104603673 B | 3/2017 |
| CN | 206007121 U | 3/2017 |
| CN | 206054817 U | 3/2017 |
| CN | 206060826 U | 3/2017 |
| CN | 104534675 B | 4/2017 |
| CN | 106552396 A | 4/2017 |
| CN | 106552723 A | 4/2017 |
| CN | 106594379 A | 4/2017 |
| CN | 206080352 U | 4/2017 |
| CN | 206104217 U | 4/2017 |
| CN | 206130749 U | 4/2017 |
| CN | 206133207 U | 4/2017 |
| CN | 206133803 U | 4/2017 |
| CN | 106622709 A | 5/2017 |
| CN | 106630325 A | 5/2017 |
| CN | 106647317 A | 5/2017 |
| CN | 106667326 A | 5/2017 |
| CN | 106679049 A | 5/2017 |
| CN | 106681156 A | 5/2017 |
| CN | 106681221 A | 5/2017 |
| CN | 106707547 A | 5/2017 |
| CN | 106708377 A | 5/2017 |
| CN | 106724024 A | 5/2017 |
| CN | 106773766 A | 5/2017 |
| CN | 106782559 A | 5/2017 |
| CN | 106790628 A | 5/2017 |
| CN | 206138585 U | 5/2017 |
| CN | 206151337 U | 5/2017 |
| CN | 206166780 U | 5/2017 |
| CN | 103970260 B | 6/2017 |
| CN | 106805818 A | 6/2017 |
| CN | 106805934 A | 6/2017 |
| CN | 106859451 A | 6/2017 |
| CN | 106898173 A | 6/2017 |
| CN | 106901636 A | 6/2017 |
| CN | 206285017 U | 6/2017 |
| CN | 103942941 B | 7/2017 |
| CN | 106913260 A | 7/2017 |
| CN | 106920303 A | 7/2017 |
| CN | 106969495 A | 7/2017 |
| CN | 106980385 A | 7/2017 |
| CN | 106980803 A | 7/2017 |
| CN | 206331476 U | 7/2017 |
| CN | 107020208 A | 8/2017 |
| CN | 107021036 A | 8/2017 |
| CN | 107037758 A | 8/2017 |
| CN | 206369947 U | 8/2017 |
| DE | 40 22 511 A1 | 1/1992 |
| DE | 20 2011 110 066 U1 | 11/2012 |
| DE | 10 2017 102 082 A1 | 8/2017 |
| EP | 0 876 035 A2 | 11/1998 |
| EP | 1 406 133 A2 | 4/2004 |
| EP | 1 113 416 B1 | 1/2007 |
| EP | 2 130 721 A1 | 12/2009 |
| EP | 2 375 709 A1 | 10/2011 |
| EP | 2 515 164 A1 | 10/2012 |
| EP | 2 130 721 B1 | 11/2012 |
| EP | 2 778 928 A2 | 9/2014 |
| EP | 2 942 698 A1 | 11/2015 |
| EP | 2 975 449 A1 | 1/2016 |
| EP | 3 021 074 A1 | 5/2016 |
| EP | 3 029 209 A2 | 6/2016 |
| EP | 2 893 388 B1 | 8/2016 |
| EP | 3 131 022 A1 | 2/2017 |
| EP | 2 668 726 B1 | 7/2017 |
| FR | 2800571 A1 | 5/2001 |
| FR | 2832016 A1 | 5/2003 |
| GB | 2 300 742 A | 11/1996 |
| GB | 2 329 800 A | 3/1999 |
| GB | 2 401 752 A | 11/2004 |
| GB | 2 357 943 B | 12/2004 |
| GB | 2 420 251 A | 5/2006 |
| GB | 2 424 730 A | 10/2006 |
| GB | 2 495 280 A | 4/2013 |
| GB | 2 500 168 A | 9/2013 |
| GB | 2 529 645 A | 3/2016 |
| JP | 07-055755 A | 3/1995 |
| JP | 10-117212 A | 5/1998 |
| JP | 11-511301 A | 9/1999 |
| JP | 2001-005485 A | 1/2001 |
| JP | 2001-027897 A | 1/2001 |
| JP | 2001-266254 A | 9/2001 |
| JP | 2001-518828 A | 10/2001 |
| JP | 2002-010369 A | 1/2002 |
| JP | 2002-010942 A | 1/2002 |
| JP | 2002-183579 A | 6/2002 |
| JP | 2002-207832 A | 7/2002 |
| JP | 2002-311990 A | 10/2002 |

(56) References Cited

FOREIGN PATENT DOCUMENTS

| | | |
|---|---|---|
| JP | 2003-506148 A | 2/2003 |
| JP | 2004-504077 A | 2/2004 |
| JP | 2005-527256 A | 9/2005 |
| JP | 2006-121671 A | 5/2006 |
| JP | 2006-515694 A | 6/2006 |
| JP | 3915291 B2 | 5/2007 |
| JP | 2008-507000 A | 3/2008 |
| JP | 2008-110203 A6 | 7/2008 |
| JP | 2009-003908 A | 1/2009 |
| JP | 2009-516240 A | 4/2009 |
| JP | 2009-291657 A | 12/2009 |
| JP | 2011-086315 A | 4/2011 |
| JP | 2012-179370 A | 9/2012 |
| JP | 2013-088906 A | 5/2013 |
| JP | 2014-222245 A | 11/2014 |
| JP | 2014-532250 A | 12/2014 |
| JP | 2015-509241 A | 3/2015 |
| JP | 2016-502120 A | 1/2016 |
| JP | 5887026 B2 | 3/2016 |
| JP | 5922195 B2 | 5/2016 |
| JP | 2017-513348 A | 5/2017 |
| JP | 2017-517780 A | 6/2017 |
| JP | 6144849 B1 | 6/2017 |
| KR | 1020010020875 A | 3/2001 |
| KR | 1020010111127 A | 12/2001 |
| KR | 1020020007992 A | 1/2002 |
| KR | 1020040100995 A | 12/2004 |
| KR | 1020070009568 A | 1/2007 |
| KR | 100700537 B1 | 3/2007 |
| KR | 1020080037639 A | 4/2008 |
| KR | 1020080056013 A | 6/2008 |
| KR | 100896245 B1 | 4/2009 |
| KR | 100978689 B1 | 8/2010 |
| KR | 101054487 B1 | 7/2011 |
| KR | 1020110098878 A | 9/2011 |
| KR | 101085011 B1 | 11/2011 |
| KR | 1020140022332 A | 2/2014 |
| KR | 1020140095998 A | 8/2014 |
| KR | 1020140139982 A | 12/2014 |
| KR | 1020150114983 A | 10/2015 |
| KR | 1020150123857 A | 11/2015 |
| KR | 1020160065574 A | 6/2016 |
| KR | 1020160082939 A | 7/2016 |
| KR | 1020160086794 A | 7/2016 |
| KR | 101671148 B1 | 10/2016 |
| KR | 1020160122517 A | 10/2016 |
| KR | 1020170006233 A | 1/2017 |
| WO | WO-95/01757 A1 | 1/1995 |
| WO | WO-96/03741 A1 | 2/1996 |
| WO | WO-98/12685 A1 | 3/1998 |
| WO | WO-00/75915 A1 | 12/2000 |
| WO | WO-01/11896 A2 | 2/2001 |
| WO | WO-01/90912 A1 | 11/2001 |
| WO | WO-01/99096 A1 | 12/2001 |
| WO | WO-02/12966 A1 | 2/2002 |
| WO | WO-02/21274 A1 | 3/2002 |
| WO | WO-02/054309 A1 | 7/2002 |
| WO | WO-2004/032014 A1 | 4/2004 |
| WO | WO-2004/032113 A1 | 4/2004 |
| WO | WO-2004/105523 A1 | 12/2004 |
| WO | WO-2005/004446 A1 | 1/2005 |
| WO | WO-2005/061249 A1 | 7/2005 |
| WO | WO-2005/104772 A2 | 11/2005 |
| WO | WO-2005/107407 A2 | 11/2005 |
| WO | WO-2005/107407 A9 | 12/2005 |
| WO | WO-2006/052067 A1 | 5/2006 |
| WO | WO-2006/068123 A1 | 6/2006 |
| WO | WO-2006/093003 A1 | 9/2006 |
| WO | WO-2006/103437 A1 | 10/2006 |
| WO | WO-2007/034392 A2 | 3/2007 |
| WO | WO-2007/035675 A2 | 3/2007 |
| WO | WO-2007/047541 A2 | 4/2007 |
| WO | WO-2007/059051 A2 | 5/2007 |
| WO | WO-2007/145003 A1 | 12/2007 |
| WO | WO-2008/096944 A1 | 8/2008 |
| WO | WO-2008/144638 A2 | 11/2008 |
| WO | WO-2006/086863 A3 | 5/2009 |
| WO | WO-2009/061531 A1 | 5/2009 |
| WO | WO-2009/072064 A1 | 6/2009 |
| WO | WO-2010/029315 A2 | 3/2010 |
| WO | WO-2011/008164 A1 | 1/2011 |
| WO | WO-2011/074719 A1 | 6/2011 |
| WO | WO-2011/143885 A1 | 11/2011 |
| WO | WO-2011/146947 A2 | 11/2011 |
| WO | WO-2012/037049 A2 | 3/2012 |
| WO | WO-2012/067640 A1 | 5/2012 |
| WO | WO-2012/103408 A1 | 8/2012 |
| WO | WO-2012/128824 A1 | 9/2012 |
| WO | WO-2012/131674 A2 | 10/2012 |
| WO | WO-2012/131839 A1 | 10/2012 |
| WO | WO-2012/176217 A2 | 12/2012 |
| WO | WO-2013/014709 A1 | 1/2013 |
| WO | WO-2013/015364 A1 | 1/2013 |
| WO | WO-2013/022135 A1 | 2/2013 |
| WO | WO-2013/054839 A1 | 4/2013 |
| WO | WO-2013/075082 A1 | 5/2013 |
| WO | WO-2013/096341 A1 | 6/2013 |
| WO | WO-2013/101779 A1 | 7/2013 |
| WO | WO-2014/031321 A1 | 2/2014 |
| WO | WO-2014/033306 A1 | 3/2014 |
| WO | WO-2014/109104 A1 | 7/2014 |
| WO | WO-2014/117647 A1 | 8/2014 |
| WO | WO-2014/121486 A1 | 8/2014 |
| WO | WO-2014/122558 A1 | 8/2014 |
| WO | WO-2014/136131 A1 | 9/2014 |
| WO | WO-2015/018253 A1 | 2/2015 |
| WO | WO-2015/025251 A1 | 2/2015 |
| WO | WO-2015/029362 A1 | 3/2015 |
| WO | WO-2015/037104 A1 | 3/2015 |
| WO | WO-2015/068954 A1 | 5/2015 |
| WO | WO-2015/068959 A1 | 5/2015 |
| WO | WO-2015/102258 A1 | 7/2015 |
| WO | WO-2015/130970 A1 | 9/2015 |
| WO | WO-2015/134458 A1 | 9/2015 |
| WO | WO-2015/140816 A1 | 9/2015 |
| WO | WO-2015/146179 A1 | 10/2015 |
| WO | WO-2015/148578 A2 | 10/2015 |
| WO | WO-2015/167008 A1 | 11/2015 |
| WO | WO-2015/170253 A1 | 11/2015 |
| WO | WO-2015/174597 A1 | 11/2015 |
| WO | WO-2015/177760 A2 | 11/2015 |
| WO | WO-2015/188268 A1 | 12/2015 |
| WO | WO-2015/200342 A1 | 12/2015 |
| WO | WO-2016/000098 A1 | 1/2016 |
| WO | WO-2016/007926 A1 | 1/2016 |
| WO | WO-2016/026324 A1 | 2/2016 |
| WO | WO-2016/063564 A1 | 4/2016 |
| WO | WO-2016/080713 A1 | 5/2016 |
| WO | WO-2016/083906 A1 | 6/2016 |
| WO | WO-2016/092502 A1 | 6/2016 |
| WO | WO-2016/120887 A1 | 8/2016 |
| WO | WO-2016/141345 A1 | 9/2016 |
| WO | WO-2016/149048 A1 | 9/2016 |
| WO | WO-2016/164917 A1 | 10/2016 |
| WO | WO-2016/167504 A1 | 10/2016 |
| WO | WO-2016/192369 A1 | 12/2016 |
| WO | WO-2017/003494 A1 | 1/2017 |
| WO | WO-2017/005013 A1 | 1/2017 |
| WO | WO-2017/015847 A1 | 2/2017 |
| WO | WO-2017/015848 A1 | 2/2017 |
| WO | WO-2017/020233 A1 | 2/2017 |
| WO | WO-2017/020234 A1 | 2/2017 |
| WO | WO-2017/028066 A1 | 2/2017 |
| WO | WO-2017/051403 A1 | 3/2017 |
| WO | WO2017/074406 | 5/2017 |
| WO | WO-2017/085487 A1 | 5/2017 |
| WO | WO-2017/090826 A1 | 6/2017 |
| WO | WO-2017/092526 A1 | 6/2017 |
| WO | WO-2017/093439 A1 | 6/2017 |
| WO | WO-2017/093954 A1 | 6/2017 |

(56) References Cited

FOREIGN PATENT DOCUMENTS

| WO | WO-2017/116876 A1 | 7/2017 |
|---|---|---|
| WO | WO-2017/133431 A1 | 8/2017 |

OTHER PUBLICATIONS

European Search Report re Application No. EP18194378.8 dated Feb. 13, 2019; 7 pgs.
European Search Report re Application No. EP18194376.2 dated Feb. 13, 2019; 7 pgs.

* cited by examiner

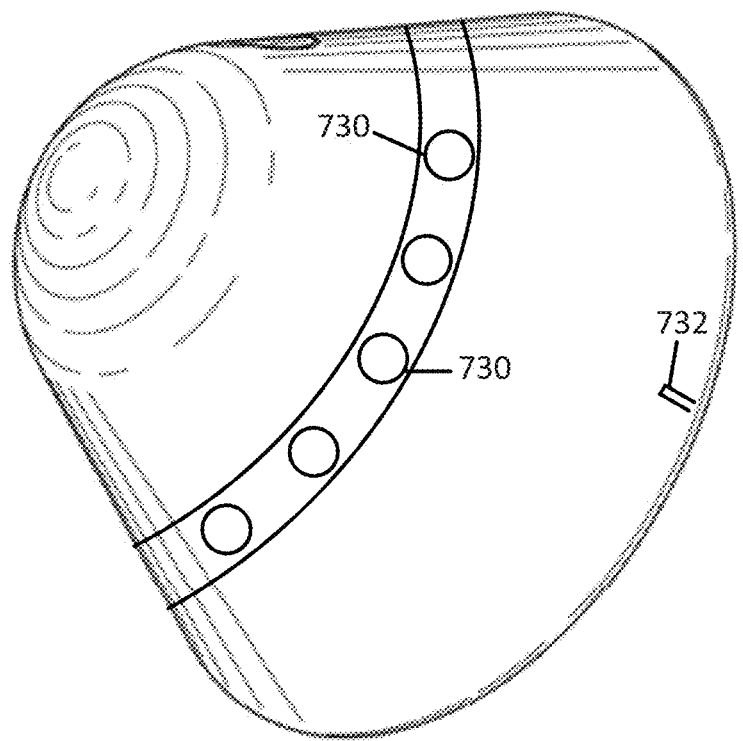
FIG. 30A
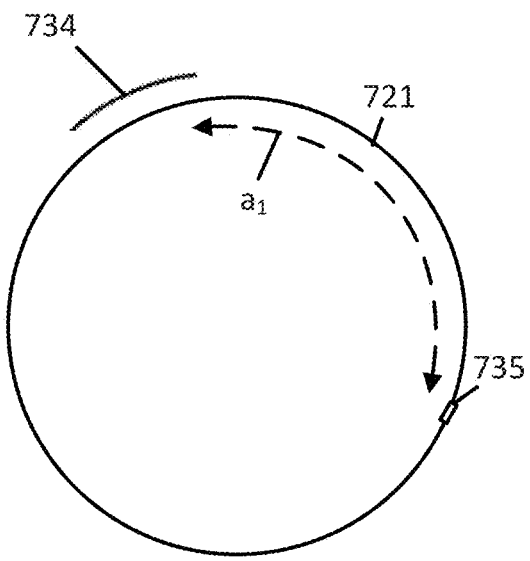 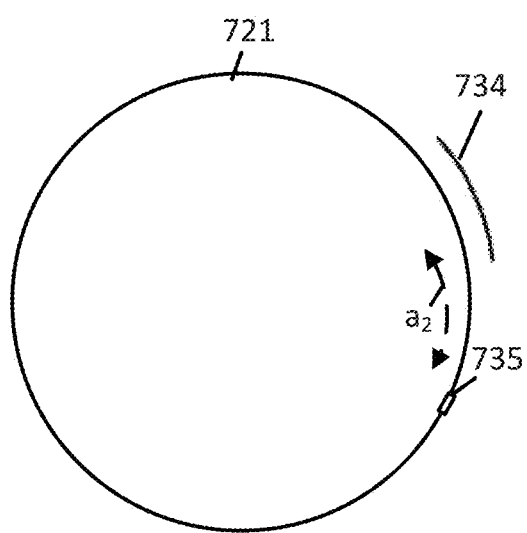
FIG. 30B  FIG. 30C

POWER OPERATION OF INTELLIGENT DEVICES

CROSS-REFERENCE TO RELATED APPLICATIONS

This application claims the benefit of and priority to U.S. Provisional Application No. 62/559,199 filed Sep. 15, 2017, which is hereby incorporated by reference in its entirety.

FIELD

This disclosure relates to the field of kitchen devices or appliances and bathroom devices or appliances, and more specifically, intelligent kitchen devices and intelligent bathroom devices that provide functions to a user in response to sensor data collected in relation to the user. This disclosure further relates to intelligent kitchen devices and intelligent bathroom devices that are connected to each other and/or another network through a home hub communication device and may be controllable via a mobile application and/or voice commands.

BACKGROUND

A virtual assistant provides information, performs tasks, or provides services to a user. The virtual assistant may be a device or a software agent. The virtual assistant may receive voice commands through natural language processing. The information provided by the virtual assistant may include data that is easily accessed from the internet, including the weather, traffic, music lyrics, or the news. The tasks performed by the virtual assistant may include making dinner reservations, requesting a driver, performing an internet search, or checking the news. The services provided by the virtual assistant may include playing music, setting a thermostat, reading a book, setting an alarm, or placing a call.

SUMMARY

One implementation of the present disclosure is a system of household appliances for providing services according to user identity. The system includes a first appliance, a server, and a second appliance. The first appliance is configured to collect sensor data associated with an identity of a user. The server is configured to receive the sensor data from the first appliance and analyze the sensor data to determine the identity of the user. The second appliance is configured to provide a device function to the user based on the identity determined from the sensor data collected by the first appliance.

Another implementation of the present disclosure is a method for providing services with household appliances according to user identity. The method includes receiving sensor data collected by a first appliance. The sensor data is associated with an identity of a user. The method includes analyzing the sensor data from the first appliance to determine the identity of the user, accessing a user database using the identity of the user for a user configuration, and generating a command for a device function for a second appliance based on user configuration for the identity of the user.

Another implementation of the present disclosure is a communication system for providing feedback data for at least one water consuming device. The communication system includes a data collection interface, a controller, and an output interface. The data collection interface is configured to receive user data from at least one collection device. The controller is configured to perform an analysis of the user data from the at least one collection device. The output interface is configured to provide feedback data based on the analysis of the user data to a water consuming device.

Another implementation of the present disclosure is communication system for providing feedback data for water consuming devices. The communication system includes a data collection interface, a controller, and an output interface. The data collection interface is configured to receive user data from at least one water consuming device. The controller is configured to perform an analysis of the user data from the at least one water consuming device. The output interface is configured to provide feedback data based on the analysis of the user data.

Another implementation of the present disclosure is method for coordination of household devices. The method includes receiving, at a data collection interface, sensor data from at least one first device. The sensor data describes a state of a user. The method includes performing, using a controller, an analysis of the sensor data from the at least one first device and generating, using the controller, feedback data based on the analysis of the sensor data. The feedback data is configured to operate a second device based on the sensor data from the at least one first device. The at least one first device or the second device is a water consuming device.

Another implementation of the present disclosure is an apparatus for aggregation of water condition at household appliance. The apparatus includes a communication interface and a controller. The communication interface is configured to send a reporting message indicative of data collected by at least one appliance to a central server. The controller is configured to receive an analysis message from the central server. The analysis message indicates a condition of water from the at least one appliance or a condition of water in a geographic area associated with the at least one appliance. The controller is configured to provide an alert in response to the analysis message.

Another implementation of the present disclosure is a method for analyzing a reporting a condition of water. The method includes receiving a reporting message indicative of sensor data collected by at least one appliance. The reporting message includes an identifier for the at least one appliance. The method includes determining an indication of a condition of water based on the sensor data, accessing a database according to the identifier for the at least one appliance to determine one or more neighboring users, generating an analysis message including the indication of the condition of water, and sending the analysis message to the one or more neighboring users.

Another implementation of the present disclosure is an apparatus including at least one sensor and a controller. The at least one sensor is configured to collect data for a water condition associated with at least one first appliance. The controller is configured to perform an analysis of the data for the water condition, identify a resultant instruction in response to the analysis, and send the resultant instruction to at least one second appliance.

Another implementation of the present disclosure is an apparatus including a light source array, a communication interface, and a controller. The light source array includes one or more directional light sources. The communication interface is configured to receive user data from at least one appliance. The user data indicates an identity of a user. The controller is configured to analyze the identity of the user and activate the one or more directional light sources in response to the identity of the user.

Another implementation of the present disclosure is a method for commanding a light source array. The method includes receiving user data from at least one appliance. The user data indicates an identity of a user. The method includes analyzing, by a processor, the user data to identify at least one appliance to be illuminated for the user. The method includes generating, at the processor, a light command for a light source array comprising one or more directional light sources to illuminate at least a portion of the at least one appliance to be illuminated.

Another implementation of the present disclosure is an apparatus including a communication interface and a controller. The communication interface is configured to receive user data from at least one appliance. The user data indicates an identity of a user. The controller is configured to analyze the user data to identify at least one appliance to be illuminated for the user. The controller is configured to generate a light command for a light source array including one or more directional light sources to illuminate at least a portion of the at least one appliance to be illuminated.

Another implementation of the present disclosure is a mirror assembly including a mirror substrate, a sensor, and a controller. The mirror substrate is configured to provide a reflection of objects including a user. The sensor is configured to collect sensor data from the user. The controller is configured to analyze the sensor data and select an auxiliary command for an auxiliary device coordinated with the mirror assembly. The auxiliary command is selected for the user.

Another implementation of the present disclosure is a method for coordinating at least one auxiliary device with a mirror assembly. The method includes receiving sensor data for a user at the mirror assembly, performing an analysis on the sensor data, and selecting, based on the analysis, an auxiliary command for an auxiliary device coordinated with the mirror assembly.

The auxiliary device is spaced apart from the mirror assembly and the auxiliary command is selected for the user. Another implementation of the present disclosure is an apparatus including a controller for a mirror assembly and a communication interface. The controller is configured to analyze sensor data received from a sensor and select an auxiliary command for an auxiliary device coordinated with the mirror assembly. The auxiliary command is selected for the user. The communication interface is configured to send the auxiliary command to the auxiliary device.

Another implementation of the present disclosure is an apparatus including a voice controlled device includes an array of microphones, a communication interface, and a controller. The array of microphones is configured to receive voice inputs from one or more users for the operation of the voice controlled device. The communication interface is configured to receive sensor data from an external appliance, and the sensor data describes an environment of the voice controlled device. The controller is configured to operate a first subset of the array of microphones in response to first sensor data and a second subset of the plurality of microphones in response to second sensor data.

Another implementation of the present disclosure is an apparatus including a voice controlled device includes a housing, a dock, a microphone, and a coupling mechanism. The dock is configured to connect the housing to multiple host appliances. The coupling mechanism configured to receive an identification value indicative of docking between the voice controlled device and a currently connected host appliance. The microphone is configured to receive one or more voice inputs for the currently connected host appliance, and a command is provided based on the one or more voice inputs and the identification value.

BRIEF DESCRIPTION OF THE DRAWINGS

Exemplary embodiments are described herein with reference to the following drawings, according to an exemplary embodiment.

FIGS. 30A, 30B, AND 30C illustrate a magnetic coupling system for the interchangeable speaker.

DETAILED DESCRIPTION

A virtual assistant may record voice commands using a microphone and send the voice commands to a cloud system through a network connection. The cloud system may collect information in response to the voice commands and reply to the virtual assistant with the information. The following embodiments include household appliances that are integrated with a virtual assistant or otherwise interact with a virtual assistant to share data among the household appliances. The data is collected by one appliance and utilized by another appliance. The utilizing appliance provides services to a user, and the services are customized based on the data shared from the collecting appliance. In one example, the shared data includes identifying information for the user or characteristics of the user that are used to apply customization, configuration, or preferences to the services provided by the utilizing appliance. The following embodiments improve the operation of the household appliances by increasing the data set from which personalized device functions can be selected and performed. For example, data otherwise unavailable at the utilizing appliance is detected at shared from the collecting appliance. The following embodiments improve the communication networks by standardizing the exchange of data among household appliances.

Summary of Appliances

Figure 1:
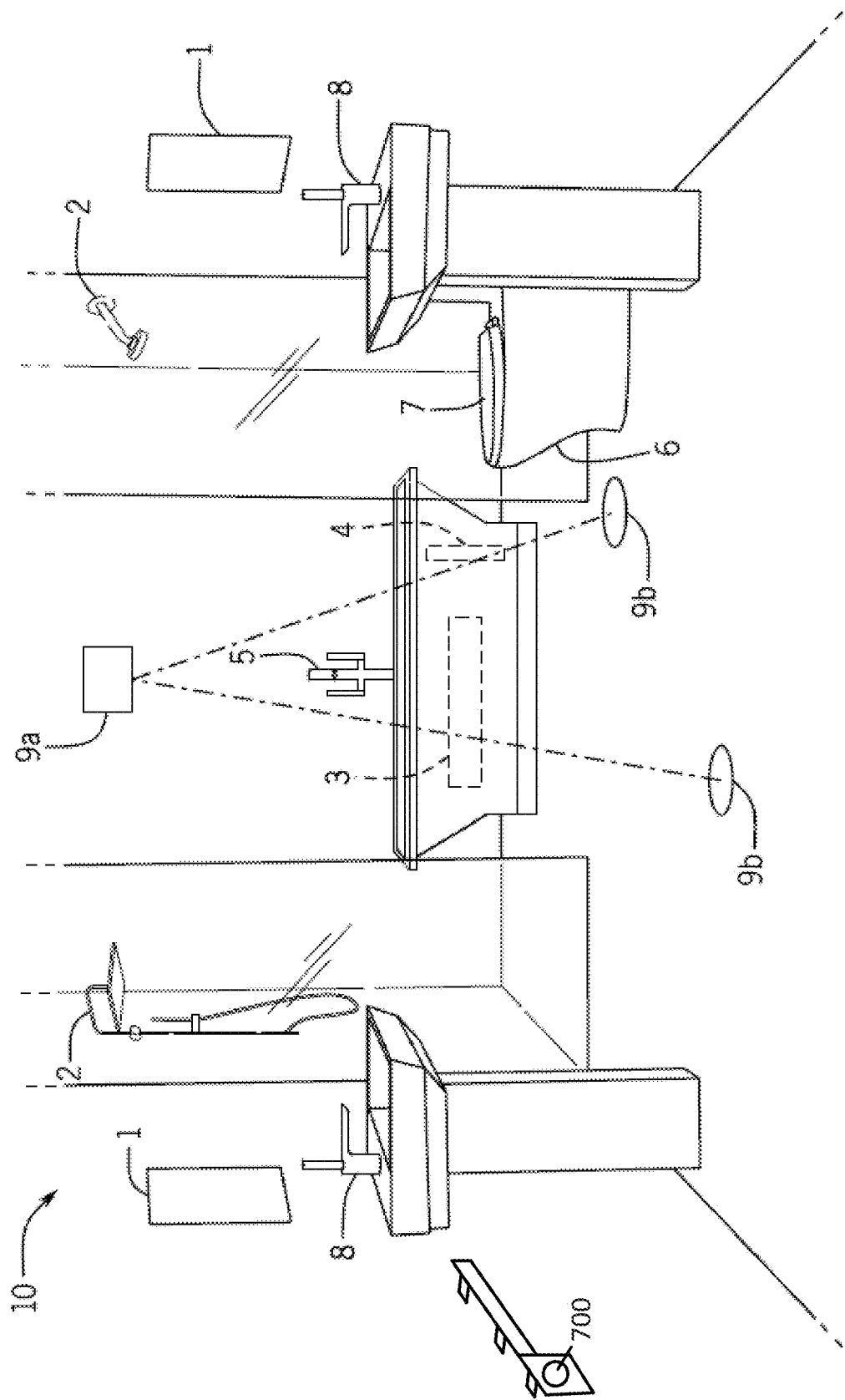
FIG. 1 illustrates a bathroom setting that includes multiple appliances or intelligent bathroom devices connected through at least one home hub communication device, according to an exemplary embodiment.

FIG. 1 illustrates a bathroom setting 10 that includes multiple appliances or intelligent bathroom devices connected through at least one home hub communication device, according to an exemplary embodiment. The intelligent bathroom devices may include one or more of an intelligent mirror 1, a programmable shower 2, a bathtub sensory device 3, a bathtub level device including a drain 4 and faucet 5, an intelligent toilet 6, a toilet seat 7, a sink faucet 8, and light guides including a light source 9a and projected guides 9b. Each of the intelligent bathroom devices is configured to collect data indicative of a user, communicate the data indicative of the user to another intelligent bathroom device either directly or indirectly, and provide services to user based on data indicative of the user that is received from other intelligent bathroom devices.

The intelligent mirror 1 may include a screen or other user interface to provide selections to any of the intelligent bathroom devices or other devices. For example, commands received at the intelligent mirror 1 may be transmitted to any of the other devices (e.g., to turn on, turn off, start a function, or make a selection). Further, the status or other settings of the other devices may be displayed by the intelligent mirror 1.

The programmable shower 2 may provide a shower sequence to the user. The shower sequence may include any combination of a sequence of predetermined intensities for a shower spray, a predetermined sequence of different shower heads, a set of temperatures, or other patterns. The shower sequences may be selected based on an identification of the user as facilitated by another intelligent bathroom device or other devices, data collected by the other devices, or a user selection may through the other devices.

The bathtub sensory device 3 may provide a predetermined (e.g., user defined) pattern of any combination of sound, hydrotherapy, aroma, lighting, and massage. The bathtub sensory device 3 may include speakers integrated with or embedded in the bathtub. The predetermined pattern may be generated or selected based on the identification of the user as facilitated by another intelligent bathroom device or other devices, data collected by the other devices, or a user selection may through the other devices. The status or pattern of the bathtub sensory device 3 may be transmitted to and displayed by the intelligent mirror 1 or other devices.

The bathtub level device, which may include an automated drain 4 and automated faucet 5, may automatically regulate the fill level of the bathtub. The bathtub level device may maintain a predetermined level or depth of the water in the bathtub and maintain a predetermined temperature or range of temperatures of the water. The bathtub automatically monitors changes to water temperature in the bath and adjusts the water temperature coming out from the faucet 5, or other location accordingly. For example, the bathtub can adjust the water temperature coming out of the faucet 5 based on remaining volume that need to be filled to achieve the correct final desired state based on different ambient temperatures. The bathtub predetermined level and predetermined temperatures can be changed to new set values in which case the bathtub dynamically changes its status to achieve the new set values. For maintaining water temperature once the bath is ready (i.e., when the water level is already at its target fill level), a calculated volume of water is drained from the bathtub and added to the bathtub to maintain the temperature as the water is affected by the ambient environment. The fill level that is maintained by the bathtub level device may be based on an identification of the user as facilitated by another intelligent bathroom devices or other device, data collected by the other devices, or a user selection may through the other devices. The change in water level as detected by the level device can be used for identification of the user and can prompt other changes to the lighting 9, music 1, and hydrotherapy accordingly. The status or pattern of the bathtub level device may be transmitted to and displayed by the intelligent mirror 1 or other devices.

The intelligent toilet 6 may provide automatic opening and closing as well as flushing and other sanitation features. The intelligent toilet 6 may provide lid and ring orientations or positions based on an identification of the user as facilitated by another intelligent bathroom device or other devices, data collected by the other devices, or a user selection may through the other devices. The status of the intelligent toilet 6 may be transmitted to and displayed by the intelligent mirror 1 or other devices.

The toilet seat 7 may include a heater that increases the temperature of the toilet seat 7 for comfort of the user. The temperature may be selected based on an identification of the user as facilitated by another intelligent bathroom device or other devices, data collected by the other devices, or a user selection may through the other devices. The toilet seat 7 may collect biometric data or biological characteristics from the user. The status of the toilet seat 7 or conclusions drawn from the data collected at the toilet seat 7 may be transmitted to and displayed by the intelligent mirror 1 or other devices.

The sink faucet 8 may provide a predetermined volume of water, a predetermined temperature of water, or a predetermined flow velocity of water based on an identification of the user as facilitated by another intelligent bathroom device or other devices, data collected by the other devices, or a user selection may through the other devices. The sink faucet 8 may collect data on flow quality, filtration data including particulate data (e.g., mineral level or metal level), or micro-organism data. The status of the sink faucet 8 may be transmitted to and displayed by the intelligent mirror 1 or other devices.

The light guides, including light source 9a and projected guides 9b, may project light on one or more other devices to guide the user to the device or help illuminate the area near the device. In response to a function being selected at one of the devices, user selection data, or a location and/or direction associated with a user selection, is transmitted to the light source 9a to define a direction for projecting the projected light guides 9b. The status of the light guides may be transmitted to and displayed by the intelligent mirror 1. In one alternative, the light guides are implemented as versatile tiles or tech tiles. The versatile tiles may include lights, speakers, sensors, and/or heaters implemented as flooring.

Figure 2:
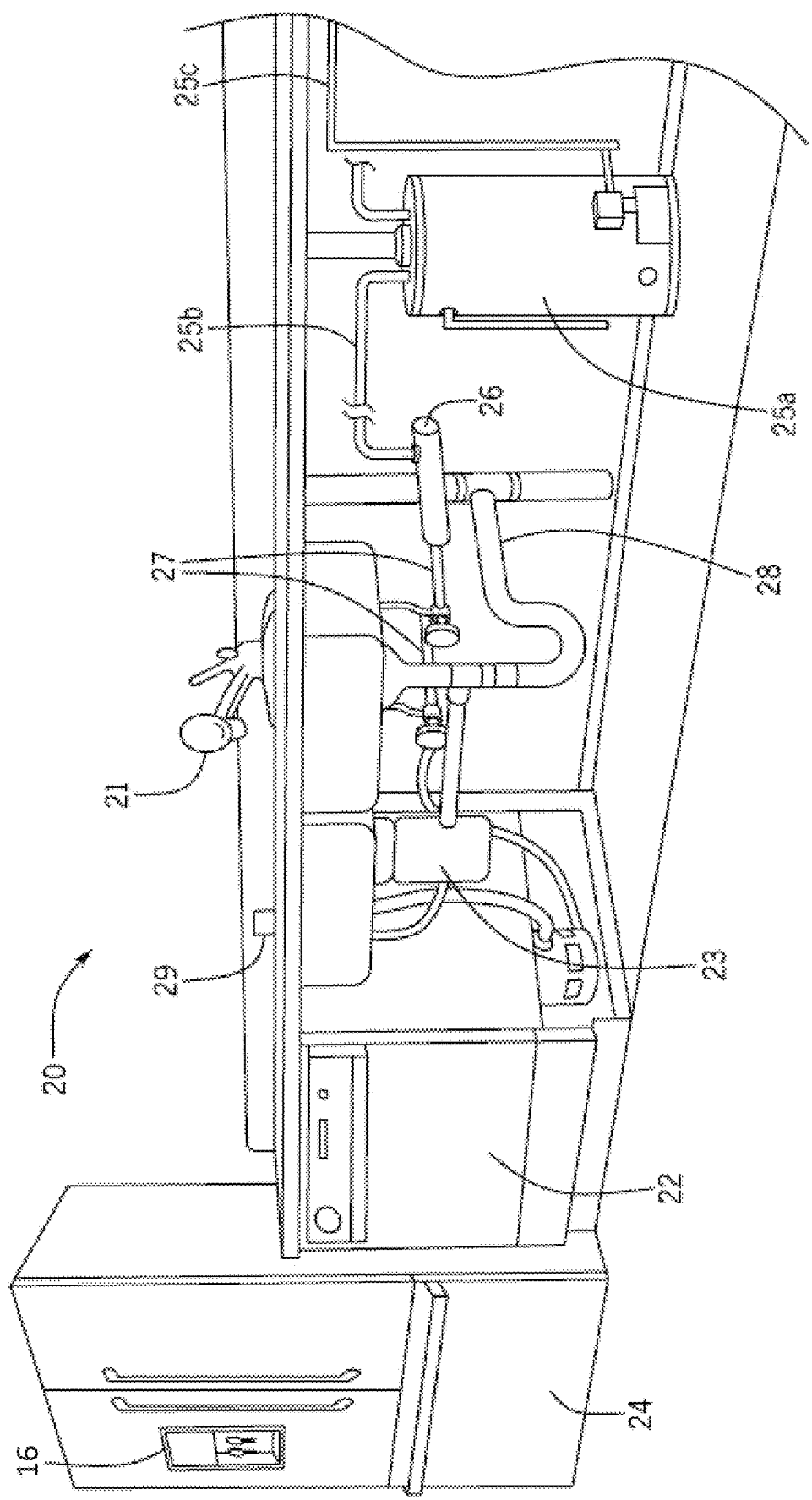
FIG. 2 illustrates a kitchen setting that includes multiple appliances or intelligent kitchen devices connected through at least one home hub communication device, according to an exemplary embodiment.

FIG. 2 illustrates a kitchen setting 20 that includes multiple appliances or intelligent kitchen devices connected through at least one home hub communication device, according to an exemplary embodiment. The intelligent kitchen devices may include one or more of a kitchen faucet 21, a dishwasher 22, a garbage disposal 23, a refrigerator 24, a water heater 25, and a water filter 26. Each of the intelligent kitchen devices may be connected to a water supply 27 and a drain 28. Each of the intelligent kitchen devices is configured to collect data indicative of a user, communicate the data indicative of the user to another intelligent kitchen device either directly or indirectly, and provide services to user based on data indicative of the user that is received from other intelligent kitchen devices.

A control center for the kitchen may be implemented using a display screen. The display screen may be incorporated in one or more of the intelligent kitchen devices. For example, the refrigerator 24 may include a control center with a controller and a display 16. In addition or in the alternative, any of the intelligent kitchen devices may include a similar control center display 16. The control center display 16 may communicate with any of the intelligent kitchen devices to receive commands or data or control the other intelligent kitchen devices.

The kitchen faucet 21 may provide a predetermined volume of water, a predetermined temperature of water, or a predetermined flow velocity of water based on an identification of the user as facilitated by another intelligent bathroom device, kitchen device, or other devices, data collected by the other devices, or a user selection may through the other devices. The status of the kitchen faucet 21 may be transmitted to and displayed by the control center display 16. The kitchen faucet 21 may include a flow sensor configured to measure a flow of water to the kitchen faucet 21, which is transmitted to the control center controller.

The dishwasher 22 may provide various washing cycles for washing dishes. The washing cycle may include a predetermined pattern of washing cycles, a predetermined type of washing pattern (e.g., gentle cycle, pots and pans, sanitize, extra heat, steam), a temperature setting, a turbidity setting, a water volume setting, or another setting. The status of the dishwasher 22 may be transmitted to and displayed by the control center display 16. The dishwasher 22 may include a flow sensor configured to measure a flow of water to the dishwasher 22, which is transmitted to the control center controller.

The garbage disposal 23 may include a garburator or cutting blades for cutting food wastes or other material into small pieces for passing through plumbing. The garbage disposal 23 may be mounted in line between the drain of the sink and the trap of the plumbing. The garbage disposal 23 may include a timing setting for an amount of time for the garbage disposal 23 to run. The garbage disposal 23 may include a quiet mode that runs at lower speed. Data collected or generated by the garbage disposal 23 may be transmitted to and displayed by the control center display 16. The garbage disposal 23 may include a flow sensor to measure the flow of particulate out of the garbage disposal 23.

The refrigerator 24 may include a refrigerator compartment that provide refrigerated storage for food and/or a freezer compartment that provides low temperature storage for food. The refrigerator 24 may include multiple temperature settings, child safety settings, and a status including the time and temperature. The freezer compartment of the refrigerator 24 may include a temperature setting and an icemaker mode for controlling the type of ice produced by the icemaker. In addition to these settings and statuses, the control center display 16 may provide settings and data from any of the other intelligent kitchen devices or intelligent bathroom devices. The refrigerator 24 may include a flow sensor configured to measure a flow of water to the refrigerator 24 (e.g., for example for a water dispenser or icemaker), which is transmitted to the control center controller.

The water heater 25 (including tank 25a, water supply 25b, and optionally fuel supply 25c) may provide heated water to the other appliances. The water heater 25 may include a temperature setting that describes the target temperature for the water in the water heater. The water heater 25 may include a volume setting that defines an amount of water that is heated in the water heater 25. The status of the water heater 25 may be transmitted to and displayed by the control center display 16. The water heater 25 may include a flow sensor configured to measure a flow of water in or out of the water heater 25, which is transmitted to the control center controller.

The water filter 26 may filter water before the water is provided to any of the other kitchen devices. The water filter 26 may include various settings including filtering modes that target particular contaminants. For example, the water filer 26 may include a lead filtering mode which may target removing lead from the water, a bacteria filtering mode which may target removing bacteria from the water, or specific particulate filtering mode for removing a specific particulate from the water. The status of the water filter 26 may be transmitted to and displayed by the control center display 16. The water filter 26 may include a flow sensor configured to measure a flow of water in or out of the water filter 26, which is transmitted to the control center controller.

Each of the intelligent kitchen devices is discussed in more detail below. The at least one home hub communication device may be an independent device or integrated with any of the appliances. In one example a home hub communication device 29 may be integrated with a counter (e.g., retractable to move below or above the counter surface). Additional, different or fewer components may be included.

Any of the intelligent bathroom devices may interact with any of the kitchen devices. For example, data collected at one or more bathroom devices may be analyzed to determine a command, a setting, or a display at one or more of the kitchen devices, and vice versa. For example, the identity of a user at a bathroom device may be sent to a kitchen device for accessing configuration or preferences for the user upon approaching the kitchen device.

Communication Network

Figure 3:
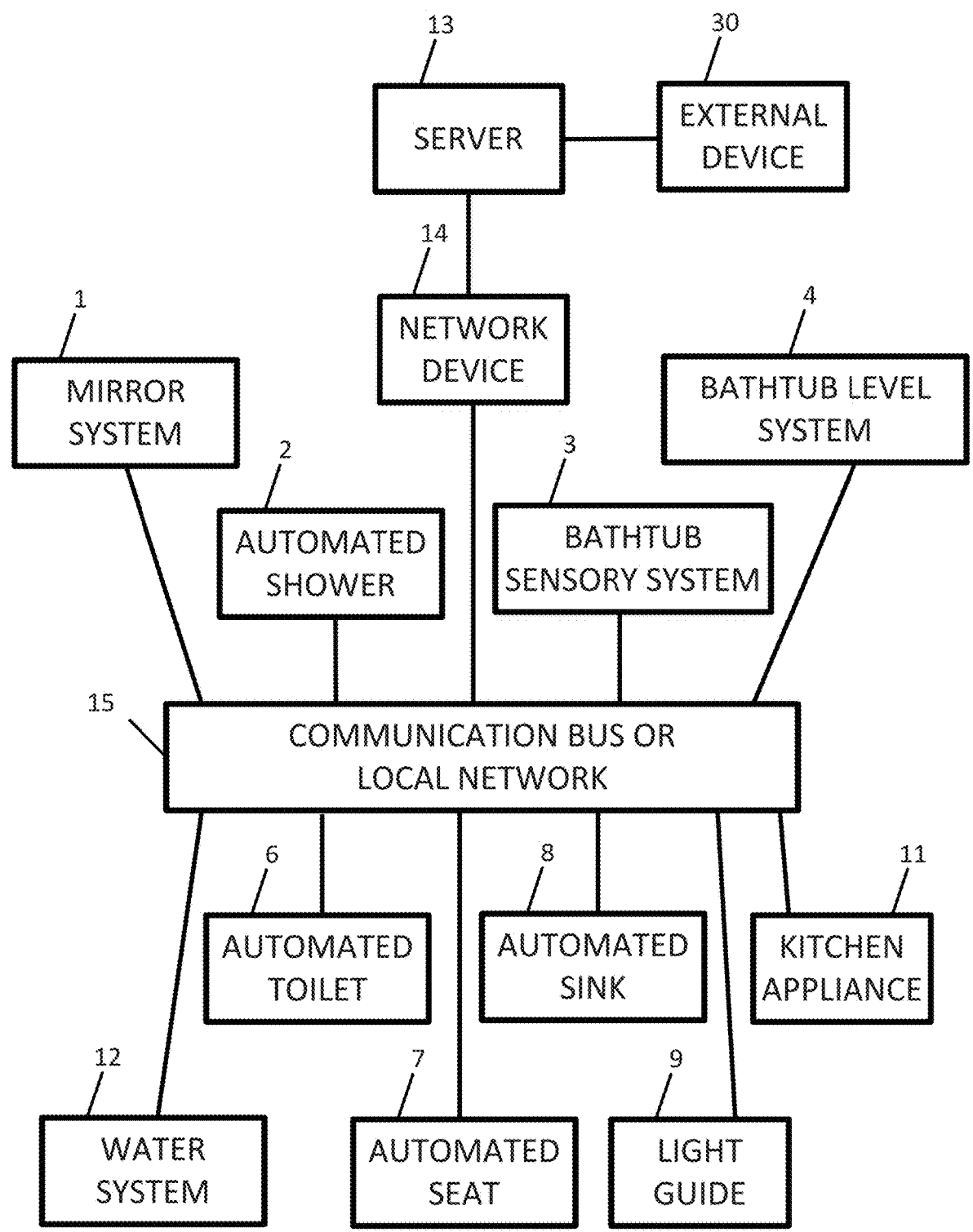
FIG. 3 illustrates a communication network for the sets of appliances of FIG. 1 and/or FIG. 2, according to an exemplary embodiment.

FIG. 3 illustrates a communication network for the example sets of appliances of FIG. 1 and/or FIG. 2. The communication network may include a server 13, a network device 14, and a communication bus or local network 15. The communication bus or local network 15 may be connected to one or more of any combination of the intelligent mirror (mirror assembly) 1, the programmable (automated) shower 2, the bathtub sensory device 3, the bathtub level device including the drain 4 and faucet 5, the intelligent (automated) toilet 6, the toilet (automated) seat 7, the sink faucet (automated sink) 8, light source 9a and light guides 9b, a kitchen appliance 11, and a water system 12. Additional, different, or fewer components may be included.

The server 13 may be a cloud device configured to communicate with multiple network devices 14 located in multiple locations (e.g., different homes or businesses). The server 13 may implement a cloud service that coordinates and analyzes data from the multiple network devices 14 affiliates with multiple appliances.

The network device 14 may be a standalone device (e.g., having a dedicated power supply, speaker, and/or microphone) as a home hub communication device. Alternatively, the network device 14 may be integrated with one or more of the appliances.

In one example, the analysis of data occurs primarily at the network device 14, which may be referred to as the local analysis embodiments. In another example, the analysis of data occurs primarily at the server 13 or another remote device, which may be referred to as the remote analysis embodiments. Hybrid embodiments may include a combination of data analysis at the network device 14 and the server 13.

Regarding the local analysis embodiments, the network device 14 receives data collected at appliance X and performs an analysis of the data to generate a command for appliance Y. The analysis may include determining an identity of the user of appliance X, a temporary state of the user of appliance X, or a command from the user of appliance X. An example identity of the user may include an identifier for the user (e.g., username, user number, user code). An example temporary state of the user may include drowsiness, complexion, sickness, or mood. An example command from the user may turn on appliance Y or change a setting for appliance Y.

Regarding the remote analysis embodiments, the network device 14 may package or pre-process the data in a predetermined format and transmit the data to the server 13. The network device 14 may filter the data according to type. Example types include audio data, image data, position data, biometric data, ambient data, or other types. The network device 14 may select a particular type of data to send to the server 13 based on the types of appliances associated with the network device 14. That is, the network device 14 may sort and select data collected at appliance X, for use with appliance Y, according to the capabilities or configuration of appliance Y, and send the selected data to server 13. In turn, the server 13 sends the selected data to appliance Y in response to the capabilities or configuration of appliance Y.

For image data, the network device 14 may analyze an image of at least a portion of the user. For position data, the network device 14 may determine a position of the user through analysis of the image (e.g., pattern matching or line detection) or through distance based sensors based on proximity. For biometric data, the network device 14 may collect temperature data (e.g., heat signature) from a temperature sensor or infrared sensor, fingerprint data from a fingerprint sensor, or eye data from a retina scanner. For ambient data, the network device 14 may collect temperature, humidity, or other environmental information.

The network device 14 may package the data in a predetermined format and transmit the data to the server 13. The predetermined format may be specific to the type of data (e.g., a particular file format). In one example, the collected data includes voice commands and the predetermined format is an audio file. The predetermined format may be an audio encoding format (e.g., Moving Picture Experts Group (MPEG) standard, MPEG-2, mp3, wave file or other format).

In addition to being encoded in a particular audio format, the recorded audio may include a predetermined syntax. The voice commands may include any combination of summons commands, request commands, device function commands, a skill command, and other commands.

The summons command may include a trigger word or voxel to address the home hub communication device. The trigger word may include a user specified name for the home hub communication device or a brand name for the home hub communication device or a generic name (e.g., hub or home hub) for the home hub communication device. In another example, the trigger word may include a class of appliance or an associated room for the appliance. The skill command may include device identifiers and device functions. The device identifier includes a code or a word that describes the target device for the skill command. An example predetermined syntax for the voice command may be [summons] [skill] or [summons] [device identifier] [device function]. An example predetermined syntax for the voice command that specifies the brand of the appliance may be [summons] [brand] [skill] or [summons] [brand] [device identifier] [device function]. An example predetermined syntax for the voice command that specifies the class of the appliance may be [summons] [bathroom] [skill] or [summons] [bathroom] [device identifier] [device function].

The device identifier may include multiple components. The device identifier may include a component identifier and a sub-component identifier. The component identifier may describe any of the appliances described herein. The sub-component identifier may describe a portion of the appliances. For example, for the component of a shower, each shower sprayer is a sub-component, and for the component of a sink, the hot and cold water valves may be a sub-component. The device function command may be a command to apply to the component and/or the sub-component. For example, for the component of a shower and shower sprayer a sub-component, the device function may include a level setting for the shower sprayer, and for the component of a sink, the device function may be the temperature defining a combination of the hot and cold levels.

In one example, the summons command is omitted. For example, the predetermined format for the home hub communication device or the network device 14 may include a one-word theme control to communicate from one appliance to another appliance. For example, when the intelligent mirror 1 receives a word indicative of a local appliance (e.g., lighting, temperature, sound, etc.) the following words are applied directly to that local appliance.

The appliances may also be arranged in scenes, groups, and routines. A scene is a collection of devices that respond differently to a single command. An example scene may be "good morning" that causes the fan to turn on, the shower to start at a set temperature, and the lights to turn on. Another example scene may be "lights on" that causes the ceiling lights to turn on as well as the light on the mirror. A group is a collection of devices that respond in a similar fashion to one or more commands. An example group of devices may be all the lights. Another example group of devices is the door locks in the home. The group may be triggered to turn on all of the lights or lock all of the doors. A routine is a time sequence that of events that is applied to one or more appliances. For example, the shower may be started and then, after a first predetermined time period (e.g., two minutes) after the shower is started, the lights at the mirror are turned on, after a second predetermined time period (e.g., 10 minutes), the intensity, brightness, or color temperature is of the light is changed.

Another example predetermined syntax for the voice command may be [scene], which may access a scene access table to convert the scene to multiple full commands (e.g., [summons] [skill] or [summons] [device identifier] [device function]). Another example predetermined syntax for the voice command may be [group] [device function], which may access a scene access table to convert the scene to multiple full commands (e.g., [summons] [skill] or [summons] [device identifier] [device function]). Another example predetermined syntax for the voice command may be [routine], which may access a scene access table to convert the scene to a sequence of full commands (e.g., [summons] [skill1] or [summons] [device identifier1] [device function1], [delay], [summons] [skill2] or [summons] [device identifier2] [device function2]).

The appliances may communicate using a master and slave model. The master device may be defined as the device that directly communicates with the server 13 and receives voice commands from the user, and the slave device may be defined as the device that receives instructions from the server 13 in response to the voice commands router to the server 13 through the master device. In some embodiments, the network device 14 is the master device and one or more of the appliances are slave devices.

In another example, the network device 14 is omitted, or otherwise provides only network functionality, and one of the appliances operates as the master devices while one or more other of the appliances operates as the slave device. The appliances may be configured to perform a priority order algorithm for determining which of the appliances are designated as master devices and which of the appliances are designated as slave devices. The priority order algorithm may be based on one or more priority techniques including order of connection, order of installation, order of user preference, order of manufacturer preferences, and/or user proximity preference.

The order of connection may indicate the first appliance that connects to the network device 14 or server 13. The network device 14 or the server 13 may assign master status or slave status to the appliances upon connection to the network. For example, when an appliance connects to the network, the appliance may send a connection request to the network device 14 or server 13. The connection request may include a device identifier for the appliance and/or a list of device functions compatible with the appliance. In response to the connection request, the network device 14 or the server 13 may return a status such as a slave status or a master status to the appliance. For the order of connection technique, when the connection request is the first connection request or only active connection request, the network device 14 or server 13 return a master status to the appliance. When the connection request is not the first connection request or not the only active connection request (i.e., another active connection exists), the network device 14 or server 13 may return a slave status to the appliance. The appliance follows a master mode in response to the master status or a slave mode in response to the slave mode.

In another example for the order of connection technique, the network device 14 or the server 13 may assign master status or slave status to the appliances based on internet protocol (IP) address. On the network, dynamic IP addresses may be assigned in numeric sequence according to the order that the appliances connect to the network. The network device 14 or the server 13 may receive a connection request from an appliance and the connection request may include the IP address for the appliance. The network device 14 or the server 13 may analyze the IP address and return a master status or a slave status to the appliance in response to the analysis of the IP address. In one example, the network device 14 or the server 13 may store the received IP addresses in memory and compare the received IP addresses. The network device 14 or the server 13 may assign the master status to the lowest IP address and the slave status to other IP addresses. In another example, the network device 14 or the server 13 may assign the master status or the slave status to a predetermined IP address. The assignment of IP addresses to the master or slave status may be defined according to user input or an external device.

The order of installation technique may designate the first appliance to be installed or powered on as the master device. The network device 14 or the server 13 may determine the first appliance to be installed or powered on based on a wireless communication (e.g., Bluetooth broadcast). The individual appliances may record a local timestamp for the time that the appliance is installed or powered on. The network device 14 or the server 13 may determine the first appliance to be installed or powered on a connection request from an appliance when the connection request includes the timestamp stored by the appliance.

The order of user preference may be set by a user input or a default order. The order of user preference may specify individual appliances. For example, the order of preference may specify the intelligent mirror, intelligent toilet, intelligent shower, light guides or other devices. Any order of appliances is possible. The order of user preference may specify types of appliances. For example, the order of types of appliances may specify bathroom appliances then kitchen appliances, or the order of types of appliances may specify appliances with user interfaces (e.g., intelligent mirror), appliances with mobile device control (e.g., intelligent toilet), appliances without user interfaces (e.g., automatic leveling bathtub), and passive appliances (e.g., light guides and versatile tiles). Within each hierarchy in the order, a second ordering technique may be used. For example, among the user appliances with user interfaces, the second order may specify the order the appliances were connected to the network.

The order of manufacturer preference may be an order of devices specified by the manufacturer. Each appliance may store an alphanumeric code (e.g., A, 1, or another code) that indicates the order. The appliance may send a connection request to the network device 14 or the server 13 including the alphanumeric code for ordering. The network device 14 or the server 13 may order the codes received from multiple devices. The highest code may be designated master status and other codes may be designated slave status.

The user proximity technique may dynamically change the master and slave status according to the presence of the user. For example, as each appliance detects the proximity of the user through a proximity sensor or another type of sensor, the appliance may report the proximity to the network device 14 or the server 13. The network device 14 or the server 13 may assign a master status to the appliance with the closest proximity to the user. Other devices may be assigned a slave status. The master status changes dynamically. As the user moves from one device to another, the master status is updated. For example, when the user moves from near appliance X to near appliance Y, the network device 14 or the server 13 may change the status of appliance X from master to slave and change the status of appliance Y from slave to master.

In the master mode, one appliance can be configured to lead a group of appliances. The master device may be the only device that receives audio commands from the user. Audio commands at other appliances in the slave mode may be ignored. The master mode may enable a microphone of the appliance, and the slave mode may disable a microphone of the appliance. An appliance in master mode may issue instructions to other appliances in slave mode.

In addition to exchanging information with each other, the appliances may exchange information with an external device 30 through the network device 14 and or the server 13. The external device 30 may be associated with a manufacturer (e.g., the appliance manufacturer), an insurance provider, a utility provider or another entity.

The external device 30 may be configured to compile and analyze data connected by the appliances and shared through the network device 14 and the server 13. In one example, the network device 14 generates a report in response to the feedback data, and sends the report to the external device 30. The external device 30 may provide the user with service benefits in exchange for the shared data. The external device 30 may compile feedback data for multiple types of appliances and/or multiple locations for the appliances. The external device 30 may store the feedback data in association with the geographic locations of the appliances that collected the feedback data. The compiled data or the report may be indicative of geographically related events such as water containments, illnesses, or pollution.

The manufacturer, using the external device 30, may collect data related to usage, maintenance, or malfunction. The usage data describes when the user uses the appliance (e.g., a time of day or day of the week) and how the user uses the appliance (e.g., the shower door is closed, the water faucet is turned on). The external device 30 may calculate from the usage data how often and the duration a particular feature of an appliance is used. For example, for the toilet, the external device 30 may determine a number of seated users and a number of standing users. Features may be added or removed from a device based on the usage data. The maintenance data may describe when maintenance is applied to the appliance such as a consumable is replaced (e.g., water filter, seal, disinfectant solution) or when a maintenance provider visits the appliance. The malfunction data may include errors that are logged by the appliance. Errors may include electronic errors with the controller, water leaks or other plumbing errors, or communication errors with the network. The external device 30 may provide alerts to the user based on the collected data. Example alerts based on maintenance data may describe when a consumable should be reordered. The network device 14 may automatically reorder the consumable.

The network device 14 (e.g., a home hub communication device or appliance with integrated a home hub communication device) including a speaker and the external device 30 may coordinate to provide service assistance to the user. After diagnostics are performed at the external device 30 based on data collected at the appliances, the external device 30 provides feedback to the network device 14 in the form of announcement of a service call and/or scheduling, do-it-yourself instructions for the user to perform maintenance on the appliance, or error codes for the user to apply to the appliance or provide to a technician. The external device 30 may also send appropriate diagnostic routines, software upgrades, firmware upgrades or other local settings to the network device 14.

The insurance provider, through the external device 30, may collect data related to user habits. Example habits include frequency of sanitary actions such as washing hands, or frequency of risk taking actions such as showering. The utility provider may collect data related to water usage at the appliances at different times of day in order to price water costs at different levels during the day. The pricing scheme may encourage water to be used more evenly throughout the day, which improves overall water conservation.

A collection of all the settings for the one or more of the appliances may be stored by the network device 14 or the server 13. The collection of settings may be a user passport that is transferrable to different locations through the server 13 (e.g., transferred to external device 30). The different locations may be different houses, hotels, or other rooms. In other words, the collection of settings for the appliances in FIG. 1 and/or FIG. 2 may be saved and stored in association with the user. When the user travels to another location such as a hotel room, the settings are provided on appliances at the other location. The external device 30 may access the user passport based on user identity such as a credit card, communication with the user's phone, a detection of the user's entity, or a code directly entered at the other location.

Appliance Coordination

Figure 4:
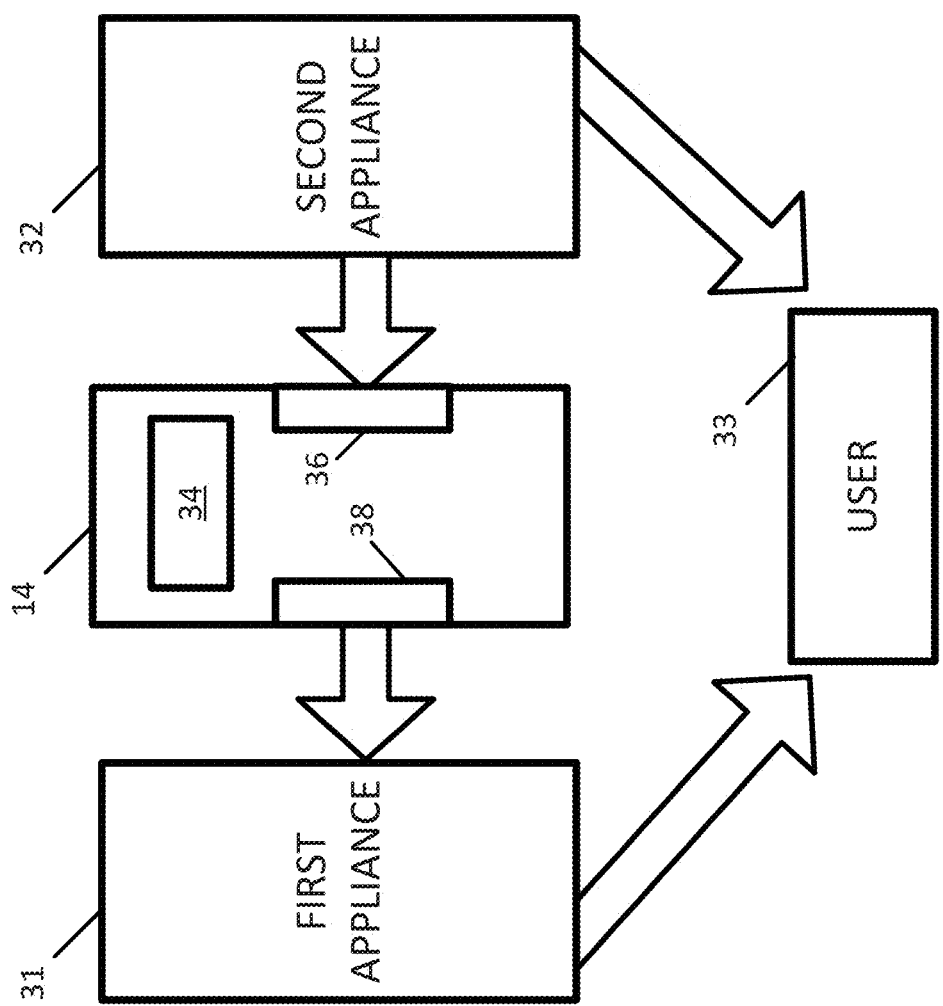
FIG. 4 illustrates a flow of data between appliances for providing services to a user, according to an exemplary embodiment.

FIG. 4 illustrates a flow of data between appliances for providing services to a user, according to an exemplary embodiment. A network device 14 communicates with a first appliance 31 and a second appliance 32. The first appliance 31 may provide services to the user 33 based on data collected at the second appliance 32, or vice versa. Additional, different, or fewer components may be included.

The network device 14 may include a data collection interface 36, a controller 34, and an output interface 38. The data collection interface 36 and/or the output interface 38 may be configured to communicate with the first appliance 31 and/or the second appliance 32 using a wireless network or a personal area network. Example wireless networks include cellular networks, the family of protocols known as Wi-Fi or IEEE 802.11, the family of protocols known as Bluetooth, or another protocol. The cellular technologies may be analog advanced mobile phone system (AMPS), the global system for mobile communication (GSM), third generation partnership project (3GPP), code division multiple access (CDMA), personal handy-phone system (PHS), and 4G or long term evolution (LTE) standards, or another protocol. Example wireless networks may include a wireless mesh network (e.g., Bluetooth mesh). The wireless mesh network many include may to many communication. For example, the appliances of FIG. 1 and/or FIG. 2 may be directly connected to form a mesh network. Example personal area networks may include the family of protocols known as Bluetooth low energy or another low energy protocol configured to maintain a predetermined distance range under a predetermined power consumption level. The wireless mesh network may include one or more nodes for appliances using Bluetooth low energy.

In one implementation, the network device 14 communicates with at least one water consuming device. Example water consuming devices include the programmable shower 2, the bathtub sensory device 3, the bathtub level device including the drain 4 and faucet 5, the intelligent toilet 6, the automated sink 8, the kitchen appliance 11, and the water system 12. The water consuming device is connected to a water supply or plumbing system. The water consuming device may include at least one sensor associated with the water supply such as a flow sensor that measures the flow of water or other types of sensors.

The data collection interface 36 is configured to receive user data from at least one water consuming device (e.g., the first appliance 31 and/or the second appliance 32). While only unidirectional communication is illustrated in FIG. 4, the data collection interface 36 may connect with both the first appliance 31 and the second appliance 32 for bidirectional communication. The user data may describe sensor data collected at the first appliance 31 and/or the second appliance 32, entry data entered by the user at the first appliance 31 and/or the second appliance 32, logged data recorded at the first appliance 31 and/or the second appliance 32, or configuration data accessed the first appliance 31 and/or the second appliance 32.

The sensor data, or user data, is collected at the first appliance 31 and/or the second appliance 32. The sensor data may describe the spatial position of the user. For example, the sensor data may be collected by a motion sensor or a proximity sensor. The sensor data may include three-dimensional coordinates of the spatial position of the user of a portion of the user (e.g., feet, hands, or body). The sensor data may be collected by an eye gaze sensor that determines a line of sight or angular orientation of the face of the user. The sensor data may describe a gesture or movement made by the user. Example, gestures include pointing handwaving, or directional movements such as raising or lowering a hand to change a setting. The sensor data may include an infrared or laser scan of the area near the first appliance 31 and/or the second appliance 32.

The sensor data may be collected by a camera or image collection device. The sensor data may be analyzed using an image processing technique to determine the color, brightness, or hue of the user. Alternatively, the image processing technique may determine the size, shape, gender, age, or other demographic data for the user. The sensor data may describe the state of the body of the user using another characteristic such as heart rate, temperature, the presence of sweat, or odor.

The entry data can be entered by the user at the first appliance 31 and/or the second appliance 32. The entry data may include login data or login credentials (e.g., a username and certifying information). The entry data may include a selection for operating the first appliances 31. The entry data for operating the first appliance 31 may be used to operate the second appliance 32. For example, a temperature setting for the automated shower 2 may be indicative of user preferences and used to determine a temperature setting for the automated sink 8.

The logged data can be recorded at the first appliance 31 and/or the second appliance 32. The logged data may describe the habits of the users over time. The logged data may include device settings associated with time stamps. The network device 14 may analyze the logged data to identify trends in the historical data. For example, a temperature setting may tend to be warmer in winter months and lower in summer months. The network device 14 may calculate a season factor for adjusting the temperature setting at the second appliance 32 based on historical data collected at the first appliance 31.

The configuration data accessed the first appliance 31 and/or the second appliance 32 may relate to particular features of the appliance. For example, a particular user may use a mute setting to disable a speaker of the first appliance 31. The network device 14 may identify the mute setting from the first appliance 31 and send a mute command to the second appliance 32 based on the user's preference.

The user data from the collection device may describe a condition of the user. Example conditions of the user includes a temperature, a heart rate, a height, a weight, a drowsiness, a complexion, a malnutrition, a hydration, or other conditions.

The user data may be modified by the data collection interface 36 or the controller 34. The user data may be filtered to remove noise. A hysteresis control algorithm may be applied to the user data. A first threshold may be applied to increasing data and a second threshold may be applied to decreasing data to prevent rapid threshold crossings from being present in the user data. The user data may be averaged over a predetermined time period to reduce the effects of outlier data points.

The controller 34 is configured to perform an analysis of the user data from the at least one collection device. The analysis may compare the user data to a threshold or profile that is indicative of a device function. When the data is greater than the threshold level or matches a predetermined portion of the profile, the controller 34 generates feedback data for another device.

The controller 34 may average user settings or preferences for one or more features of the at least one collection device and save the average as the feedback data. The averaged preference for one or more features of the at least one collection device may include a temperature setting, a volume of water, a light intensity, or a light direction. For example, when the collection device is a shower, the controller 34 may average the temperature settings by all users or multiple instances of a single user to calculate a temperature for the feedback data.

The output interface 38 is configured to provide feedback data based on the analysis of the user data to the first appliance 31. The feedback data may be applied by the water consuming appliance to set a water temperature, a water volume, or a water pattern in response to the feedback data.

The feedback data may activate or deactivate the first appliance 31 or a particular function of the first appliance 31.

Figure 5:
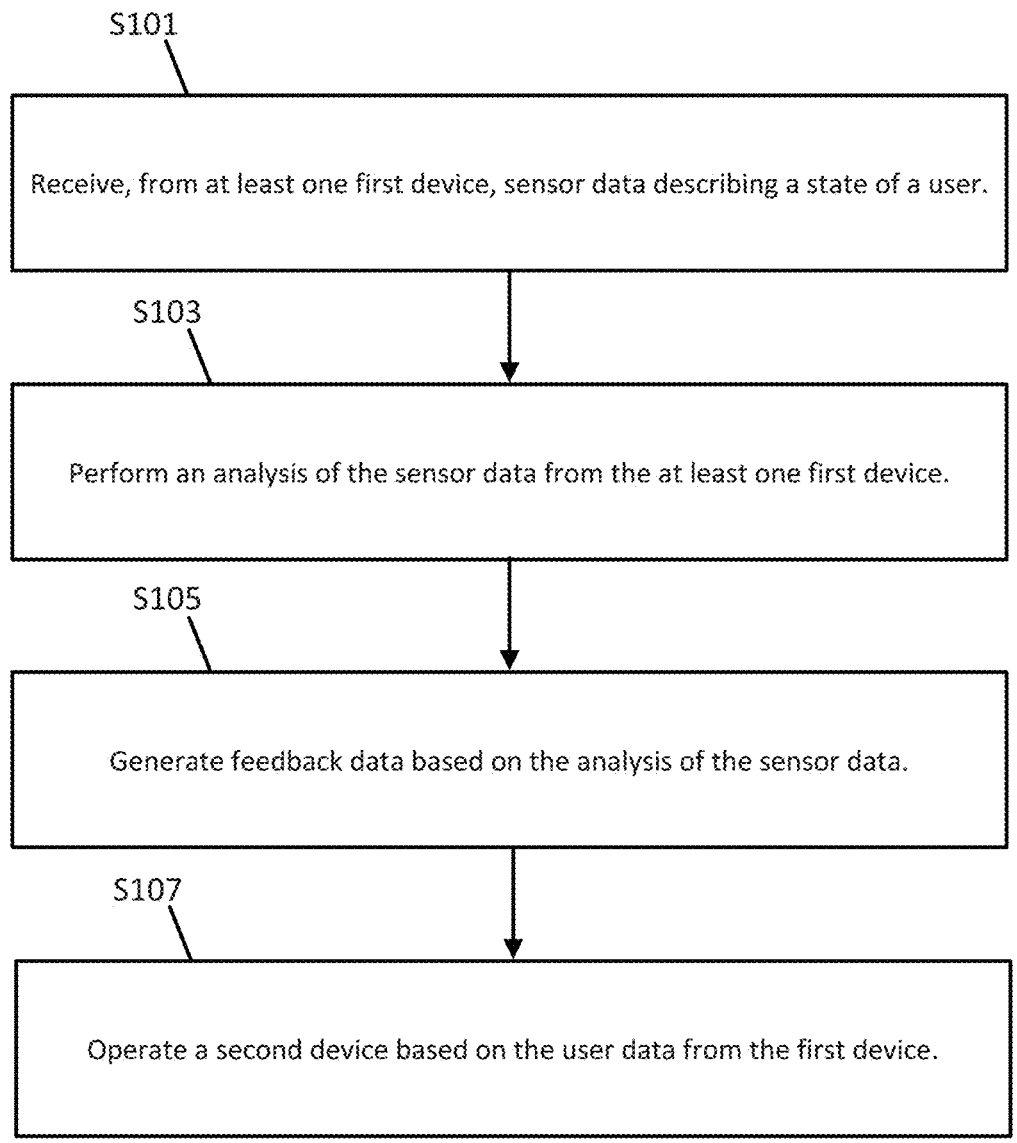
FIG. 5 is a flow chart for operating at least one water consuming device, according to an exemplary embodiment.

FIG. 5 illustrates a flow chart for a method for coordination of household devices, according to an exemplary embodiment. The method may be performed by the network device 14, or specific aspects of the method may be performed by the data collection interface 36, the controller 34, and the output interface 38, respectively. Additional, different, or fewer acts may be included.

At act S101, the data collection interface 36 receives sensor data from at least one first device, the sensor data describing a state of a user. The at least one first device may be a water consuming device (e.g., bathtub, sink, shower, toilet). The state of the user may be the presence of the user, the position of the user, or a measured characteristic of the user.

At act S103, the controller 34 performs an analysis of the sensor data from the at least one first device. At act S105, the controller 34 generates feedback data based on the analysis of the sensor data. The feedback data may include an instruction to operate a second device or a particular device function. When the state of the user is the presence of the user, the analysis may include comparing the presence or absence of the user to a lookup table that lists device functions that are activated when the user is present. Example device functions that are activated when the user is present may include a light, a microphone, or a heater. When the state of the user is the presence of the user, the analysis may include comparing the position to a lookup table that lists device functions that are activated when the user is at certain positions. Example device functions that are activated based on position may include turning on the water when the user is at the sink, flushing a toilet when the user is positioned away from the toilet, or turning on a light based on the position of the user. When the state of the user is a measured characteristic (e.g., temperature, color, or mood), the analysis may include comparing the measured characteristic to a lookup table for the measured characteristic.

At act S107, a second device is operated using the feedback data based on the user data from the at least one first device. The second device may be operated in response to instructions issued by the controller 34. The second device may be a water consuming device (e.g., bathtub, sink, shower, toilet).

Figure 6:
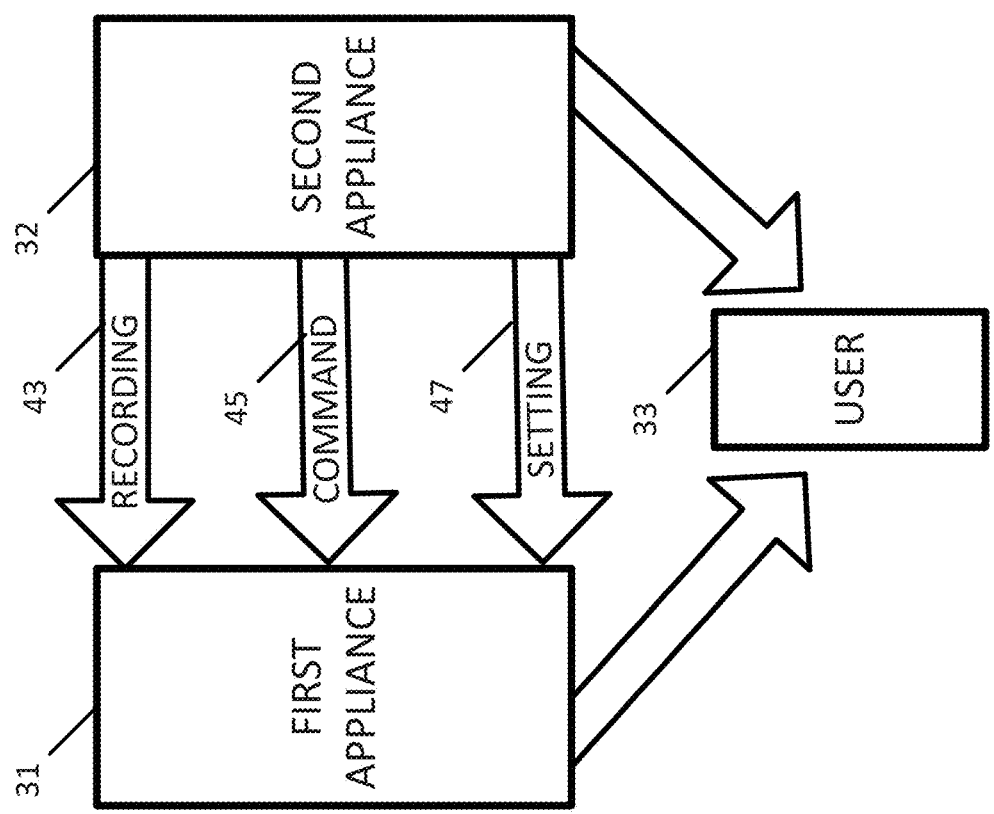
FIG. 6 illustrates a flow of data between appliances for controlling a first device based on data collected by a second device, according to an exemplary embodiment.

FIG. 6 illustrates a flow of data between appliances for controlling a first device based on data collected by a second device, according to an exemplary embodiment. The network device 41 described with respect to FIG. 4 may be included or omitted from the example of FIG. 6. The flow of data between appliances may include multiple types of data including but not limited to an audio recording 43, command data 45, and a setting 47.

The recording 43 may include audio data including a voice command. Example voice commands may include any combination of summons commands, request commands, device function commands, a skill command, and other commands. The voice command may include a predetermined syntax (e.g., [summons], [device function command]). The voice command may include natural language. The recording 43 may be interpreted at the first appliance 31, server 13, or at the network device 14. Alternatively, the voice command may be interpreted at the second appliance 32 and encoded as command data 45. The command data 45 may include a data packet with a device identifier and a function identifier. In addition, the user may directly enter an instruction to the second appliance 32 that is to be applied to the first appliance 31. The direct command may be transferred between appliances as setting 47.

Figure 7:
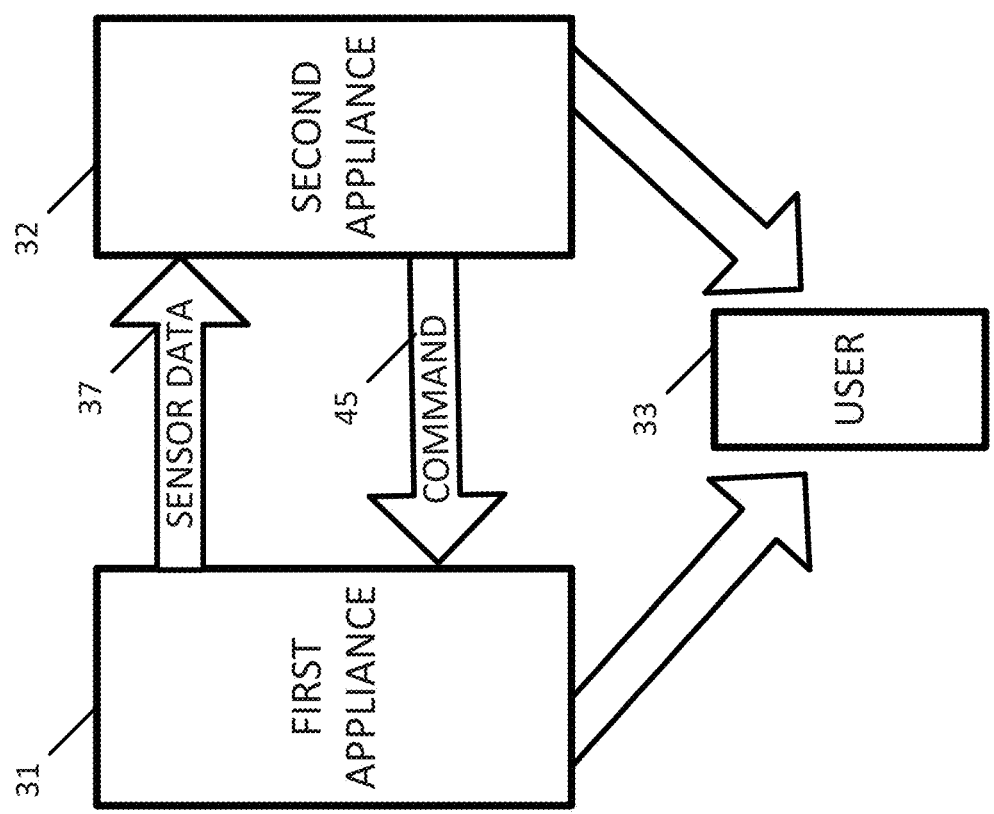
FIG. 7 illustrates bidirectional flow of data between appliances, according to an exemplary embodiment.

FIG. 7 illustrates bidirectional flow of data between appliances, according to an exemplary embodiment. The network device 14 described with respect to FIG. 4 may be included or omitted from the example of FIG. 6. The flow of data between appliances may include multiple types of data including but not limited to sensor data 37 and command data 45. The first appliance 31 collects sensor data 37 and sends the sensor data 37 directly to the second appliance 32, or indirectly through the network device 14 and/or the server 13. The second appliance 32 analyzes the sensor data 37 collected at the first appliance 31 and sends command data 45 directly to the first appliance 31, or indirectly through the network device 14 and/or the server 13.

User Identification

Figure 8:
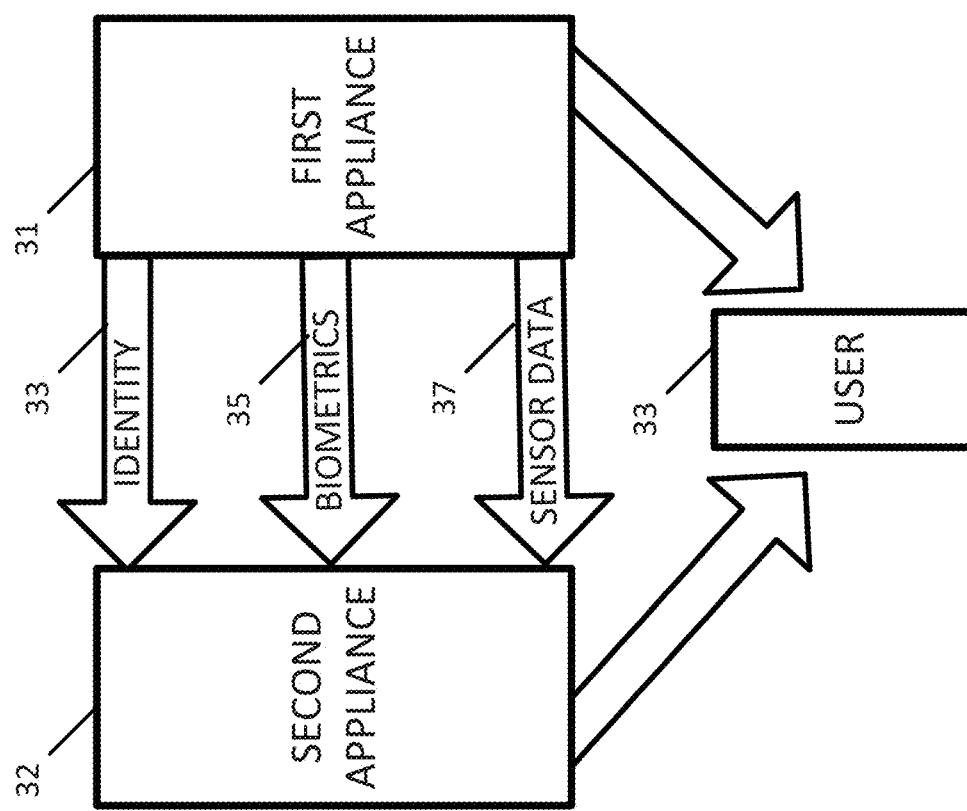
FIG. 8 illustrates another bidirectional flow of data between appliances, according to an exemplary embodiment.

FIG. 8 illustrates another flow of data between appliances for user identification, according to an exemplary embodiment. The network device 14 communicates with the first appliance 31 and the second appliance 32. The first appliance 31 may provide services to the user 33 based on data collected at the second appliance 32, or vice versa. Additional, different, or fewer components may be included.

The first appliance 31 is configured to collect sensor data associated with an identity of a user. The sensor data associated with the identity of the user may include identity data 19, biometric data 35, or sensor data 37. The identity data 39 may include a username or other identifier for the identity of the user of the first appliance 31. The identity data 39 may be derived from image data or proximity data that describes the user. The biometric data 35 may include a body profile, a fingerprint, facial recognition, or other data. The sensor data 37 may include temperature, stress, blood pressure, wakefulness, or other transient characteristics.

The second appliance 32 may access a configuration for the user based on the user identity determined from the sensor data collected by the first appliance. The device function is then defined according to the configuration for the user. The configuration for the user includes a height for the device function, a temperature for the device function, a time delay for the device function, a volume for the device function, or a sequence for the device function, or other settings.

The server 13 or the network device 14 analyzes the sensor data to determine the identity of the user. The second appliance 32 is configured to provide a device function to the user based on identity determined from the sensor data collected by the first appliance. Additional appliances may be connected as well. For example, a third appliance may be configured to provide a device function to the user based on identity determined from the sensor data collected by the first appliance. In any of the bathroom appliances described with respect to FIG. 1, the kitchen appliances described with respect to FIG. 2, or other appliances may be the first appliance 31 or the second appliance 32. In another implementation, the first appliance 31 or the second appliance 32 is a bathroom appliance connected to plumbing or the water system. In another implementation, the first appliance 31 or the second appliance 32 is a water consuming appliance.

In addition to further examples of device functions described herein, the following are examples of device functions applied by the second appliance 32 based on identification data collected at the first appliance 31. In one example, the device function may turn on (activate) or turn off (deactivate) a power status, a standby status, or a data or water flow to the intelligent mirror 1, the programmable shower 2, the bathtub sensory device 3, the bathtub level device for faucet 5, the intelligent toilet 6, the toilet seat 7, the sink faucet 8, the light source 9a, the kitchen faucet 21, the dishwasher 22, the garbage disposal 23, the refrigerator 24, the water heater 25, and/or the water filter 26.

Specific examples of device functions for the programmable shower 2 may include determining a shower sequence in response to the identity of the user determined by the server 13 based on the sensor data collected by the first appliance 31. The shower sequence may include at least one timing component for the user, at least one temperature component for the user, at least one shower head selection for the user, or at least one spray selection for the user. The shower sequence may vary based on season, weather, time of day, or day of week. When the sensor data includes a state of the user based on health, heart rate, temperature, or stress, the shower sequence is based on the state of the user.

Specific examples of device functions for the bathtub device may be applied to the bathtub sensory device 3 or the bathtub level device for faucet 5. The device function may be a flow of water, a temperature of water, or activating or deactivating the faucet 5. The device function may specify a level of the bath. The drain and faucet 5 may be coordinated (e.g., commands to release some water and add some water to the bath) to maintain a specific level. In addition or in the alternative, the drain and faucet 5 may be coordinated to maintain a specific temperature for the bath. The device function may cause the bathtub sensory device 3 to emit a sequence of audio or vibration to the bath. The sequence may be music or a series of vibration pulses.

Specific examples of device functions for the intelligent toilet 6 may include flushing the toilet, cleaning the toilet, illuminating the toilet, or warming a portion of the toilet. Specific examples of device functions for the faucets may include a volume of water, a temperature of water, or a time duration of water. The second appliance 32 includes the light source 9a configured to illuminate a specific area as the device function.

Specific examples of device functions for the water filter 26 configured to filter a flow of water. The filter may be selected based on the identity of the users. A user configuration may include a preference for water filtering that specifies a particular type of filtering or a substance to be removed from the water. The water filtering may also be implemented by any faucet, the refrigerator 24, or the water heater 25. In addition, a water additive system may be implemented by any faucet, the refrigerator 24, the water heater 25, the water filter 26, or another water consuming device. The water additive system is configured to provide an additive to a flow of water. A user configuration may include a preference for water additive that specifies a particular additive for the water. Example additives described herein include fluoride, vitamins, or flavoring.

Figure 9:
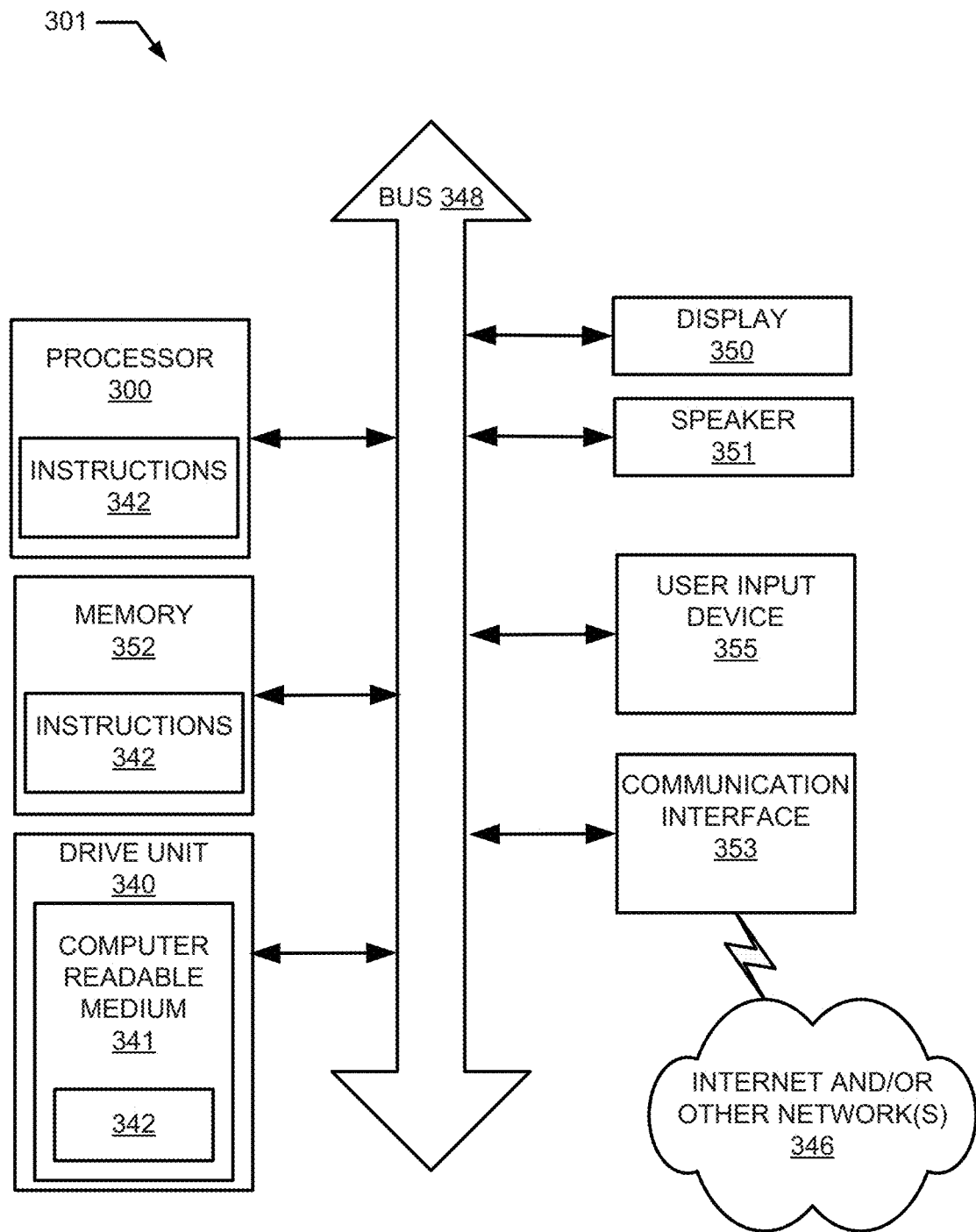
FIG. 9 illustrates a control system for the appliances or home hub communication device, according to an exemplary embodiment.

FIG. 9 illustrates a control system 301 for the appliances or home hub communication device, according to an exemplary embodiment. The control system 301 can be implemented by any of the appliances in FIG. 1 and/or FIG. 2, the network device 14 or the server 13. The control system 301 may include a processor 300, a memory 352, and a communication interface 353 for interfacing with devices (e.g., appliances, network device 14, or server 13, respectively) or to the internet and/or other networks 346. The components of the control system 301 may communicate using bus 348. The control system 301 may be connected to a workstation or another external device (e.g., control panel) and/or a database for receiving user inputs, system characteristics, and any of the values described herein. Optionally, the control system 301 may include an input device 355 and/or a sensing circuit in communication with any of the sensors. The sensing circuit receives sensor measurements from as described above. Optionally, the control system 301 may include a drive unit 340 for receiving and reading non-transitory computer media 341 having instructions 342. Additional, different, or fewer components may be included. The processor 300 is configured to perform instructions 342 stored in memory 352 for executing the algorithms described herein.

Figure 10:
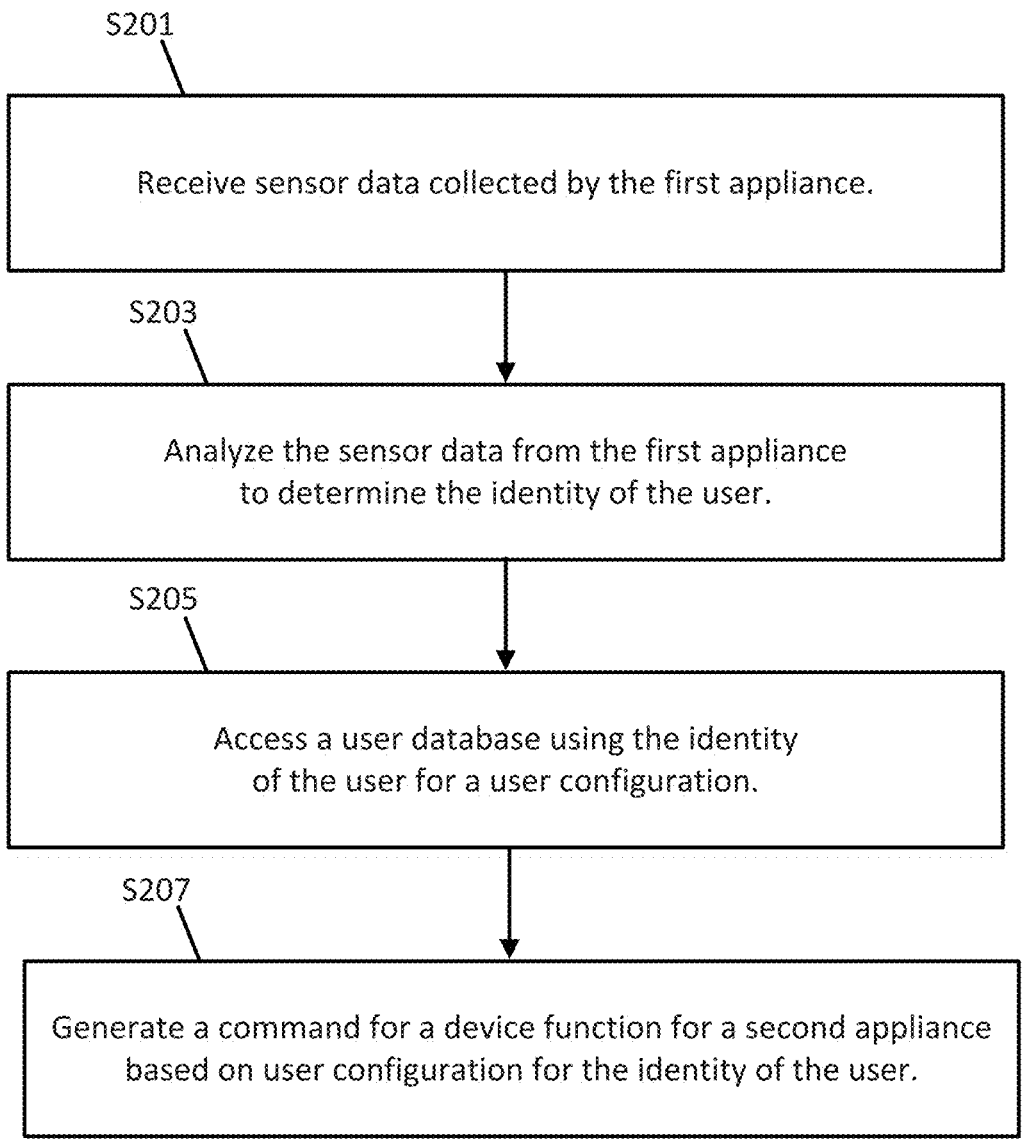
FIG. 10 is a flow chart for the home hub communication device, according to an exemplary embodiment.

FIG. 10 illustrates a flow chart for the operation of one appliance based on identification data collected at another appliance, according to an exemplary embodiment. The acts of the flow chart may be performed by any combination of the home hub communication device, the network device 14 or the server 13. Portions of one or more acts may be performed by the appliance. Additional, different of fewer acts may be included.

At act S201, control system 301 (e.g., through communication interface 353) receives sensor data collected by the first appliance 31. The sensor data is associated with an identity of a user. The sensor data may be received through wireless communication and encoded with a timestamp, a device identifier for the first appliance 31, and a data type identifier for the type of sensor that collected the sensor data. The sensor data may be collected by a combination of sensors. The communication interface 353 may include circuitry, a module, or an application specific controller as a means for receiving sensor data collected by the first appliance.

At act S203, the control system 301 (e.g., through processor 300) analyzes the sensor data from the first appliance to determine the identity of the user. The control system 301 may match a physical characteristic described in the sensor data with a stored value for the user. The control system 301 may match a series of values over time, or a series of values across multiple sensors, with a stored profile for the user. The processor 300 may include circuitry, a module, or an application specific controller as a means for analyzing the sensor data from the first appliance to determine the identity of the user.

At act S205, the control system 301 (e.g., through processor 300) accesses a user database using the identity of the user for a user configuration. The user configuration may include preferences for the user applicable across multiple appliances such as whether or not to enable or disable types of device functions. The user configuration may include specific settings saved for the user. The user configuration may include a sequence of preferred function or a time for when particular device function is preferred by the user. The processor 300 may include circuitry, a module, or an application specific controller as a means for accessing a user database using the identity of the user for a user configuration At act S207, the control system 301 (e.g., through processor 300) generates settings for controlling generating a command for a device function for a second appliance based on user configuration for the identity of the user. The processor 300 may include circuitry, a module, or an application specific controller as a means for generating a command for a device function for a second appliance based on user configuration for the identity of the user.

Intelligent Mirror

Figure 11A:
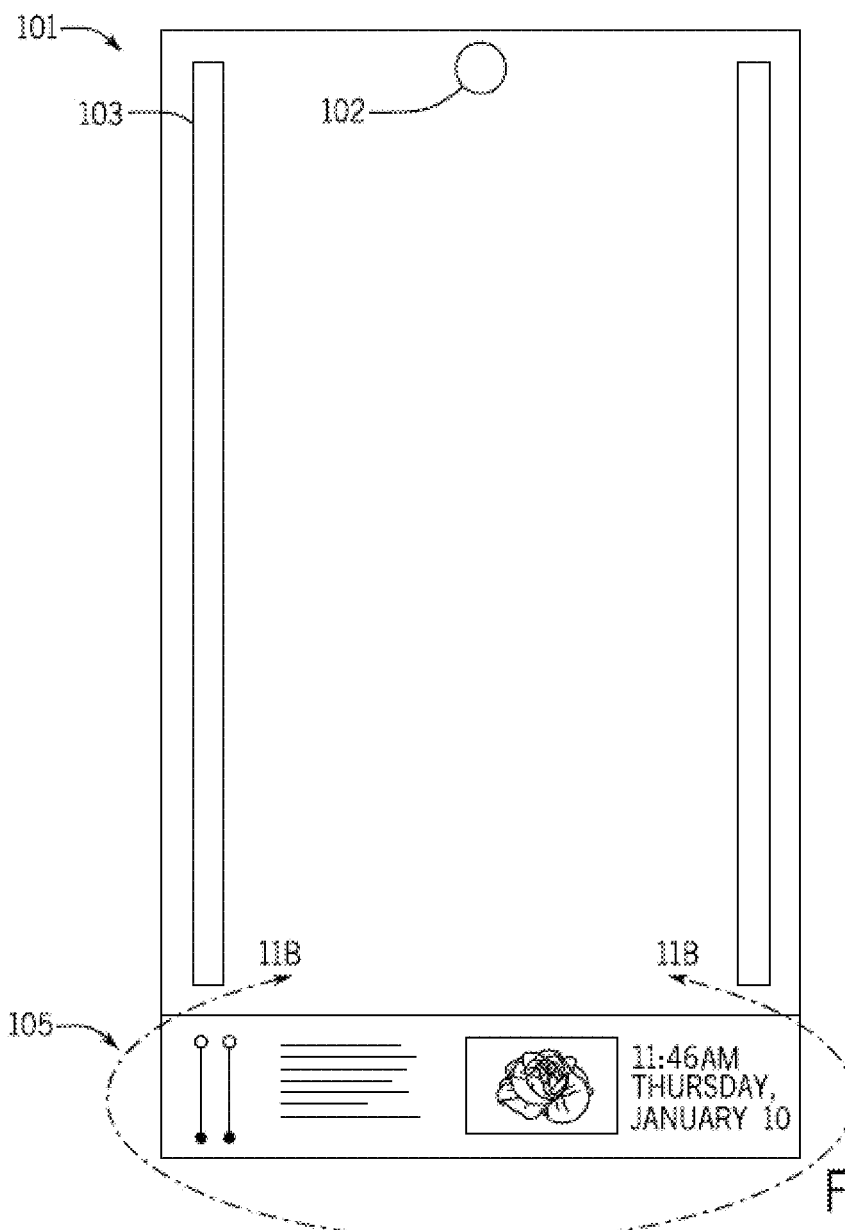
FIGS. 11A and 11B illustrate a mirror and cabinet including a home hub communication device and user interface, according to an exemplary embodiment.
Figure 11B:
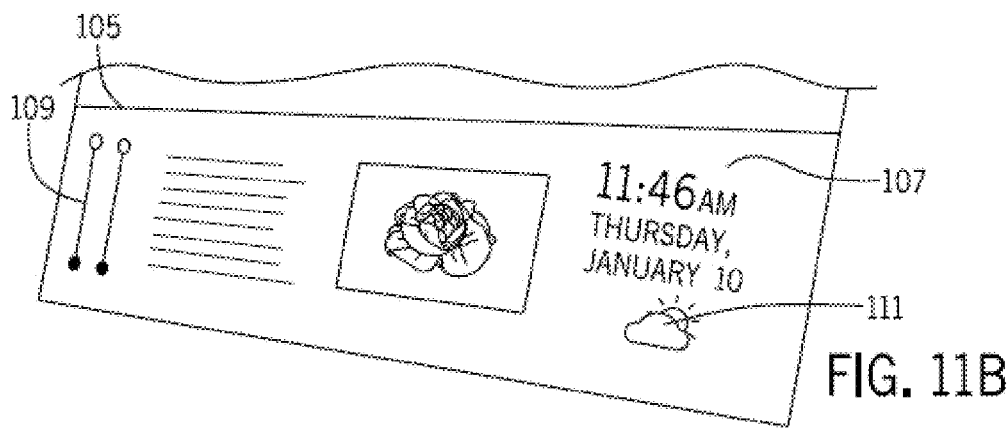

FIG. 11A (and the exploded view FIG. 11B) illustrate an example mirror 101, and cabinet behind the mirror 101, including a home hub communication device, at least one light strip 103, and user interface 105. Alternatively, the mirror 101 may communicate with another home hub communication device, which may be a standalone device or integrated with another appliance. Additional, different, or fewer components may be included.

The mirror 101 may include a mirror substrate configured to provide a reflection of objects including a user. The mirror substrate reflects substantially all of the light that meets the mirror substrate at the same angle the light meets the mirror substrate and/or substantially none of the light is absorbed or scattered. Substantially all of the light may mean 90%, 99% or another proportion of the light. Substantially none of the light may mean 10% 1% or another proportion of the light. The mirror substrate may be made from polished material or from transparent glass that is coated with a thin layer of reflective metal (e.g., silver or aluminum).

The mirror 101 may include a sensor 102 configured to collect sensor data from the user. The sensor 102 may be an image collection device with a lens such as a digital aperture collection device (e.g., camera) or an image collection device with a charge coupled device (CCD) such as an integrated circuit formed on a silicon surface forming light sensitive elements. The image collection device may collect images for facial recognition of the user. The image collection device may collect images for recognizing an image signature of the user such as the color or shape (e.g., bone density, outline, height, and/or weight) of the user. Other body properties may be determined from the image of the user including skin qualities at a cellular level, signs of hormone imbalance, aging, sun damage, pigmentation, color, inflammation, environmental impacts, or other abnormalities. For example, the images of the user's teeth may be analyzed for feedback for brushing teeth. The mirror 101 detects whether brushing or flossing was sufficient and instructs the user to continue brushing or flossing. In another example, the images of the user's muscles are analyzed to determine muscle conditions (e.g., strains, pulls, or tears) which are highlighted on the display and transmitted to an exercise device for a customized workout or to a trainer or website for customized exercise plan.

The sensor 102 may be a relative distance collection device such as a proximity sensor or a laser scanner. The laser scanner may emit one or more laser pulses that reflect off of objects and are received by the laser scanner. The time of flight for the laser pulses indicates the distance to the objects. The proximity sensor may detect a presence of an object at a predetermined distance or within a predetermined distance range. The proximity sensor may include a microwave or radar sensor. Example predetermined distances may be 28 inches, 1 meter or another distance. The range of the proximity sensor may be cone shaped.

The sensor 102 may be a temperature mapping device such as an infrared camera for detecting a heat signature of the user. The sensor 102 may be a retina scanner configured to scan the eyes of the user. The retina scan may indicate an eye signature for identification of the user. The retina scan may reveal the blood sugar level of the user.

The sensor 102 may be an audio sensor such as a microphone. The sensor 102 may detect odors. The sensor 102 may detect volatile organic compounds (VOCs) or other carbon based (organic) chemicals (compounds) that are indicative of odor. The sensor 102 may be an environment sensor such as a temperature sensor, a light sensor, or a humidity sensor. The sensor 102 may be a remote sensor in another location (e.g., a different room than the mirror assembly 101.

The mirror assembly 101 comprises user interface 105, which is configured to receive an instruction from the user and/or display data to the user. The instruction from the user may trigger an auxiliary command for the auxiliary device. The data displayed at the user interface 105 includes status data for the auxiliary device, settings data for the auxiliary device, configuration data for the user, or type data for the auxiliary device.

Figure 12:
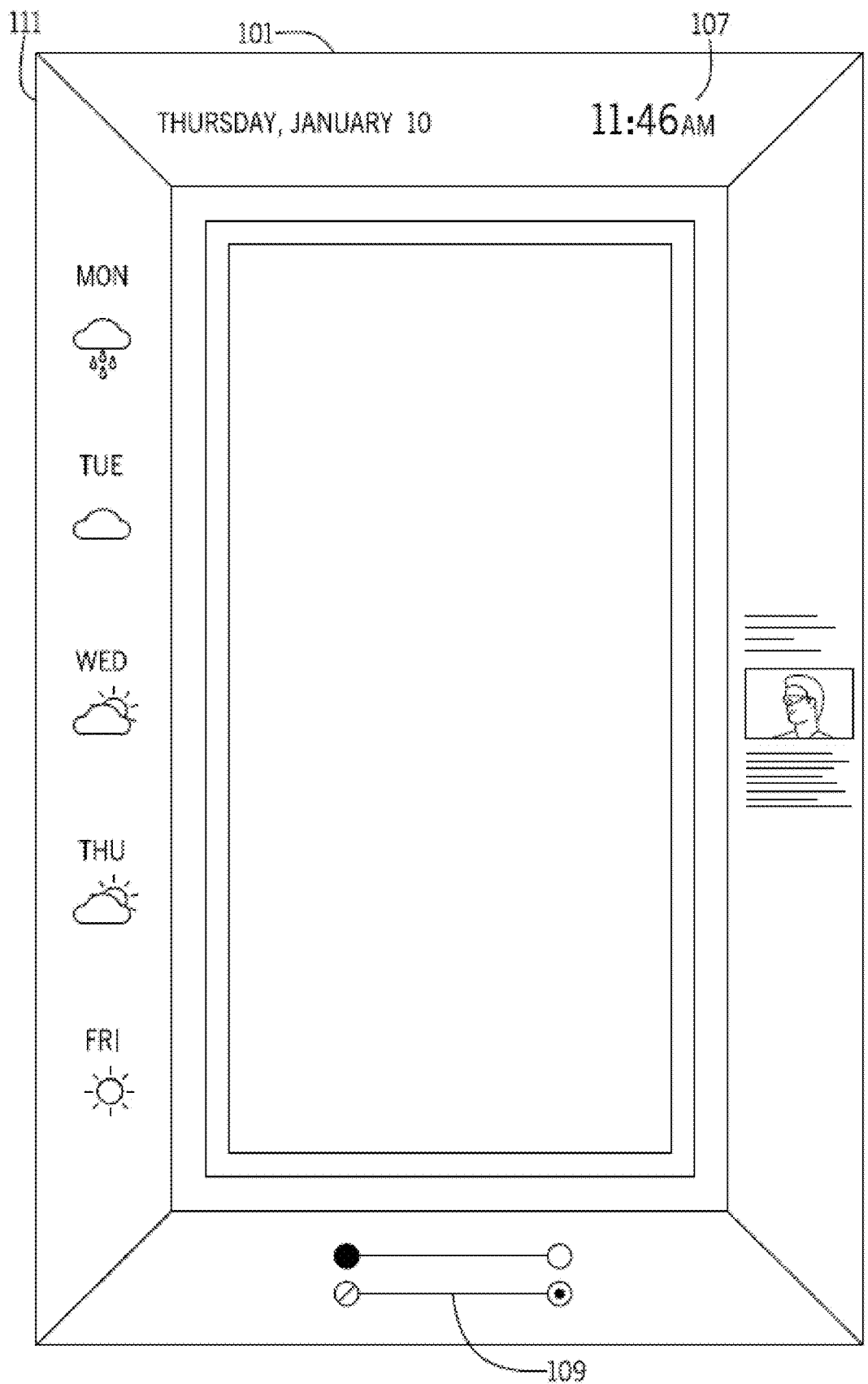
FIG. 12 illustrates another user interface which can be presented via a mirror and cabinet, according to an exemplary embodiment.
Figure 13:
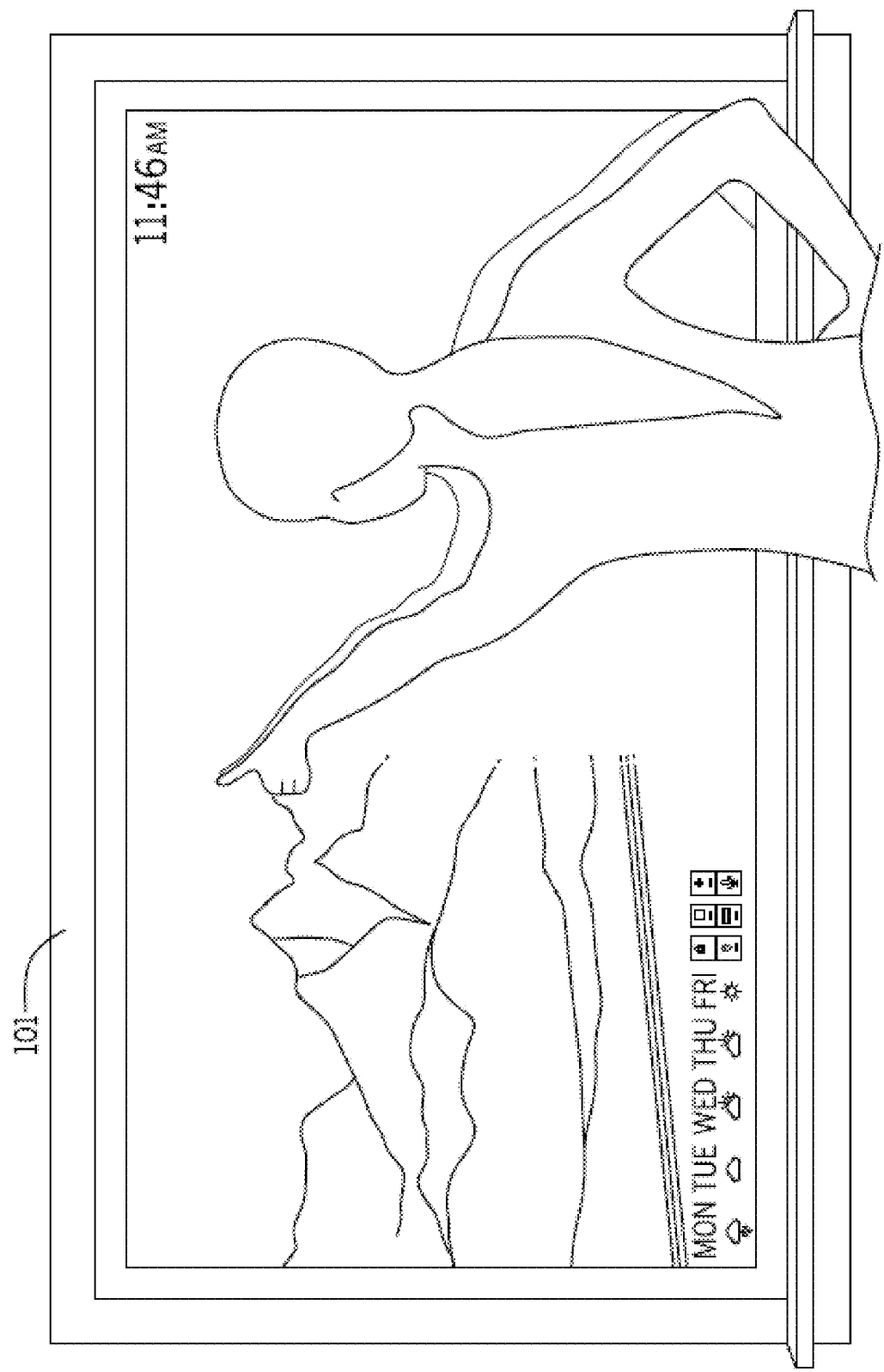
FIG. 13 illustrates an example transitional user interface and mirror, according to an exemplary embodiment.

The user interface 105 may include a touchscreen. The user interface 105 may include a temporal component 107, a user input 109, and a weather component 111. FIG. 12 illustrates another example user interface for a mirror and cabinet, including a similar temporal component 107 and weather component 111. FIG. 13 illustrates another embodiment of the user interface and mirror substrate integrated as a transitional user interface and mirror. By varying an electric current through different portions of the mirror substrate, the mirror substrate may change between a mirror and the user interface. A network of traces or wires carry the varying electric current. In one example, when data is received from another device, the current is varied so that a portion of the mirror becomes a user interface. In one example, when a summons command is received from the user, the current is varied so that a portion of the mirror becomes a user interface.

Figure 14B:
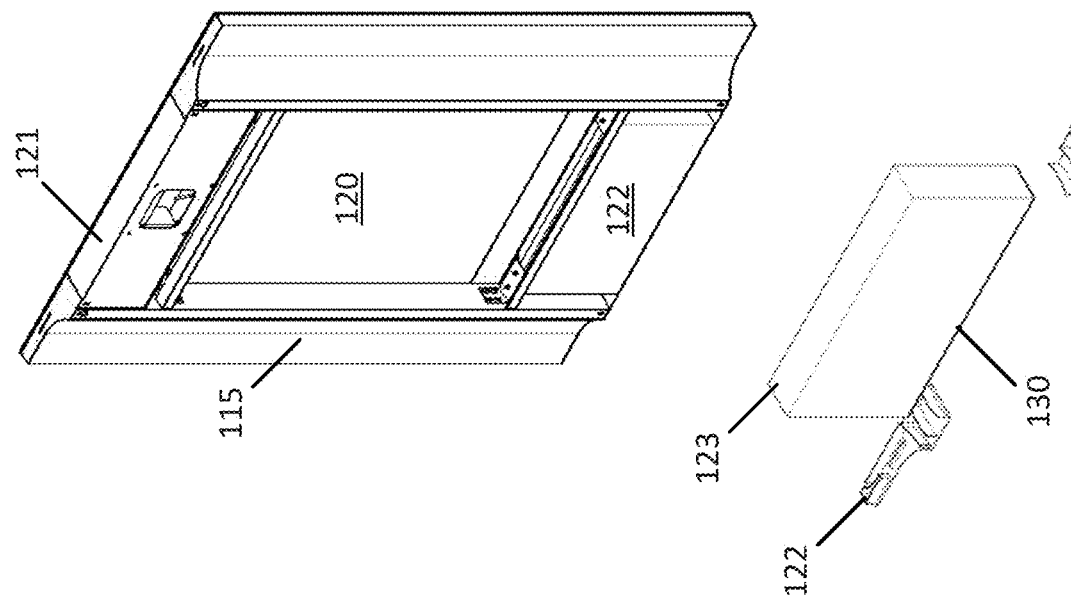
FIGS. 14A and 14B illustrate a housing for a communication module and mirror interface, according to an exemplary embodiment.
Figure 14A:
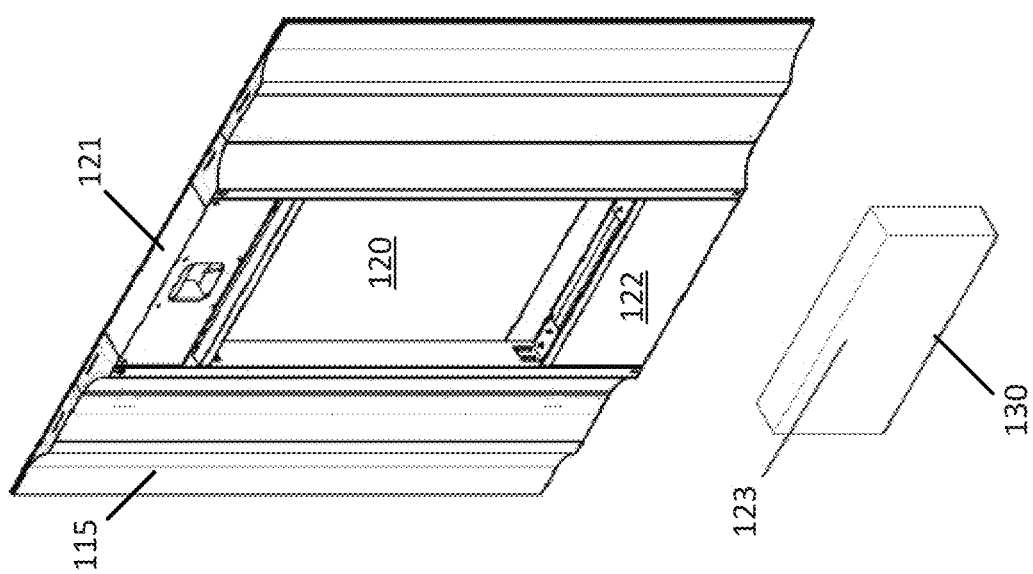

FIGS. 14A and 14B illustrate an apparatus for a mirror including a support housing 115, a sensor module 121, a control module housing 122, and mirror interface 120, according to an exemplary embodiment. A control module 123 may be shaped to mate and/or fit inside the control module housing 122. The control module 123 may include a control interface 130 on the underside. FIG. 14A illustrates a wider support housing 115 and FIG. 14B illustrates a narrow support housing 115. FIG. 14B also illustrates support feet 124 for holding the control module 123 to the support housing 115. Additional, different, or fewer components may be included.

The sensor module 121 may include one or more of the types of sensors that collect sensor data in the examples described herein. The sensor data for a user is received at the mirror assembly 101, or specifically control module 123, from the sensor module 121 or an external sensor. The control module 123 may include a controller configured to analyze the sensor data and select an auxiliary command for an auxiliary device coordinated with the mirror assembly, the auxiliary command selected for the user.

The auxiliary device is one of the appliances described herein. The auxiliary device may be an adjacent device within the same room as the mirror assembly 101 or less than a predetermined distance to the mirror assembly 101. The auxiliary device may be a remote device in a different room from the mirror assembly 101 or greater than a predetermined distance from the mirror assembly 101. With respect to the mirror assembly 101, the adjacent devices may include bathroom devices such as the intelligent mirror 1, the programmable shower 2, the bathtub sensory device 3, the bathtub level device, the intelligent toilet 6, the toilet seat 7, the sink faucet 8, light guides, or a fan. With respect to the mirror assembly 101, the remote devices may include kitchen devices such as the kitchen faucet 21, the dishwasher 22, the garbage disposal 23, the refrigerator 24, the water heater 25, and the water filter 26.

The control module 123 may select, based on the analysis of the sensor data, an auxiliary command for an auxiliary device coordinated with the mirror assembly 101. The auxiliary command may be selected for a particular user. The auxiliary command for the auxiliary device is based on the instruction from the user received at the user interface and the data displayed at the user interface includes status data for the auxiliary device, settings data for the auxiliary device, configuration data for the user, or type data for the auxiliary device.

The analysis of the sensor data may determine an instruction received at the user interface 105. For example, the user may enter a command for the programmable shower 2 (e.g., select shower sequence or turn on/off shower), a command for the bathtub sensory device 3 (e.g., select a bath experience), a command for the bathtub level device (e.g., select a bath level), a command for the intelligent toilet 6 (e.g., flush or close the lid), a command for the toilet seat 7 (e.g., raise or lower the toilet seat), a command for the sink faucet 8 (e.g., select a temperature or volume), a command for light guides (e.g., a position or angle for the light), a command for the fan (e.g., a fan speed or on/off), a command for the kitchen faucet 21 (e.g., select a temperature or volume), a command for the dishwasher 22 (e.g., a cleaning mode or on/off), a command for the garbage disposal 23 (e.g., a speed or on/off), a command for the refrigerator 24 (e.g., select a temperature), a command for the water heater 25, (e.g., select a temperature), or a command for the water filter 26 (e.g., activate or deactivate).

Settings data for the auxiliary device may be based on information received at the control module 123 from another of the auxiliary devices. For example, data collected regarding height from a shower setting may be applied to a toilet seat position, a position of the user interface 105 on the mirror substrate or a position of a light guide. Configuration data for the user may be based on the identification of the user or detection of the user and preferences previously established for the user. Type data for the auxiliary device may be used to apply a setting across a class of devices. For example, the user preferences may specify a temperature that is applied to all auxiliary devices with a temperature setting.

In one example, the control module 123 includes the components illustrated by FIG. 9. The control module 123 may include a communication interface configured to send the auxiliary command to the auxiliary device.

The control module 123 may include a speaker configured to provide audio for status data for the auxiliary device, settings data for the auxiliary device, configuration data for the user, or type data for the auxiliary device. The speaker may be movable. The control module 123 may engage a positioning mechanism (e.g., stepper motor or solenoid) to move the speaker toward a user. The degree of movement may depend on the task performed by the user, the identity of the user, the height of the user, the preferences of the user. The volume of the speaker may be configurable. The control module 123 may set a volume of the speaker based on the task performed by the user, the identity of the user, the age of the user, the height of the user, the preferences of the user. For example, volume may be set proportional to age. Certain tasks may invoke higher volumes. For example, when the shower is running a higher volume is used.

The control module 123 may include a microphone configured to collect audio (e.g., voice commands) for settings data for the auxiliary device, configuration data for the user, or type data for the auxiliary device. The microphone may be movable. The control module 123 may engage a positioning mechanism (e.g., stepper motor or solenoid) to move the microphone toward a user. The degree of movement may depend on the task performed by the user, the identity of the user, the height of the user, the preferences of the user. The volume of the microphone may be configurable.

The voice commands received at the control module 123 may include device identifiers that describe the auxiliary device and device functions to be performed by the auxiliary device, which are described herein with respect to various appliances. In addition, the voice commands may include a device identifier for the mirror assembly 101, or omitting the device identifier may default to the mirror assembly, and a device function for the mirror assembly 101. Example functions performed at the mirror assembly 101 may include control of the lights, control of the light guide, selection of the collected data and selection of the displayed data.

The control of the lights (e.g., light strip 103) may include the color of the lights, brightness of the lights, intensity of the lights, or schedule for the lights. The control of the light guide may include an angle or position for the light is determined based on the auxiliary command selected for the user. For example, the voice command may instruct the light guide to illuminate handwashing in response to the voice command. The selection of the collected data may enable or disable one or more sensors. The selection of the displayed data may enable or disable the display of external data (e.g., weather) or data received from auxiliary devices.

In one example, the control module 123 may include an inductive charging assembly including one or more inductive chargers. The inductive chargers may include coils of wire configured to produce magnetic fields that charge batteries in mobile devices. The mobile device may be placed on control module 123 to charge the battery of the mobile device. A charging assembly may be incorporated into any of the appliances described herein.

Figure 15:
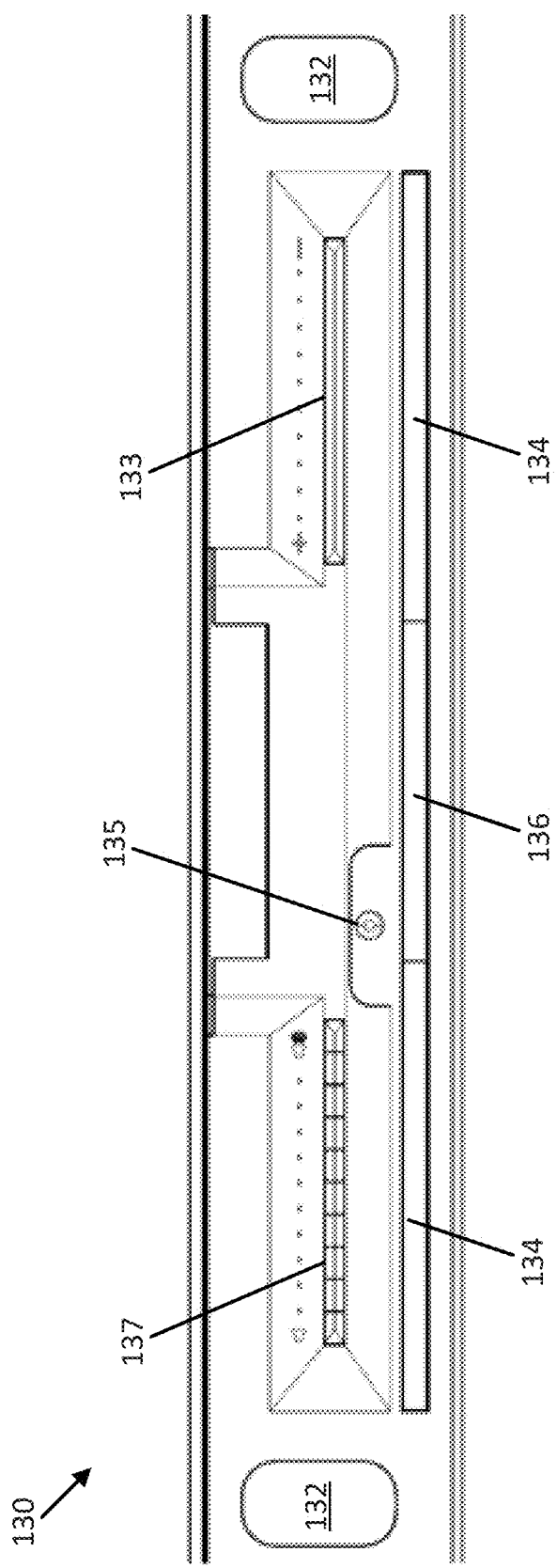
FIG. 15 illustrates controls for the communication module of FIGS. 14A and 14B, according to an exemplary embodiment.

FIG. 15 illustrates a control interface 130 for the communication module of FIGS. 14A and 14B, according to an exemplary embodiment. The control interface 130 may include one or more tactile switches such as a volume control 137, a capacitive light control 133, and a wireless network toggle button 135. The capacitive light control 133, or any of the inputs to the control interface 130 may include a capacitive sensor responsive to touch. Adjacent to the control interface 130 may be one or more speakers 132, and an array of light emitting diodes (LEDs) including nightlight LEDs 134 and home hub communication indicators 136.

The control interface 130 may provide a command for the auxiliary device. As shown, volume control 137 and/or capacitive light control 133 may be applied to auxiliary devices. Otherwise, the control interface 130 may include an activation for turning an auxiliary device on and off. The wireless network toggle button 135 may also turn wireless communication with an auxiliary device on and off.

Figure 16:
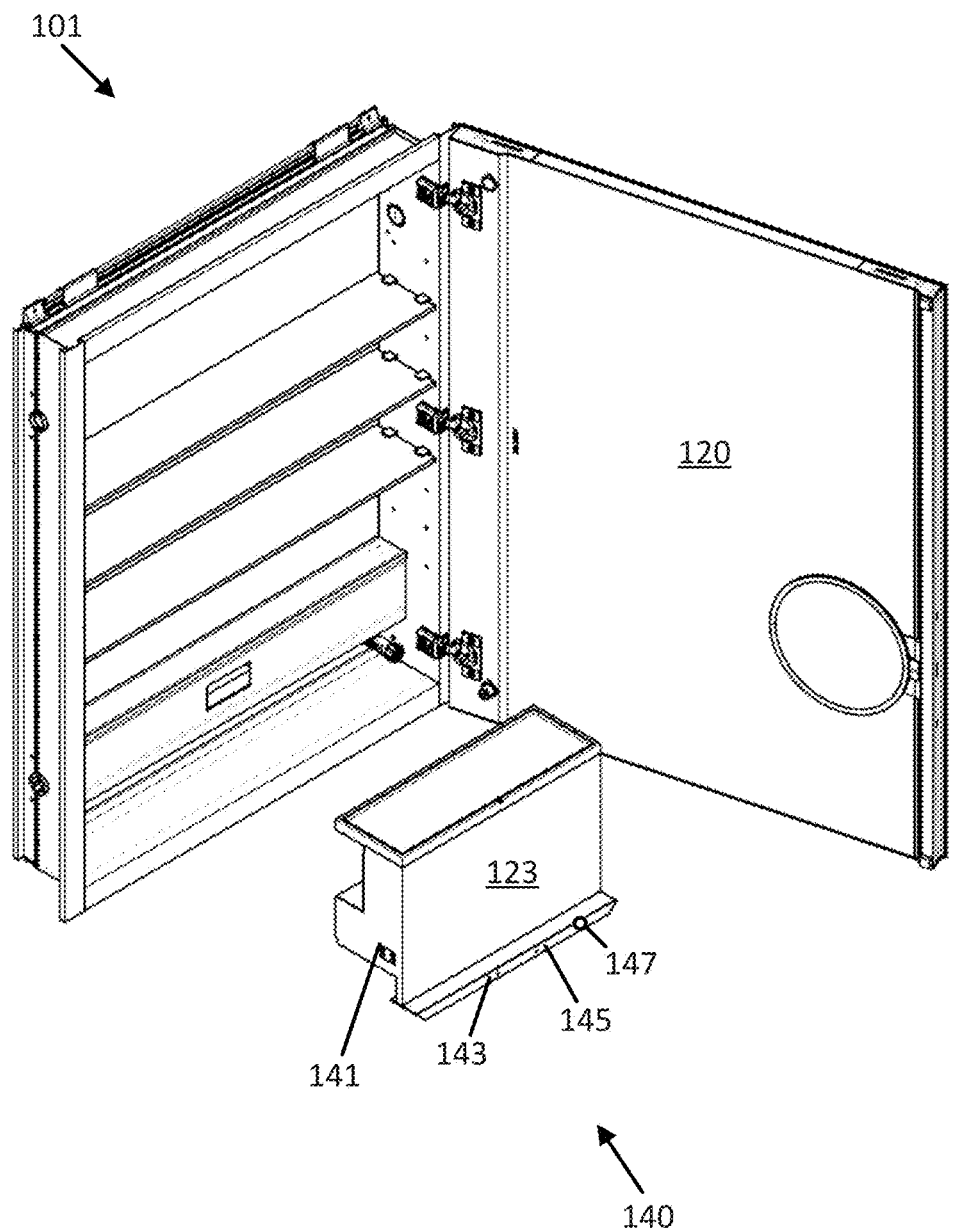
FIG. 16 illustrates a panel for the communication module of FIGS. 14A and 14B, according to an exemplary embodiment.

FIG. 16 illustrates a cabinet including a panel 140 for the control module 123 of FIGS. 14A and 14B, according to an exemplary embodiment. The cabinet, including one or more storage spaces or compartments, may be coupled to the mirror interface 120. Alternatively, the mirror interface 120 may be omitted. The panel 140 may include a universal serial bus or similar communication port 141, a microphone activated or muted LED 143, an inquiry LED 145, and a proximity sensor 147.

The communication port 141 may connect to a laptop or smart phone for setup or configuration of the control module 123. In one example, configuration requires a hard wired connection. The communication port 141 may be used as a charging port for a phone, a shaver, a hair dryer, or other chargeable appliance. The communication port 141 may communication with supplemental or replacement lights, speakers or microphones.

The microphone activated or muted LED 143 is an indicator that indicates when the microphone is in use. The user may activate or deactivate the microphone using a voice command or other user input. The inquiry LED 145 may indicate that voice commands are being received. For example, the inquiry LED 145 may illuminate in response to the summons command. Thus, the inquiry LED 145 indicates that the home hub communication device has correctly identified that voice commands are being received. The proximity sensor 147 may be used in coordination with sensor 102.

Intelligent Toilet

Figure 17:
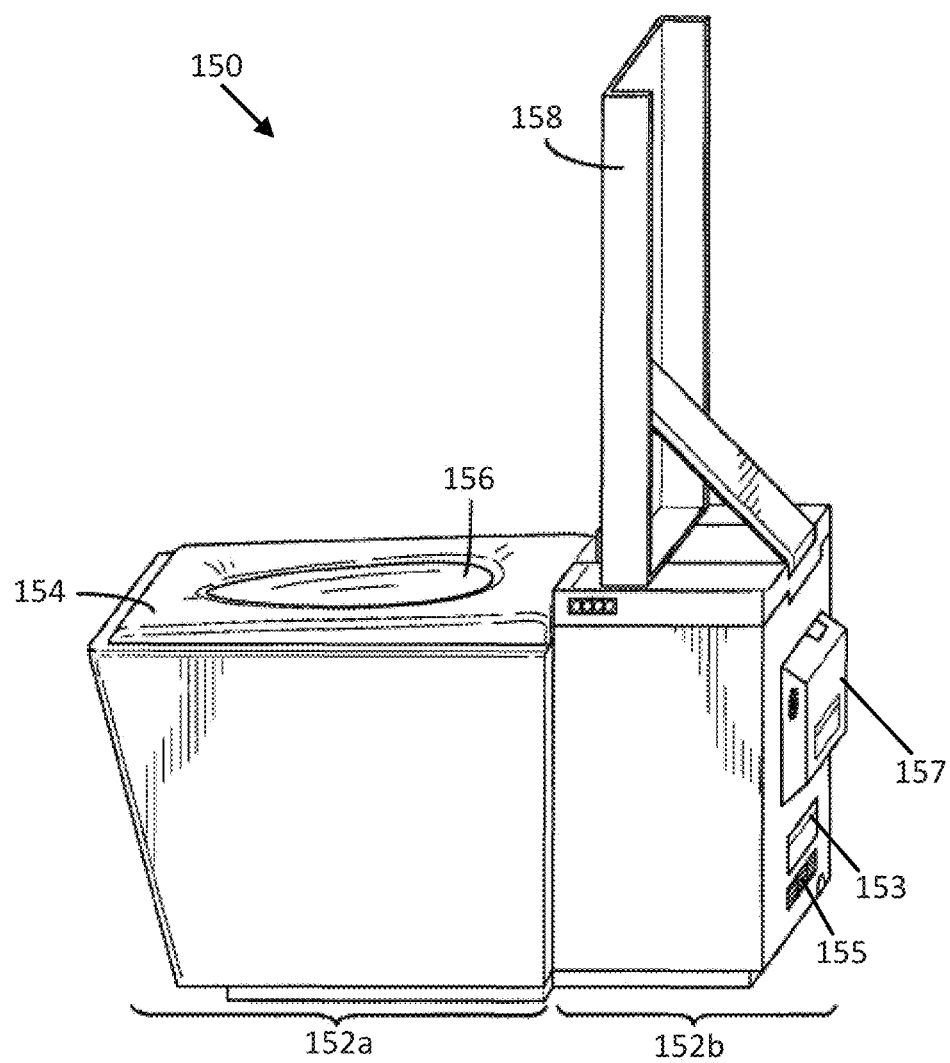
FIG. 17 illustrates a toilet including a home hub communication device and user interface, according to an exemplary embodiment.

FIG. 17 illustrates a 150 including a home hub communication device and user interface, according to an exemplary embodiment. The toilet 150 is a plumbing fixture including a basin 156, a lid 158, a seat 154, and a housing. The seat 154 may be controlled by an electromechanical lifting and closing device configured to automatically open and close the seat. The toilet 150 may receive a fluid input (e.g., water) from a fluid supply line and may deliver the fluid to basin 156 via an internal fluid connection (not shown). The toilet 150 may receive electrical energy from an external or internal energy source. For example, the toilet 150 may connect to a standard residential power outlet (e.g., 120 V 60 Hz), a power generator, or other power source (e.g., batteries, capacitors, etc.). In some embodiments, the toilet 150 functions as a toilet, using the fluid to flush, rinse, or otherwise clean basin 156. The toilet 150 may provide a variety of flushing options configured to carry out the flushing process. For example, one flushing option may clear basin 156, automatically wash basin 156, and then refill basin 156 for subsequent use. Other flushing options may automatically clean basin 156, sanitize basin 156, or initiate a process to reduce or eliminate odor. The toilet 150 may provide one or more flushing options configured to use various amounts of water or power during the flushing cycle. In some embodiments, the toilet 150 may include a bidet wand, a cleaning element, a fan, or other optional features. In some embodiments, the toilet 150 functions as a bidet, delivering the fluid to the bidet wand. When the toilet 150 functions as a bidet, the seat may be automatically lifted using the electromechanical lifting and closing device. The toilet 150 may provide a variety of bidet control options including user-customizable spray patterns and an adjustable spray pressure, temperature, or position. The toilet 150 may automatically clean and sanitize the bidet wand using an internal ultraviolet sanitizing light. In some embodiments the toilet 150 functions as a combination toilet and bidet, providing both functionalities.

The toilet 150 is shown to include a housing. The housing may enclose (e.g., surround, encapsulate, contain, etc.) some or all of the other components of the toilet 150 (e.g., plumbing components, electrical components, mechanical components, etc.). The toilet 150 may provide support for other components, thereby allowing such components to be positioned for proper operation of the toilet 150 as described herein. In some embodiments, housing may protect the internal components from external sources of damage (e.g., physical damage, chemical damage, electrical damage, etc.). In some embodiments, housing may be a single shell encapsulating all of the toilet 150. In other embodiments, the housing may include multiple shells. For example, FIG. 17 shows the housing divided into multiple sections. A frontal housing section 152*a* is shown supporting basin 156. A rear housing section 152*b* is shown surrounding another portion of fixture the toilet 150. The rear housing section 152*b* may include a control module 157 (e.g., the control system 301 of FIG. 9), a display 153, and a communication module 155.

Figure 18A:
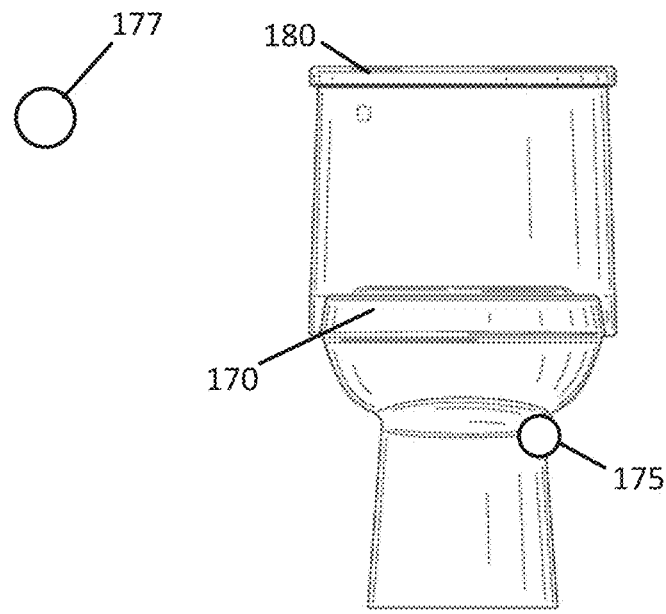
FIGS. 18A and 18B illustrate a toilet and a home hub communication device including multiple automated devices, according to an exemplary embodiment.

FIG. 17 illustrates an all in one or integrated embodiment of the intelligent toilet 150. FIG. 18A illustrates a distributed embodiment of an intelligent toilet 180 including modular components for an automated covering assembly 170, a touchless flush device 177, and an automatic cleaning system 175.

The automatic cleaning system 175 may include a valve that releases a solution in the tank of the intelligent toilet 180. The solution flows to the basin 156 to clean the basin at the point illustrated in FIG. 18A. The automatic cleaning system 175 may include a sprayer that spray a solution into the basin 156. The solution may be cleaning solution or disinfected solution.

The touchless flush device 177 may be an electronic flush mechanism for sending a flush command to the intelligent toilet 180. The touchless flush device 177 may include a remote detector (e.g., a disk or puck) and a mechanical flusher coupled to the basin 156. The touchless flush device 177 may include a gesture sensor, which is a type of proximity sensor configured to detect a gesture by the user. The gesture may be waving a hand or otherwise placing a hand near the touchless flush device 177.

Figure 18B:
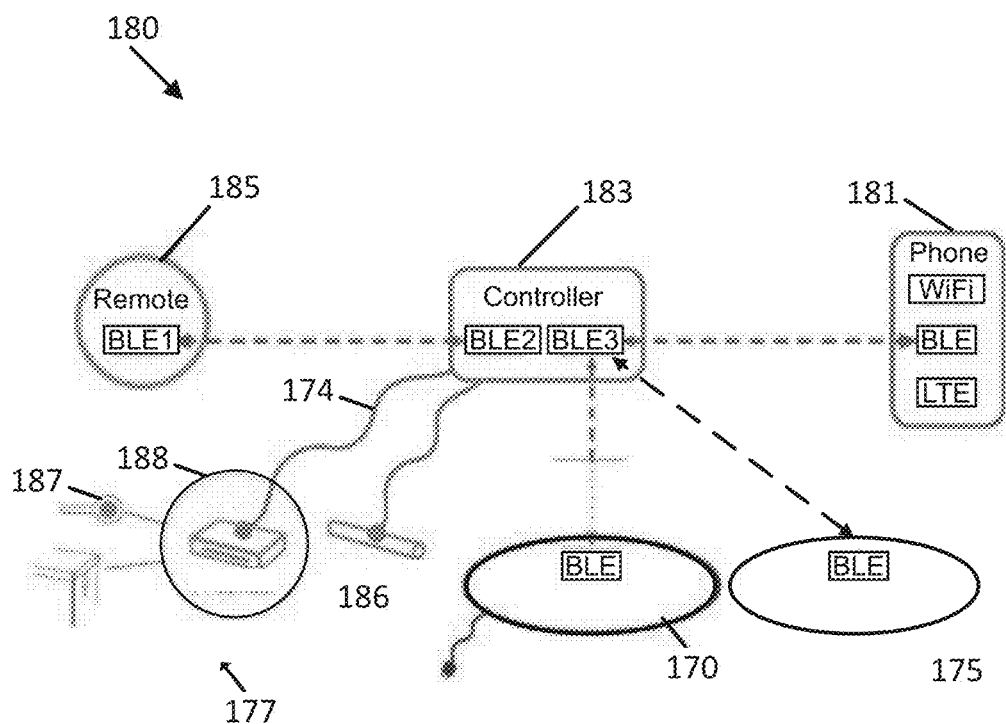
Figure 19A:
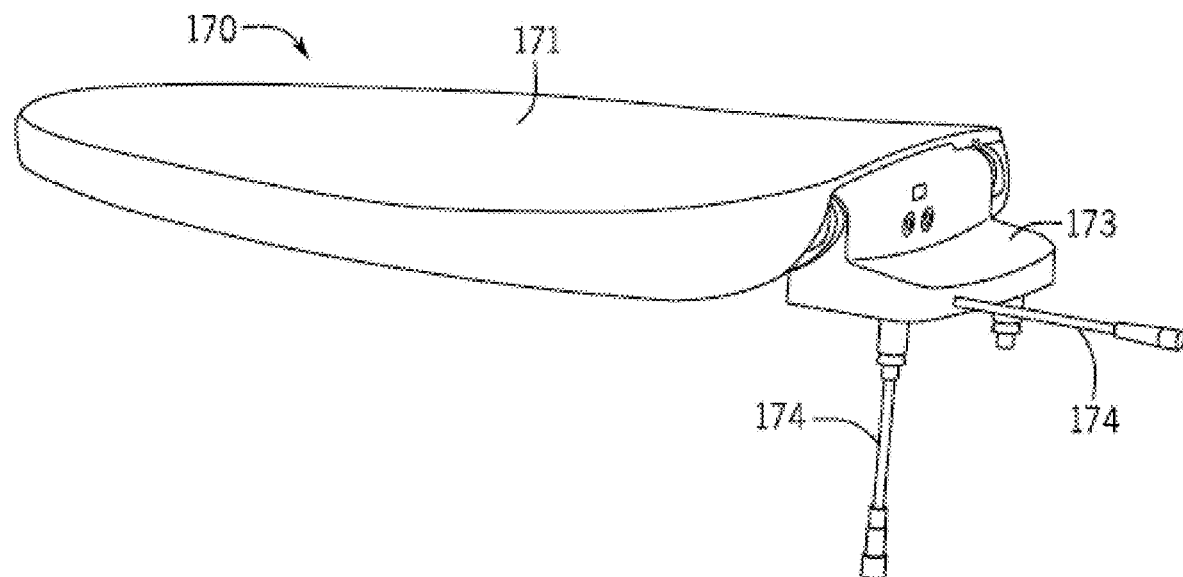
FIGS. 19A and 19B illustrate an automatic toilet seat, according to an exemplary embodiment.
Figure 19B:
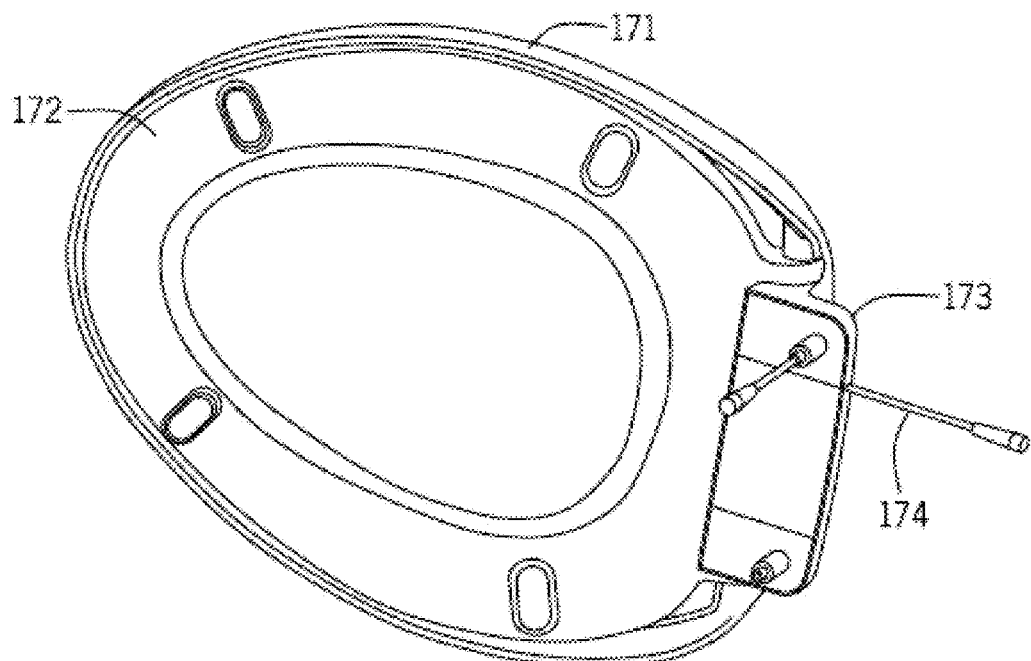

FIG. 18B illustrates a control system and communication system for the intelligent toilet 180, according to an exemplary embodiment. The control system includes a controller or control module 183 (e.g., the control system 301 of FIG. 9), a dedicated remote 185, a remote application on phone 181, a heater 182, a light strip 186, a sensor 188, and a mechanical flush lever 187. FIGS. 19A and 19B illustrate an automated toilet covering assembly 170 including lid 171, a seat 172, which may be integrated with toilet in a single construction, a hinge assembly 173, and one or more electrical connectors 174. Additional, different or fewer components may be included. Herein the control module 183 refers to both the controller of the all in one or integrated embodiment of the intelligent toilet 150 and the distributed embodiment of an intelligent toilet 180 including modular components.

The control module 183 coordinates any combination of the automated covering assembly 170, the touchless flush device 177, and the automatic cleaning system 175. The control module 183 may send commands to automated covering assembly 170.

The control module 183 may send commands to the touchless flush device 177 to operate the mechanical flush lever 187. The control module 183 may send commands to the automatic cleaning system 175 to initiate a cleaning process (e.g., spray or inject cleaning solution). The dedicated remote 185, or the remote application on phone 181, may receive user input for any of the commands for the control module 183.

The intelligent toilet 180 may include a sensor, such as the sensor 188, configured to collect sensor data from the user. The sensor 188 may be an image collection device with a lens such as a camera or an image collection device with a charge coupled device (CCD) such as an integrated circuit formed on a silicon surface forming light sensitive elements. The image collection device may collect images of the user. The image collection device may collect images for recognizing an image signature of the user such as the color or shape (e.g., bone density, outline, height, and/or weight) of the user. The image collection device may be a gesture sensor.

The sensor 188 may be a relative distance collection device such as a proximity sensor (e.g., sensor 188) or a laser scanner. The laser scanner may emit one or more laser pulses that reflect off of objects and are received by the laser scanner. The time of flight for the laser pulses indicates the distance to the objects. The proximity sensor may detect a presence of an object at a predetermined distance or within a predetermined distance range. The proximity sensor may recognize multiple types of gestures. For example, one gesture may correspond to an ecological flush and another gesture may correspond to a normal flush.

The proximity sensor may emit and/or detect a beam of light (e.g., infrared light). Breaking the beam of light or interrupting the beam of light signals that the user is present. Breaking the beam of light includes placing a body part or object in the path of the beam of light so that the proximity sensor does not receive the beam of light. The beam of light may be near the floor or base of the intelligent toilet such that the beam of light can be easily broken by the user's foot.

The sensor 188 may be a temperature mapping device such as an infrared camera for detecting a heat signature of the user. The sensor 188 may be a retina scanner configured to scan the eyes of the user. The sensor 188 may be a fingerprint sensor. The sensor 188 may be an audio sensor such as a microphone. The sensor 188 may detect odors or VOCs. The sensor 188 may be an environment sensor such as a temperature sensor, a light sensor, or a humidity sensor. The sensor 188 may be a remote sensor in another location (e.g., a different from than the intelligent toilet). The sensor 188 may be a leak sensor to detect a water leak in the intelligent toilet. For example, the sensor 188 may detect a water level (e.g., tank, basin) that is analyzed by the control module 183 to determine when a possible leak is occurring.

The sensor 188 may collect data on human waste. The sensor data may be used for a urinalysis or urine screen. The sensor data may include a pH level, an indication of the presence or absence of one or more ketones, an indication of the presence or absence hormones indicative of pregnancy, an indication of the presence or absence of blood cells or bacteria indicative of a urinary tract infection, an indication of the presence or absence of drugs, an indication of the presence or absence of a particular type of cells (e.g., cancer cells) or other substances. The sensor 188 may include a light sensor (e.g., infrared light or laser) to test blood sugar levels or oxygen levels, which may be used to monitor diabetes. The sensor 188 (e.g., a camera) may collect data for stool samples. The control module 183, the home hub communication device, or the external device 30 may perform an image analysis on the stool samples.

The sensor 188 may be configured to output data that describes when the intelligent toilet 180 is in use. The sensor data may be binary including one value to indicate the intelligent toilet is in use and another value to indicate the toilet 180 is not in use.

The sensor 188 may be incorporated in the automated covering assembly 170. A weight sensor (e.g., pressure sensor) may detect the user's weight, or a rough estimate of the user's weight, when seated on the toilet seat. The control module 183 may calculate the weight of the user from the sensor data. The control module 183 may determine a demographic type of user such as man versus woman or adult versus child. The control module 183 may identify the user. For example, in a household, weights of the people are distinct enough to recognize the identity of the individual users. The control module 183 may learn the identities by measuring the weight of a known user. For example, the user may connect using the dedicated remote 185 or the phone 181, and the control module 183 records a weight reading from the sensor. The weight is stored by the control module 183 and when a subsequent user is seated, a subsequent reading is compared to the stored reading to determine whether the identity of the user matches. Any number of readings may be taken for any number of users.

The sensor 188 may be a capacitance sensor or an array of capacitance sensors that detect the legs and thighs of the user. The sensor data may indicate whether or not the user is seated. The sensor data may indicate whether a leg is lifted and for how long. The sensor data indicates usage patterns of the intelligent system.

The automated covering assembly 170, the seat 172, or alternatively intelligent toilet 150, may include sensors such as biometric sensors to detect biological characteristics or biometrics of the user. The sensors may include the weight sensor configured to collect weight data for the user. The sensors may include a sensor for determining height, and the control module 183 may calculated BMI from height and weight.

The biometric sensors may include body composition sensors. A body composition sensor may measure muscle mass and/or body fat percentage using a bioelectrical impedance analysis. Alternatively, the body composition sensor may measure body water percentage contained in the cells and tissues using the bioelectrical impedance analysis, or bone mass using the bioelectrical impedance analysis. Changes in muscle or fat in certain parts of the body change the impedance of those parts of the body. The impedance may be detected by the control module 183 sending a low level electrical current through the user's body and measuring changes in the low level electrical current when it returns to a sensor or the control module 183. The current may enter and return from the user's body through the seat 172 (e.g., legs) or the cover assembly 170 (e.g., back), or the current may enter through one of the seats 172 or the cover assembly 170 and return through the other of the seat 172 and the cover assembly 170.

The biometric sensors may include a metabolic sensor that measures the basal metabolic rate (BMR) or minimal rate of energy per time expended by the user at rest while seated at the toiled. The BMR describes the calories needed by the body to rest.

The biometric sensors may include a photoplethysmogram (PPG) configured to optically obtain a volumetric measurement of an organ. The PPG may be configured to measure the heart rate of the user (e.g., through the skin), cardiovascular pulse wave velocity, respiration, or another characteristic of the user.

In one or more of these examples, the sensors detect biological characteristics such as body composition, heart rate, temperature, or blood pressure of the user. The biometric sensors, taken alone or in combination with the weight sensor, may provide a user signature for identifying the user.

Other sensors may be used to determine the identity of the user. The sensors may include an IR sensor, which is included in the automated covering assembly 170, may generate a seat signature for the user as seated. Similarly, an IR sensor in the front of the basin may generate a heat signature of the user's feet. A proximity sensor may detect the presence or absence of feet and/or gestures made by the feet.

The sensor 188 may be incorporated in the touchless flush device 177 both for detecting the gesture command for initiating a flush and detecting the mechanical flush lever 187 (e.g., for acknowledging the flush has occurred, detecting the number of flushes, or activating a cleaning sequence). In addition or in the alternative, the sensor 188 may be incorporated in the automatic cleaning system 175. The sensor 188 may detect the cleaning sequence or detect commands for initiating the cleaning sequence.

The control module 183 may send commands based on the sensor data to various components of the intelligent toilet 180. When the user is detected by the proximity sensor, the intelligent toilet 180 is placed in a standby mode. The standby mode may include any combination of opening the lid, raising the seat, warming the foot warmer, turning on the display, or turning on the remote 185 or activation the corresponding application on the phone 181.

In addition to commands for the intelligent toilet 180, the control module 183 may select, based on the analysis of the sensor data, an auxiliary command for an auxiliary device coordinated with the intelligent toilet 180. The auxiliary command may be selected for a particular user. The auxiliary command for the auxiliary device is based on the instruction from the user received at the user interface and the data displayed at the user interface includes status data for the auxiliary device, settings data for the auxiliary device, configuration data for the user, or type data for the auxiliary device. For example, the seat may be raised as a function of the identity of the user and/or time of day (e.g., gender, pattern of use).

The analysis of the sensor data may determine an instruction received at the user interface of the intelligent toilet 180, through gestures or other commands received by the sensors (e.g., voice commands). For example, the user may provide instructions including device identifiers and device functions for one or more of a command for the programmable shower 2 (e.g., select shower sequence or turn on/off shower), a command for the bathtub sensory device 3 (e.g., select a bath experience), a command for the bathtub level device (e.g., select a bath level), a command for the sink faucet 8 (e.g., select a temperature or volume), a command for light guides (e.g., a position or angle for the light), a command for the fan (e.g., a fan speed or on/off), a command for the kitchen faucet 21 (e.g., select a temperature or volume), a command for the dishwasher 22 (e.g., a cleaning mode or on/off), a command for the garbage disposal 23 (e.g., a speed or on/off), the refrigerator 24 (e.g., select a temperature), a command for the water heater 25, (e.g., select a temperature), or a command for the water filter 26 (e.g., activate or deactivate). In addition or in the alternative, data from external device 30 to impact one or more settings of the toilet. In one example, weather data from a weather service is used to determine a temperature for the heater of the toilet seat.

Rather than the direct commands, the auxiliary command for another device may be calculated or determined from sensor data collected at the intelligent toilet 180. There may be a direct correlation between the intelligent toilet 180 and the auxiliary device. The toilet seat may trigger an action in the auxiliary device. For example, when the user sits on the toilet seat, the fan turns on. In another example, when the user sits on the toilet seat a media player (e.g., radio, digital recording, news) plays and when the user stands from the toilet seat the media player stops. The position of the user with respect to the intelligent toilet may trigger a specific action in the auxiliary device. For example, when the user stands from the toilet seat or otherwise steps away from the intelligent toilet, the faucet turns on or a light guide points toward the sink to encourage handwashing. When the sensor data is stool analysis, the result of the analysis may impact a suggestion for a type of food made at a refrigerator.

The control module 183 may generate alerts from the sensor data. For example, when the sensor data indicates a malfunction, an alert is sent to the manufacturer or service provider as the external device 30. When the sensor data relates to urinalysis, an alert may be sent to an employer or doctor as the external device 30.

When the sensor data describes whether the toilet is in use or not, an alert may be sent to another appliance. For example, a television, a refrigerator, or the home hub communication device may provide the alert to the user that the intelligent toilet is in use or not in use. The occupancy may also be provided to phone 181. Multiple toilets may be connected to the network device 14 and server 13. The phone 181 or other devices may provide the occupancy toilets or provide an alert when a least one of the toilets is unoccupied.

Settings data for the auxiliary device may be based on information received at the control module 183 from another of the auxiliary devices. For example, data collected regarding height from a shower setting may be applied to a toilet seat position, a position of the user interface on the mirror substrate or a position of a light guide. Configuration data for the user may be based on the identification of the user or detection of the user and preferences previously established for the user. Type data for the auxiliary device may be used to apply a setting across a class of devices. For example, the user preferences may specify a temperature that is applied to all auxiliary devices with a temperature setting.

In one example, the control module 183 includes the components illustrated by FIG. 9. The control module 183 may include a communication interface configured to send the auxiliary command to the auxiliary device.

The control module 183 may include a speaker configured to provide audio for status data for the auxiliary device, settings data for the auxiliary device, configuration data for the user, or type data for the auxiliary device. The speaker may be movable. The control module 183 may engage a positioning mechanism (e.g., stepper motor or solenoid) to move the speaker toward a user. The degree of movement may depend on the task performed by the user, the identity of the user, the height of the user, the preferences of the user. The volume of the speaker may be configurable. The control module 183 may set a volume of the speaker based on the task performed by the user, the identity of the user, the age of the user, the height of the user, the preferences of the user. For example, volume may be set proportional to age. Certain tasks may invoke higher volumes. For example, when the shower is running a higher volume is used.

The control module 183 may include a microphone configured to collect audio (e.g., voice commands) for settings data for the auxiliary device, configuration data for the user, or type data for the auxiliary device. The microphone may be movable. The control module 183 may engage a positioning mechanism (e.g., stepper motor or solenoid) to move the microphone toward a user. The degree of movement may depend on the task performed by the user, the identity of the user, the height of the user, the preferences of the user. The volume of the microphone may be configurable.

The voice commands received at the control module 183 may include device identifiers that describe the auxiliary device and device functions to be performed by the auxiliary device, which are described herein with respect to various appliances. In addition, the voice commands may include a device identifier for the intelligent toilet, or omitting the device identifier may default to the intelligent toilet, and a device function for the intelligent toilet. Example functions performed at the intelligent toilet may include flushing the toilet, activating or deactivating the seat warmer, activating or deactivating a media player, opening or closing the lid, control of the lights, control of the light guide, selection of the collected data and selection of the displayed data.

The control of the lights (e.g., light strip 186) may include the color of the lights, brightness of the lights, intensity of the lights, or schedule for the lights. The control of the light guide may include an angle or position for the light is determined based on the auxiliary command selected for the user. For example, the voice command may instruct the light guide to illuminate the basin in response to the voice command. The selection of the collected data may enable or disable one or more sensors. The selection of the displayed data may enable or disable the display of external data (e.g., weather) or data received from auxiliary devices.

Configuration data for the intelligent toilet may include configurations for the device that are selected by the user or learned from the user's habits. Example configurations may be a seat position, default position setting for the lid, or interval for the cleaning system. Configuration data may be specific to the size of the user or handedness (e.g., left handed or right handed), which impact how sensor data is recorded (e.g., handedness may impact the collect of sensor data for usage statistics). Settings data for the intelligent toilet may include settings for the components of the intelligent toilet. Example settings include temperature for the foot warmer or seat warmer, volume for the media player, intensity for the light or a delay setting between the time the sensor data is collected and the resulting action is taken (e.g., time between the proximity sensor detect a user and the lid is opened).

Figure 20:
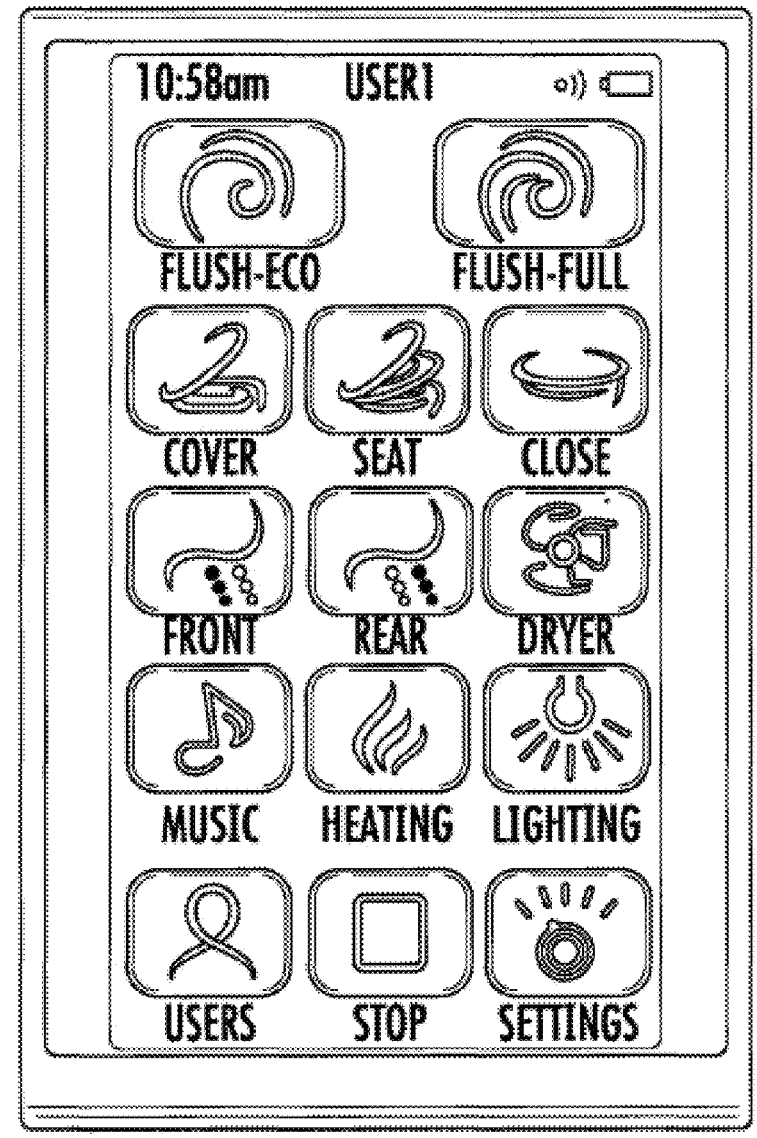
FIG. 20 illustrates a control panel for the home hub communication devices, according to an exemplary embodiment.

FIG. 20 illustrates an example control panel 195 for the home hub communication devices. Control panel 195 may include phone 181 and/or dedicated remote 185. In some embodiments, control panel 195 is a mobile device. The control panel 195 displays multiple inputs or icons to the user. A selection made on the control panel 195 is encoded in a command that may be transmitted directly to the control module 183. Each selection on the control panel 195 may correspond to a similar voice command having a device identifier and a device function. The command may be transmitted to the network device 14 and/or server 13, which relays the command to the intelligent toilet. The control panel 195 may additionally or alternatively control other appliances according to any of the examples herein. The control panel 195 may be a phone, tablet, watch, or wearable device. The control panel 195 may physically connect to one or more of the bath room or kitchen appliances (i.e., the control panel 195 may physically connect (e.g., snap) to one appliance, be removed, and subsequently be physically connected to another appliance).

Kitchen Appliances

Figure 21:
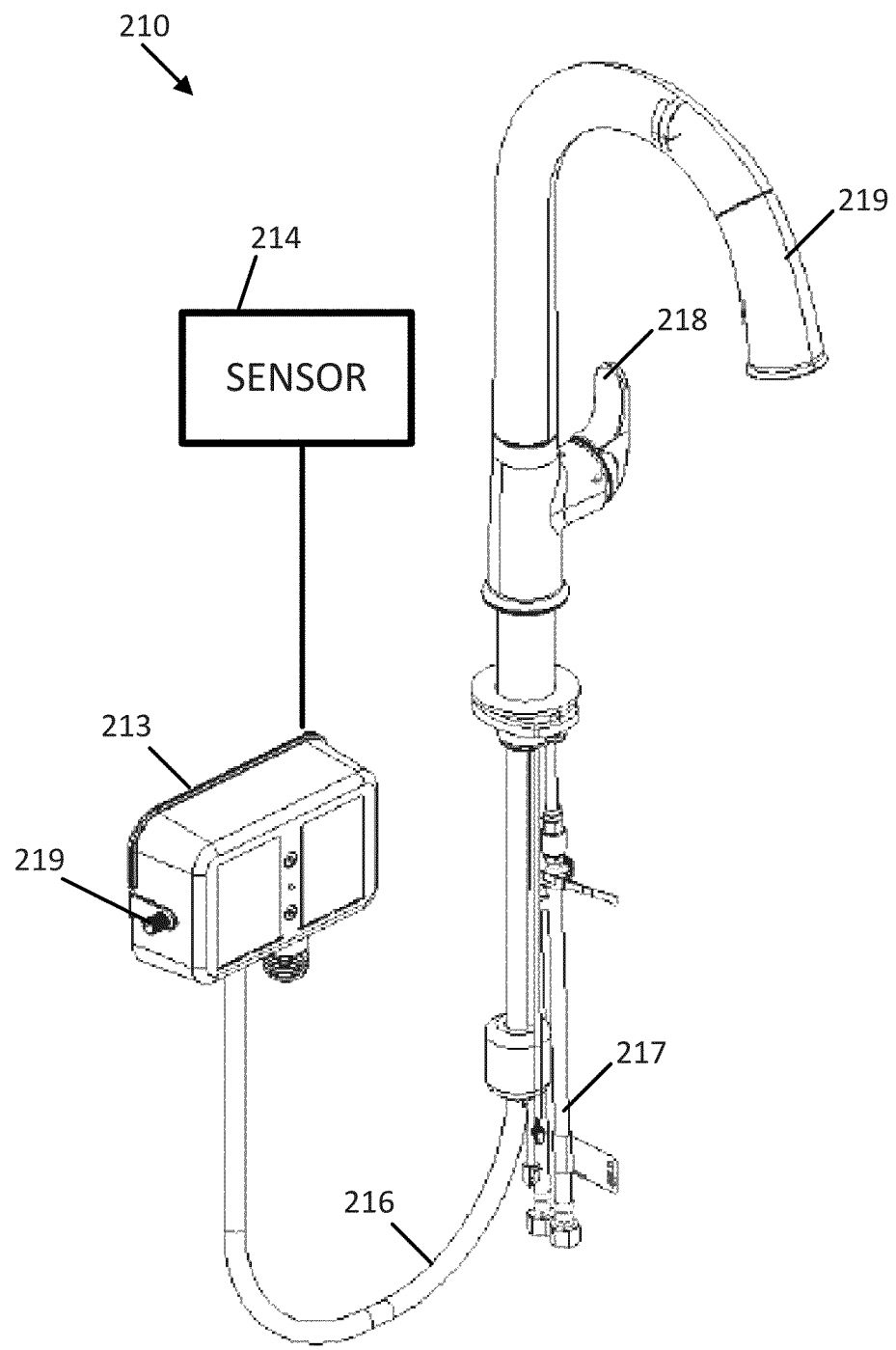
FIG. 21 illustrates a kitchen appliance including a home hub communication device, according to an exemplary embodiment.

FIG. 21 illustrates a kitchen appliance 210 including a home hub communication device, according to an exemplary embodiment. The kitchen appliance 210 includes at least a control module 213, a sensor 214, and a communication interface configured to communication with the network device 14 and the server 13. In one example, the kitchen appliance 210 is a kitchen faucet including water inlet pipes 217, a handle 218, and a removable sprayer 219 with handle grip. The handle 218 controls one or more valves for on/off and temperature control. The control module 213 may electrically connect with sensors and/or valves in the faucet through conduit 216 which includes one or more wires or electrical conductors. The sensor 214 may be in the faucet and may be aligned with the window to detect motion outside of the faucet. The control module 213 may control one or more valves to control water flow (e.g., volume, temperature, duration), and the one or more valves may be internal to the control module 213 or in the faucet itself. The control module 213 may include a manual bypass switch 209 for disabling the control module 213 and/or electronic control of the faucet. Additional, different, or fewer components may be included.

The kitchen appliance 210 is a water consuming device connected to a water supply through one or more conduits or pipes. Examples include a kitchen faucet, a dishwasher, a refrigerator, a water heater, and a water filter. Each of the kitchen appliances is configured to collect data indicative of a user, communicate the data indicative of the user to another appliance either directly or indirectly, and provide services to user based on data indicative of the user that is received from other appliances.

The sensor data collected by the sensor 214 may describe the water of the kitchen appliance 210 or describe the user near the kitchen appliance 210. For detecting the water, the sensor 214 may be located in the water flow of the kitchen appliance 210. The sensor 214 may be a water quality sensor including pH sensor, oxygen sensor, or another chemical sensor. The sensor 214 may be implemented using one or more screens or filters for detecting particulates in the water. For example, a graphene mesh may include holes of a predetermined size sized for different materials.

The sensor 214 may be a flow sensor, which is a pressure sensor, ultrasonic sensor or light sensor. The light sensor may measure the quantity of water that passes a light beam. The ultrasonic sensor generates an ultrasonic wave that travels through the flow of water and is received at a received. Based on the received ultrasonic wave the volume and/or speed of the flow of water is detected. The sensor 214 may be paired with two polished surface that reflects the ultrasonic wave or the light beam on the opposite side of the flow of water and returns the ultrasonic wave or the light beam to the sensor 214.

For detecting the user, the sensor 214 may be a proximity sensor (e.g., infrared sensor) or an image collection device described herein. For example, the sensor 214 may be mounted in a neck of a faucet and may detect a gesture or presence of a hand near the neck of the faucet to activate or deactivate the flow of water through the faucet. Alternatively or in addition, the sensor 214 may detect the position or identity of the user as described herein.

The control module 213 may select, based on the analysis of the sensor data, an auxiliary command for an auxiliary device coordinated with the kitchen appliance. The auxiliary command may be selected for a particular user. The auxiliary command for the auxiliary device is based on the instruction from the user received at the user interface and the data displayed at the user interface includes status data for the auxiliary device, settings data for the auxiliary device, configuration data for the user, or type data for the auxiliary device.

The analysis of the sensor data may determine an instruction received via voice command or user interface. For example, the user may enter a command for the programmable shower 2 (e.g., select shower sequence or turn on/off shower), a command for the bathtub sensory device 3 (e.g., select a bath experience), a command for the bathtub level device (e.g., select a bath level), a command for the intelligent toilet 6 (e.g., flush or close the lid), a command for the toilet seat 7 (e.g., raise or lower the toilet seat), a command for the sink faucet 8 (e.g., select a temperature or volume), a command for light guides (e.g., a position or angle for the light), a command for the fan (e.g., a fan speed or on/off), a command for kitchen faucet 21 (e.g., select a temperature or volume), a command for the dishwasher 22 (e.g., a cleaning mode or on/off), a command for the garbage disposal 23 (e.g., a speed or on/off), a command for the refrigerator 24

(e.g., select a temperature), a command for the water heater 25, (e.g., select a temperature), or a command for the water filter 26 (e.g., activate or deactivate).

Settings data for the auxiliary device may be based on information received at the control module 213 from another of the auxiliary devices. For example, data collected regarding water temperature from a shower setting or a bathroom sink may be applied to a kitchen sink. Configuration data for the user may be based on the identification of the user or detection of the user and preferences previously established for the user. Type data for the auxiliary device may be used to apply a setting across a class of devices. For example, the user preferences may specify a temperature that is applied to all auxiliary devices with a temperature setting.

In one example, the control module 213 includes the components illustrated by FIG. 9. The control module 213 may include a communication interface configured to send the auxiliary command to the auxiliary device.

The control module 213 may include a speaker configured to provide audio for status data for the auxiliary device, settings data for the auxiliary device, configuration data for the user, or type data for the auxiliary device. The speaker may be movable. The control module 213 may engage a positioning mechanism (e.g., stepper motor or solenoid) to move the speaker toward a user. The degree of movement may depend on the task performed by the user, the identity of the user, the height of the user, the preferences of the user. The volume of the speaker may be configurable. The control module 213 may set a volume of the speaker based on the task performed by the user, the identity of the user, the age of the user, the height of the user, the preferences of the user. For example, volume may be set proportional to age. Certain tasks may invoke higher volumes. For example, when the kitchen appliance 210 is running a higher volume is used.

The control module 213 may include a microphone configured to collect audio (e.g., voice commands) for settings data for the auxiliary device, configuration data for the user, or type data for the auxiliary device. The microphone may be movable. The control module 213 may engage a positioning mechanism (e.g., stepper motor or solenoid) to move the microphone toward a user. The degree of movement may depend on the task performed by the user, the identity of the user, the height of the user, the preferences of the user. The volume of the microphone may be configurable.

The voice commands received at the control module 213 may include device identifiers that describe the auxiliary device and device functions to be performed by the auxiliary device, which are described herein with respect to various appliances. In addition, the voice commands may include a device identifier for the kitchen appliance 210, or omitting the device identifier may default to the kitchen appliance 210, and a device function for the kitchen appliance 210. Example functions performed at the kitchen appliance 210 may include selection of the temperature of the water, selection of a water supplement, selection of a water filter, selection of the displayed data, and control of a light guide.

The control of the light may include the color of the lights, brightness of the lights, intensity of the lights, or schedule for the lights. The control of the light guide may include an angle or position for the light is determined based on the auxiliary command selected for the user. For example, the voice command may instruct the light guide to illuminate handwashing in response to the voice command. The selection of the collected data may enable or disable one or more sensors. The selection of the displayed data may enable or disable the display of external data (e.g., weather) or data received from auxiliary devices.

The kitchen appliance 210 may select a supplement mode or filtering mode based on sensor data received from another device. The supplement mode may insert a supplement into the water. The supplements may include fluoride, vitamins, nutrients, medicines, or other substances. The supplement mode may be activated or modified in response to sensor data collected at the kitchen appliance 210 or other appliances.

For example, the kitchen appliance 210 may detect the makeup of the water and select the supplement based on deficiencies in the water. In another example, the condition of the user is detected at other appliances (e.g., the mirror assembly or the intelligent toilet). The condition of the user may be malnutrition, which is treated by vitamin supplements added to the water. The condition of the user may be a sickness, which is treated by medicine supplements add to the water.

Intelligent Shower

Figure 22:
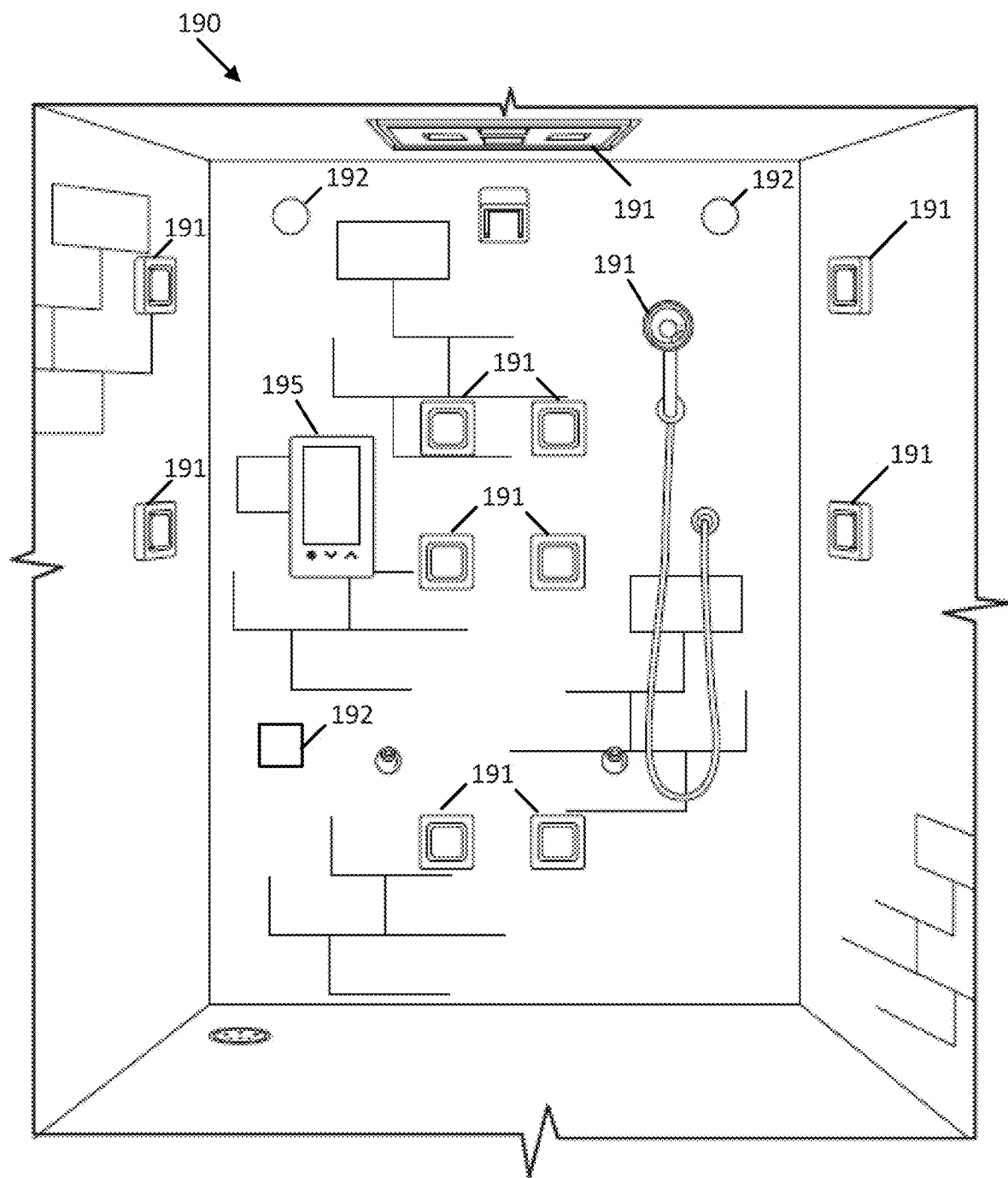
FIG. 22 illustrates a shower device including a home hub communication device, according to an exemplary embodiment.

FIG. 22 illustrates a shower 190 including a home hub communication device, according to an exemplary embodiment. The shower 190 includes a shower enclosure and several shower subsystems (i.e., a water subsystem, an audio subsystem, a steam subsystem, a lighting subsystem, etc.). Each of the shower subsystems has output devices (e.g., shower outlets, flow control valves, temperature control valves, solenoids associated with the valves, lighting devices, audio output systems, steam outlets, etc.) configured to provide a user of the shower with an enhanced showering experience. The shower 190 may include multiple water dispensers 191, sensors 192, and at least one control panel 195.

The control panel 195 includes an electronic display. The electronic display is configured to display graphical user interfaces for allowing user control of the various shower subsystems and/or shower output devices. A controller is in communication with the electronic display and causes the graphical user interfaces to be presented via the electronic display. In various embodiments, the controller may be integrated with the control panel 195, physically separate from the control panel 195, or partially integrated and partially separate from the control panel 195. The control panel 195 may include a touch-sensitive panel overlaying the electronic display (e.g., a capacitive touch screen), manually-operable buttons (e.g., capacitive touch buttons), and/or other user input devices configured to receive user input and provide the user input to the controller. The control panel 195 (e.g., via the controller) controls the various components of the shower in response to the user inputs (e.g., signals or data representing the user inputs) received at the user input devices.

A shower control system is provided for receiving and processing user inputs, displaying a graphical user interface on the electronic display, and controlling outputs of the various output devices. The shower control system advantageously includes software that causes the generation and display of intuitive graphical user interfaces for providing an intuitive and powerful control experience to the user. Settings and combinations of settings may be saved in the shower control system (e.g., a controller of the system) for later playback (e.g., execution) by a controller of the shower control system. Such playback or execution causes actuation, adjustment, or another state change of one or a plurality of the shower output devices.

Shower 190 includes a water subsystem having various output devices (i.e., shower outlets) located within the shower enclosure. For example, shower 190 is shown to include multiple water dispensers 191 including a front showerhead, a left showerhead, a right showerhead, an upper body spray, a middle body spray, a lower body spray, side body sprays, a handshower, and a rainhead. In various embodiments, the water subsystem or set of output devices may include any number or combinations of output devices. For example, in an alternative exemplary embodiment, the water subsystem may include a central body spray (e.g., a vertical column of shower outlets) in place of upper body spray and middle body spray. In another exemplary embodiment, the left showerhead and right showerhead may be located on front wall. Shower outlets may be located on any of surfaces and may include additional or fewer shower outlets in various embodiments.

The water subsystem may include one or more analog or digital valves. Valves of the system may be configured to allow for an electronically controlled mixing of hot and cold water. Such mixing can allow control systems and methods described herein to achieve or approach certain target temperatures. Valves of the system may also be configured to allow for electronically controlled or selected shower outlet water flow. The electronically controlled valves (e.g., solenoids for actuating the hydraulic valves) are controlled via control signals from one or more controllers of the shower control systems described throughout this disclosure. The valves may be used to independently control flow volume to each of shower outlets.

In some embodiments, the water subsystem includes multiple different temperature control valves (e.g., thermostatic valves). Each temperature control valve may have a plurality of outlet ports (e.g., three outlet ports, six outlet ports, etc.). A first temperature control valve may control the temperature of water provided to a first subset of shower outlets and a second temperature control valve may control the temperature of water provided to a second subset of shower outlets. For example, a first temperature control valve may control the temperature of water provided to shower outlets, whereas a second temperature control valve may control the temperature of water provided to other shower outlets. Advantageously, using multiple different temperature control valves allows the water from different shower outlets to have different temperatures. In other embodiments, a single temperature control valve is used to control the temperature of water provided to the various shower outlets. In various embodiments, any number of temperature control valves may be used to define any number of temperature zones.

In some embodiments, shower 190 includes a steam subsystem. The steam subsystem includes steam outlets that receive steam from a steam generator in fluid communication with steam outlets. The steam generator is disposed between, and coupled via conduit (e.g., piping or tubing), to steam outlets and a water supply. The steam generator heats the water, turning it into steam that is then communicated into shower enclosure through the steam outlets. The steam generator may be controlled via control signals from one or more controllers of the shower control systems described throughout this disclosure.

In some embodiments, shower 190 includes a music subsystem. The music subsystem includes speakers, an amplifier, and a media player. The amplifier, media player, and other components may be located proximate to or remote from shower enclosure. The music subsystem is configured to communicate sound into shower enclosure. The music subsystem (e.g., a media player thereof) may be controlled via control signals from one or more controllers of the shower control systems described throughout this disclosure.

In some embodiments, shower 190 includes a lighting subsystem. The lighting subsystem includes one or more lights, such as conventional light bulbs (e.g., incandescent, LED, fluorescent) or a plurality of colored lights configured for use as a lighted rain panel used for chromatherapy. In some embodiments, lights are integrated with rainhead. The lighting subsystem is configured to selectively supply light into shower enclosure. The lighting subsystem (e.g., particular switches for the lights, dimmers for the lights, etc.) may be controlled via control signals from one or more controllers of the shower control systems described throughout this disclosure.

In some embodiments, a control panel 195 is configured to receive user inputs for controlling the shower subsystems and for communicating settings and status information of the shower subsystems to a user. Control panel 195 generally includes a housing and an electronic display (e.g., an LCD panel). The housing includes various attachment points (e.g., brackets, fasteners, portions for receiving screw heads, etc.) for mounting control panel 195 within shower enclosure. The housing also provides a waterproof casing to protect electronic display and associated internal electronic components from moisture. A touch-sensitive panel (e.g., a capacitive touch panel) may also be provided on the housing for receiving user inputs. A portion of the touch-sensitive panel may overlay electronic display to provide a touchscreen interface. The electronic display can be caused to display graphical user interfaces and to receive user inputs via the touch screen interface.

Figure 23:
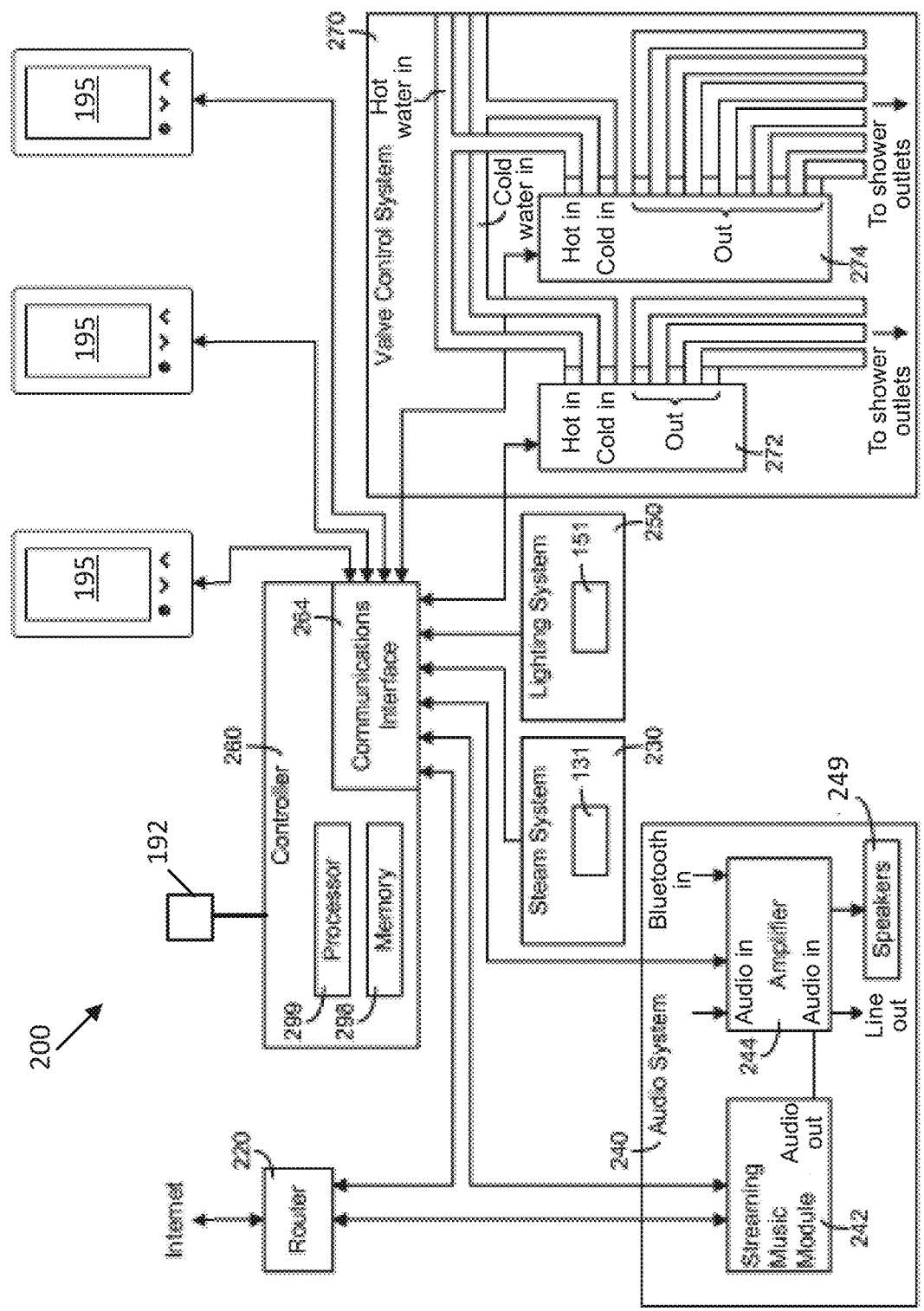
FIG. 23 illustrates a communication system for the home hub communication device FIG. 22, according to an exemplary embodiment.

Referring now to FIG. 23, a block diagram of a shower control system 200 is shown, according to an exemplary embodiment, which is another example of a home hub communication device. Shower control system 200 generally refers to the electronics involved in processing and communicating signals for controlling shower subsystems 230-270 according to user inputs, but may also refer to any of the controlled shower subsystems 230-270 or shower output devices themselves. Shower control system 200 receives indications to change conditions of the various output devices (e.g., from the user input devices) and acts upon the indications by sending signals to control panels 195, shower subsystems 230-270, and/or devices/controllers thereof.

Shower control system 200 includes a controller 260 in communication with one or more control panels 195. Each of control panels 195 may be disposed at a different location (e.g., in shower, outside shower, etc.) for facilitating user interaction with shower control system 200 at multiple different locations. In various embodiments, controller 260 may be integrated with one or more of control panels 195 or separate from control panels 195. Controller 260 may receive input from control panels 195 (e.g., via communications interface 264) and may control the user interface outputs provided via electronic display 161. Controller 260 processes user inputs received at control panels 195 (e.g., user inputs received via a touchscreen, buttons, switches, or other user input devices of control panel 195) and provides control outputs to shower subsystems 230-270 based on the user inputs.

Controller 260 communicates with shower subsystems 230-270 and/or the devices thereof (e.g., shower outlets, speakers, lights, valves, etc.) for controlling the various output devices. For example, controller 260 may receive an indication to adjust the temperature of the water provided by one or more of shower outlets (e.g., based on user input received at a touch panel interface), and act upon the indication by causing water with increased temperature to flow through the shower outlet (e.g., by sending an appropriate control signal to the appropriate mixing valve subsystem). Commands received at controller 260 from the microphone or other appliances may include device identifiers that identify one or more of the shower subsystems 230-270 and device functions for one or more functions performed at the shower subsystems 230-270.

Controller 260 may cause electronic display to indicate a target water temperature, an actual water temperature, and indication of whether the actual water temperature is rising or falling. Controller 260 may cause electronic display to indicate the requested and completed adjustment in temperature.

In some embodiments, controller 260 is configured to receive signals from control panels 195, steam system 230 including a steam emitter 131, audio system 240, lighting system 250 including a lighting device 151, valve control system 270 (e.g., electronic valves 272-274), and/or other subsystems or devices of shower control system 200 or external devices (e.g., router 220). Controller 260 processes and acts upon the received signals. Controller 260 may act upon signals received by sending control signals to steam system 230, audio system 240, and lighting system 250. Controller 260 may also act upon signals received by sending control signals to valve control system 270 (e.g., electronic valves 272-274) or other shower subsystem components. The audio system may include a streaming music module 242, an amplifier 244, and one or more speakers 249.

Controller 260 is shown to include a communications interface 264, a processor 299, and memory 298. Communications interface 264 may include wired or wireless interfaces (e.g., jacks, antennas, transmitters, receivers, transceivers, wire terminals, etc.) for conducting data communications with various systems, devices, or networks. For example, communications interface 264 can include an Ethernet card and port for sending and receiving data via an Ethernet-based communications network and/or a Wi-Fi transceiver for communicating via a wireless communications network. Communications interface 264 may be configured to communicate via local area networks (e.g., a home network, a LAN, etc.) or wide area networks (e.g., the Internet, a WAN, etc.).

Still referring to FIG. 23, shower control system 200 is shown to include a valve control system 270. According to an exemplary embodiment, one or more digital valves 272-274 are configured to selectively mix hot and cold water and selectively control water output to shower outlets 121-129. Each digital valve 272-274 may be arranged between shower outlets (water dispensers 191) and hot and cold water supplies. In an exemplary embodiment, valves 272-274 include a thermostatic mixing component (e.g., for controlling temperature) and/or one or more electrically-actuated solenoids (e.g., for controlling flow volume). In some embodiments, valve control system 270 includes one or more sensors for measuring temperature, valve position, and/or water pressure upstream or downstream of valves 272-274. The sensors may send signals with condition information to controller 260, which then processes the signals, and acts upon them.

Valves 272-274 may be electrically operated. In some embodiments, controller 260 controls operation of valves 272-274. Controller 260 may operate each of valves 272-274 independently to achieve multiple different water temperatures simultaneously. For example, controller 260 may cause valve 272 to output water having a first temperature and may cause valve 274 to output water having a second temperature, different from the first temperature.

In some embodiments, the hot and cold water inlets of valves 272-274 are coupled via a conduit (e.g., piping or tubing) to hot and cold water supplies, respectively. Valves 272-274 may be actuated by controller 260 and/or a separate valve driver circuit. Valves 272-274 may be configured to control an amount of hot and cold water allowed to pass through valves 272-274 to achieve a specified water temperature. Each of valves 272-274 may be independently connected to the hot and cold water supplies and may be operated independently to control the temperature of the water provided to a subset of shower outlets (water dispensers 191).

In some embodiments, each of valves 272-274 is connected (e.g., via piping or tubing) to one or more of shower outlets (water dispensers 191). Valves 272-274 may be actuated by controller 260 and/or a separate valve driver circuit to selectively open and close to control an amount of water (e.g., a flow rate) provided to each of shower outlets (water dispensers 191). Valve 272 is shown to include three outlet ports and valve 274 is shown to include six outlet ports. Each of the outlet ports may be opened and closed independently (e.g., via a solenoid or outlet valve) to independently control the flow rate of water provided to each of shower outlets (water dispensers 191).

In some embodiments, valves 272-274 do not include outlet valves. Instead, outlet valves may be disposed between valves 272-274 and shower outlets (water dispensers 191), may be attached directly to shower outlets 121-129, or may be integral with shower outlets 121-129. According to another exemplary embodiment, valves 272-274 are attached directly to or are integral with shower outlets (water dispensers 191), eliminating the need for outlet valves.

Still referring to FIG. 23, shower control system 200 is shown to include a steam system 230, an audio system 240, and a lighting system 250. In some embodiments, the control electronics (e.g., controller, microprocessor, data interface) for one or more of subsystems 230-250 may be integral with each other and/or combined with controller 260. For example, controller 260 may include the control electronics for lighting system 250, audio system 240, and/or other subsystems of shower control system 200, thus obviating the need for separate system control electronics. In other embodiments, each subsystem may include a controller and data interface that is configured for receiving signals, processing those signals, and acting upon received signals. Steam system 230, audio system 240, and/or lighting system 250 may include sensors for detecting conditions of the respective systems, such as temperature, humidity, volume, and luminosity.

The sensor data collected by the sensor 192 may describe the water of the shower 190 or describe the user in the shower 190. For detecting the water, the sensor 192 may be located in the valve control system 270. The sensor 214 may be a water quality sensor including pH sensor, oxygen sensor, or another chemical sensor.

The sensor 192 may be a flow sensor, which is a pressure sensor, ultrasonic sensor or light sensor. The light sensor may measure the quantity of water that passes a light beam. The ultrasonic sensor generates an ultrasonic wave that travels through the flow of water and is received at a received. Based on the received ultrasonic wave the volume and/or speed of the flow of water is detected. The sensor 192 may be paired with two polished surface that reflects the ultrasonic wave or the light beam on the opposite side of the flow of water and returns the ultrasonic wave or the light beam to the sensor 192.

For detecting the user, the sensor 192 may be a proximity sensor (e.g., infrared sensor) or an image collection device described herein. For example, the sensor 192 may be mounted at a faucet or water dispenser 191 and may detect a gesture or presence of a hand to activate or deactivate the flow of water through the faucet. Alternatively or in addition, the sensor 192 may detect the position or identity of the user as described herein.

One or more sensors 192 may determine volume or weight of the user by imaging or detecting the user from multiple angles. BMI calculations from the volume or weight may be sent to the home hub communication device to be sent to other appliances. The sensors 192 may include other sensors for vital information such as temperature, heart rate, or breathing rate.

The controller 260 may select, based on the analysis of the sensor data, an auxiliary command for an auxiliary device coordinated with the shower 190. The auxiliary command may be selected for a particular user. The auxiliary command for the auxiliary device is based on the instruction from the user received at the user interface and the data displayed at the user interface includes status data for the auxiliary device, settings data for the auxiliary device, configuration data for the user, or type data for the auxiliary device.

The analysis of the sensor data may determine an instruction received at the controller 260. For example, the user may enter a command for the bathtub sensory device 3 (e.g., select a bath experience), a command for the bathtub level device (e.g., select a bath level), a command for the intelligent toilet 6 (e.g., flush or close the lid), a command for the toilet seat 7 (e.g., raise or lower the toilet seat), a command for the sink faucet 8 (e.g., select a temperature or volume), a command for light guides (e.g., a position or angle for the light), a command for the fan (e.g., a fan speed or on/off), a command for kitchen faucet 21 (e.g., select a temperature or volume), a command for the dishwasher 22 (e.g., a cleaning mode or on/off), a command for the garbage disposal 23 (e.g., a speed or on/off), a command for the refrigerator 24 (e.g., select a temperature), a command for the water heater 25, (e.g., select a temperature), a command for or the water filter 26 (e.g., activate or deactivate).

Settings data for the auxiliary device may be based on information received at the controller 260 from another of the auxiliary devices. For example, data collected regarding height from a shower setting may be applied to a toilet seat position, a position of the user interface on the mirror substrate or a position of a light guide. Configuration data for the user may be based on the identification of the user or detection of the user and preferences previously established for the user. Type data for the auxiliary device may be used to apply a setting across a class of devices. For example, the user preferences may specify a temperature that is applied to all auxiliary devices with a temperature setting.

The controller 260 may control a shower sequence. In one example, the shower sequence involves a combination of a series of pressure settings for the water dispensers 191, a series of temperature settings for the water dispensers 191, a series of pulse settings for the water dispensers 191, a series of activating or deactivating the water dispensers 191, or other settings. The shower sequence may be selected according to the user identity, a user preference, or learned over time for the user based on historical data. The controller 260 accesses the user configuration and controls the water dispensers 191 to adjust settings accordingly. The user configuration may include a series of settings (e.g., temperature, pressure, pulses) associated with time intervals. The controller 260 may apply the shower at a first setting for a first time interval and a second setting for a second time interval.

The controller 260 may regulate water usage by controlling the water dispensers 191. The temperature of the shower, pressure of the shower, or number of active water dispensers 191 may be controlled to encourage the user to reduce water consumption and stop the shower. The user may be encouraged to stop the shower when the temperature is too high or not many water dispensers 191 are working. The controller 260 may access a water usage threshold from the user configuration. The controller 260 may calculate the water usage threshold based on local conditions received from the external device 30 (e.g., drought conditions, time of year, reservoir levels, or local municipal ordinances or guidelines).

In one example, the controller 260 includes the components illustrated by FIG. 9. The controller 260 may include a communication interface configured to send the auxiliary command to the auxiliary device.

The controller 260 may be coupled with a speaker configured to provide audio for status data for the auxiliary device, settings data for the auxiliary device, configuration data for the user, or type data for the auxiliary device. The speaker may be movable. The control module 123 may engage a positioning mechanism (e.g., stepper motor or solenoid) to move the speaker as described in other embodiments.

The controller 260 may be coupled with a microphone configured to collect audio (e.g., voice commands) for settings data for the auxiliary device, configuration data for the user, or type data for the auxiliary device. The microphone may be movable as described in other embodiments. The volume of the microphone may be configurable.

The voice commands received at the controller 260 may include device identifiers that describe the auxiliary device and device functions to be performed by the auxiliary device, which are described herein with respect to various appliances. In addition, the voice commands may include a device identifier for the shower 190. In another example, the lack of the device identifier may default to the shower 190. The voice commands may include a device function for the shower 190. Example functions performed at the shower 190 may include control of the lighting system 250, control of the steam system 230, control of the valve control system 270, and control of the audio system 240. For example, the voice command may instruct the lighting system 250 to illuminate the shower 190 or a particular water dispenser 191. The voice command may activate or deactivate a particular water dispenser 191.

Some systems may include one or more modules which may aggregate various user data and information, which can then be used in various ways. In one example, information may be manually entered or automatically gathered, such as via an app or web module on a user device (such as a cellular phone, computer, tablet, or other user device). This information may, in some instances, be shared with other third parties. A user may set and/or control the parameters for sharing or exchange of said information with a third party. A user may control a list of authorized third parties that can view certain stored information, and/or what information is shared. For example, a user may choose to provide certain health-related information (such as weight, blood pressure, heart rate) to a medical provider or physician, but may choose not to provide certain other information (such as shower preferences, urinalysis, or grooming habits). In some instances, the third party may be able to communicate directly to the user, such as before, during, or after viewing the user's information. The third party may be allowed to provide feedback or additional communications (such as medical advice) to the user through the same web module or app. In some embodiments, users may be able to share certain information with third parties in an anonymous fashion, such that the user's information will not be specifically traceable to the user, but may provide useful information to a third party (such as trends over certain demographics of the population). Many other variations are possible.

Intelligent Bathtub

Figure 24:
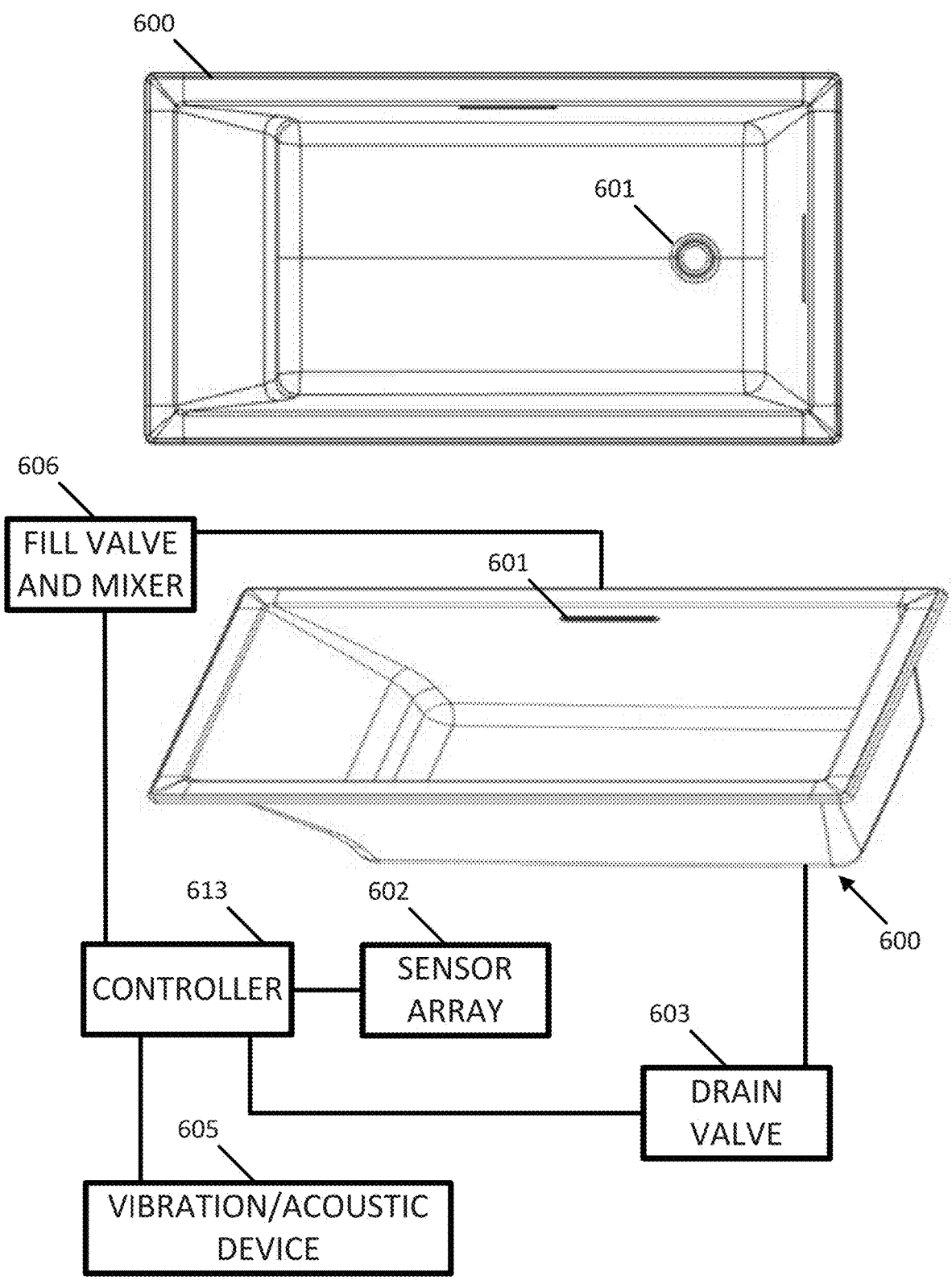
FIG. 24 illustrates a bathtub including a home hub communication device, according to an exemplary embodiment.

FIG. 24 illustrates a bathtub 600 including a home hub communication device, according to an exemplary embodiment. The bathtub 600 may include a bathtub automatic leveling system, a bathtub automatic maintaining temperature system, a bubble massage system, a heated surface system, an aromatherapy system, a lighted system, a fog or mist generating system, chromatherapy, whirlpool, a vibration acoustic system, or a combination of any of the systems mentioned above. A bathtub 600 may include an integral fill 601, an electronic fill mixer valve 606, a sensor array 602, a drain and drain valve 603, a vibration acoustic device 605, and a controller 613. Additional, different, or fewer components are included.

The controller 613 is configured to operate the one or more drain valves 603 using an electronic drain control algorithm and/or drain valve 603. The controller 613 may automatically operate the drain to empty the bathtub 600 after it detects a person has left the bath through bath sensory devices or/and other devices. The controller 613 can be user defined to activate or deactivate the autodrain feature and set a user time delay for autodrain activation. The drain valve 603 may be responsive to a pulse width modulated signal indicative of an angle of the valve or a proportion of fully opening (e.g., 50% open, 80% open) for the valve. The drain valve 603 may include any number of independently operating valves and the pulse width modulated signal may control multiple valves. The drain valve may also be operated by DC voltage or specific current. The drain might have an integral valve and could be able to open and close electronically by command from the controller 613. The drain valve 603 may house some or all of the sensor array in terms of physical location or in terms of providing sensory tapping points.

The vibration acoustic device 605 may include one or more speakers for delivery a predetermined sequence of audio and/or vibrations to the bathtub 600. Similar to the vibration acoustic device 605, the controller 613 can control other bathtub experiences such as chromatherapy, bask heated surface, bubble massage, and other experiences. The controller 613 is configured to generate and provide a control signal to the vibration acoustic device 605. The vibration acoustic device 605 may include a speaker or a transducer to broadcast sound waves that travel through the water of the bathtub 600 and to the body. The transducers are strategically positioned within the shell of the bathtub 600, providing the most beneficial effects to the entire body, while leaving the bathing surface smooth and uninterrupted. The controller 613 may send the control signal to the vibration acoustic device 605 according to an audio file such as music. Alternatively, the control panel may be a sequence of pulses corresponding to varying vibration levels. The vibration acoustic device 605 also may have Bluetooth or Wi-Fi connectivity and may stream music from paired $3^{rd}$ party devices to play in the bath speakers.

The vibration acoustic device 605 may include speakers mounted on the bathtub 600 in multiple zones. Selection of the zones may be user configurations learned based on historical data or directly selected by the user. The zones may be associate with particular parts of the body. The activation of the zones may vary according with the water level. The controller 613 may determine particular sequences or styles of music or vibration that the user prefers for particular physical conditions.

The sensor array 602 may include a level sensor to detect the water level in the bathtub 600. The level sensor may be a specific gravity sensor having a float. The float may be displaced to a position that is detected electrically or by position. The force needed to support a column of material that is displaced decreases by the weight of the process fluid displaced. A force transducer measures the support force and reports it as an analog signal. The level sensor may include a magnetic sensor including a float. As the float moves up and down a coupled magnet is detected by a magnetic sensor.

The level sensor may include a pressure transducer. The level sensor may include a silicon or piezoelectric diaphragm surface that changes its resistivity as it expands and contracts due to pressure from a low point in the bathtub connected to the sensor via tubing. A column of solid material is suspended in the vessel and based on density, sinks to the lowest level to be measured. Alternatively, differential pressure sensors may measure the pressure at the bottom of the bathtub 600 versus a reference level. The level sensor may be an ultrasonic level sensor, a laser level sensor, or a radar sensor.

The level sensor may determine an identity of the user based on the mass of the user. The level sensor may use algorithms that may include derivatives to detect when a user enters the bath and/or exits the bath and use that to initiate other connected appliances or experiences—for example change the lighting or automatically drain after a preset time. The controller 613 may record the water level detected by the level sensor before the user enters the bath and the water level after the user enters the bath. The difference between the water levels is proportional to the mass of the user and/or is an identifying characteristic of the user. The controller 613 may determine whether and when the user enters the bath based on other sensor data from a proximity sensor. The sensor data from the proximity sensor may also determine how much of the user's body is submerged in the water and adjust the water level calculations accordingly. The level sensor through smaller deviations may measure the breath patterns of the user or heart rate of the user, which are health factors for monitoring the user, and also are identifying characteristics of the user. The controller 613 can use this collected user data to alter the bath experiences automatically based on predefined or dynamically learning algorithms.

The sensor array 602 or/and the electronic fill valve 606 may include a flow sensor configured to measure the flow of water into the bathtub 600. The sensor array 602 may include an image collection device. The sensor array 602 may include environment sensors such as a temperature sensor, humidity sensor, or a pressure sensor. The sensor array 602 may include heart rate sensor. The sensor array 602 may include blood pressure sensor. The sensor array 602 may include a pressure switch that activates the drain valve 603 to open directly acting as an overflow protection for the bath. The sensor array 602 may include facial recognition.

The sensor array 602 may include proximity sensors to detect the height of the user and may use that as an identifying characteristic of the user. The sensor array 602 may use an object detection sensor to detect if there are objects, pets, or people in the bath. The sensor array 602 may include a voice input device or microphone. The controller 613 may use algorithms to analyze data from different sensor array 602 inputs to initiate auxiliary commands. In one example, the controller 613 may detect leaks, detect falls, or detect someone in distress, and prompt the controller 613 to command action from auxiliary devices, such as call the emergency services.

The controller 613 may select, based on the analysis of the sensor data, an auxiliary command for an auxiliary device coordinated with the bathtub 600. The auxiliary command may be selected for a particular user. The auxiliary command for the auxiliary device is based on the instruction from the user received at the user interface and the data displayed at the user interface includes status data for the auxiliary device, settings data for the auxiliary device, configuration data for the user, or type data for the auxiliary device.

The analysis of the sensor data may determine an instruction received at a remote (e.g., phone) or other user interface for the bathtub such as a command for the bathtub sensory device 3 (e.g., select a bath experience), a command for the bathtub level device (e.g., select a bath level) or for another appliance. For example, the user may enter a command at the bathtub 600 for the programmable shower 2 (e.g., select shower sequence or turn on/off shower), a command for the intelligent toilet 6 (e.g., flush or close the lid), a command for the toilet seat 7 (e.g., raise or lower the toilet seat), a command for the sink faucet 8 (e.g., select a temperature or volume), a command for light guides (e.g., a position or angle for the light), a command for the fan (e.g., a fan speed or on/off), a command for kitchen faucet 21 (e.g., select a temperature or volume), a command for the dishwasher 22 (e.g., a cleaning mode or on/off), a command for the garbage disposal 23 (e.g., a speed or on/off), a command for the refrigerator 24 (e.g., select a temperature), a command for the water heater 25, (e.g., select a temperature), or a command for the water filter 26 (e.g., activate or deactivate).

Settings data for the auxiliary device may be based on information received at the controller 613 from another of the auxiliary devices. For example, data collected regarding height from a shower setting may be applied to a water level (e.g., taller people may be associated with high water levels, and wider people may be associated with lower water levels). Configuration data for the user may be based on the identification of the user or detection of the user and preferences previously established for the user. Type data for the auxiliary device may be used to apply a setting across a class of devices. For example, the user preferences may specify a temperature that is applied to all auxiliary devices with a temperature setting (e.g., temperature settings from the shower are applied by the bathtub 600). In another example, the vibration acoustic device 605 may selected an audio recording or a sequence of vibration pulses based on a temporary characteristic of the user such as mood, stress, exercise level, or temperature as determined by the mirror assembly 1 or another appliance.

In one example, the controller 613 included the components illustrated by FIG. 9. The controller 613 may include a communication interface configured to send the auxiliary command to the auxiliary device. The controller 613 may include a speaker configured to provide audio for status data for the auxiliary device, settings data for the auxiliary device, configuration data for the user, or type data for the auxiliary device. The speaker may be movable. The controller 613 may engage a positioning mechanism (e.g., stepper motor or solenoid) according to other embodiments herein. The volume of the speaker may be configurable. The controller 613 may set a volume of the speaker based on the task performed by the user, the identity of the user, the age of the user, the height of the user, the preferences of the user. For example, volume may be set proportional to age. Certain tasks may invoke higher volumes. For example, when the bathtub 600 is running a higher volume is used.

The controller 613 may track the volume and/or size and/or height of the user may be used to predict the age of the user. Device functions at the bathtub may be limited based on age. For example, children may be prohibited from turning on the water. Device functions at other devices may be enabled or disabled based on the age of the user.

The controller 613 may track growth rates or weight loss and generate alerts or report to external device 30 or network device 14 based on the growth rates or weight loss. In one example, the network device 14 calculated a weight gain or weight loss based on the displacement volume in the bathtub 600. The network device 14 may relay weight data to file for private transmission to a physician or to coaching/fitness program.

The controller 613 may include a microphone configured to collect audio (e.g., voice commands) for settings data for the auxiliary device, configuration data for the user, or type data for the auxiliary device. The microphone may be movable. The controller 613 may engage a positioning mechanism (e.g., stepper motor or solenoid) to move the microphone according to embodiments herein. The volume of the microphone may be configurable.

The voice commands received at the controller 613 may include device identifiers that describe the auxiliary device and device functions to be performed by the auxiliary device, which are described herein with respect to various appliances. In addition, the voice commands may include a device identifier for the bathtub 600, or omitting the device identifier may default to the mirror assembly, and a device function for the bathtub 600. Example functions performed at the bathtub 600 may include water level settings, water temperature settings, bath duration, sensory pattern sequence, media playback, control of the lights, control of the light guide, or selection of the collected data and selection of the displayed data.

The controller 613 may implement a cleaning cycle based on data collected at the bathtub 600 or at auxiliary devices and received through the home hub communication device. The cleaning cycle may be implemented in response to the user being in another room (e.g., the user is detected by a kitchen appliance). The cleaning cycle may be implemented in response to the user being positioned near another bathroom device. The cleaning cycle may include pre-rinsing the bathtub 600 before filing to the water level and/or rising the bathtub 600 after draining.

The controller 613 may draw a bath or obtain a specific water level in response to a schedule of the user. The schedule may be determined based on historical data of when the user takes a bath or based on user configured preferences such as day and time or based on location such as geofencing. The auxiliary device may instruct the controller 613 that a bath is being requested. The auxiliary device may be an exercise machine or fitness device that communicates the end of a workout as an indicator that the user is requesting a bath. A voice command listing the bathtub 600 as the device identifier and the bath as the device function may be received at the auxiliary device. The controller 613 is configured to provide the bath without waiting to the user.

Bathroom Cleaning Cycle

A bathroom cleaning device may perform a cleaning cycle for the bathroom. The bathroom cleaning device may be incorporated into the home hub communication device. The bathroom cleaning device may coordinate cleaning cycles of multiple devices including the intelligent toilet 6, the bathtub 600, or other devices. The bathroom cleaning device may control an air filtering system configured to filter aspirated particulate (e.g., fecal, urine). The bathroom cleaning device may include a dispenser that propels cleaning solution, or cleaning gas, into the atmosphere of the bathroom. The dispenser may include a safety mechanism that requires a secure seal in the room before dispensing. The user may override the dispenser or the bathroom cleaning device from inside or outside of the bathroom. The bathroom cleaning device may initiate a cleaning cycle based on data collected by another device (e.g., the cleaning cycle may be initiated based the door to the bathroom being closed).

The bathroom cleaning device may be operated according to sensor data collected at auxiliary devices. For example, the cleaning cycle may be operated to agree with the user's typical schedule based on learned patterns of operation of one or more of the auxiliary devices (e.g., intelligent toilet 6, shower 2, bathtub 600, or sink 8). The bathroom cleaning device may create and foster a microbiome between the intelligent toilet 6 and the shower 2 to balance microbial life.

Clothing System

The home hub communication system may also communicate with or include a dressing room controller. The dressing room controller may track closet inventory (clean) and pre-laundry (dirty) volume using one or more sensors. For example, the dressing room controller may track laundry inventory using one or more sensors placed in the home (e.g., closet, bathroom, bedroom) that detect individual articles of clothing using an inductive transmitter (e.g., RFID).

The dressing room controller may determine location of specific articles of clothing, for example, indicate if a desired article is in the closet or in the laundry. The dressing room controller may determine when laundry should be done. When a full load, or volume, of a specific type of clothing (color, type, delicates, etc.) is reached, an alert will be made through home hub communication device.

The dressing room controller may provide a list of clean clothing to the user. The list of clean clothing may be available on an interface of one of the appliances (e.g., mirror assembly 101) for the user to select and/or visualize clothing to wear.

The dressing room controller may assist a user from shopping from home. One or more appliances may collect sensor data to measure the body of the user (e.g., image collection device at mirror assembly 1, displacement volume at bathtub 600, or proximity sensors at other appliances). The dressing room controller suggests articles of clothing that fit the user based on the measurements. The dressing room controller may suggest articles of clothing based on the current inventory of clothing. For example, when a disproportionate amount of green clothing is in the inventory, the dressing room controller suggests green clothing for purchase.

Replacement Part Generation

Another household appliance in communication with the home hub communication device may include a replacement part generator. The replacement part generator may include a rapid prototype generator or a 3D printer. The replacement part generator is configured to print components for one or more of the appliances. The replacement parts may be generated through communication directly with the appliance or with external device 30 to download dimensions and other specifications for producing the part.

The replacement part may be generated in response to a remote service diagnosis of the appliance. For example, a leak detected by a sensor at the sink may be analyzed by the external device 30 to determine that a seal is broken. The external device 30 instructs the replacement part generator to produce a replacement seal. A user interface or the mirror assembly 1 may display instructions for removing the broken seal and replacing the broken seal with the newly generated seal. Any part may be generated and replaced including but not limited to connectors, brackets, covers, caps, handles, knobs, and gaskets.

The replacement part may be generated in response to a request by the user. For example, the user may request a different style of handle or knob such as the lever on the intelligent toilet 6 or the knobs on the sinks or shower. A user interface or the mirror assembly 1 may display instructions for removing the old part and installing the new part.

Recovery Space System

The home hub communication device may also coordinate a recovery space system that helps the user recover from exercise. The sensor data may include images of the user from a camera or other imaging device. The user's physical state including muscle strains and usage (e.g., muscle map) are determined from an image analysis. One or more auxiliary devices are instructed based on the images to help the user recover from exercise.

The physical state may be communicated to the shower 2 to select a massage pattern or temperature based to encourage recovery. The physical state may be communicated to a fitness device to suggest complimentary workouts. The fitness device may be a personal fitness device (e.g., wrist bracelet that tracks movements) and suggests specific exercises or an exercise plan. The fitness devices may be an exercise machine (e.g., elliptical machine, treadmill, or weight machine). The fitness device may generate a targeted recovery experience based on a muscle map determined from analysis of the images.

Medicine Cabinet

The mirror assembly 1 may include a smart medicine cabinet controller in communication with the home hub communication device and/or the server 13 through the network device 14. The smart medicine cabinet controller may aggregate data collected at other devices such as the appearance of the user collected by the mirror assembly 1, the analysis of the water of the user collected at intelligent toilet 6, and other physical data collected by the shower 2.

The smart medicine cabinet controller may include a communication interface and to communicate with a medical professional system. The medical professional system may analyze the aggregated data and provide a diagnosis or other medical recommendations to the user.

The smart medicine cabinet controller may provide instructions to a medicine generator and/or dispenser. The medicine generator may print medication such as OTC analgesics, vaccines, antibiotics, daily scripts) via patch or liquid. The medication may be tailored to the particular user based on sensor data collected at the auxiliary appliance. The medication may be adjusted according to the age of the user, the weight of the user, or other physical attribute. The medication may be adjusted according to the user's profile including allergies or the user's DNA.

Versatile Tiles

A versatile tile may include lights, speakers, sensors, and/or heaters implemented as flooring. Each of the intelligent bathroom devices is configured to collect data indicative of a user, communicate the data indicative of the user to another intelligent bathroom device either directly or indirectly, and provide services to user based on data indicative of the user that is received from other intelligent bathroom devices.

A versatile tile may include multiple functions that are tied to one or more of the auxiliary devices. The tiles may be integrated with sensors (e.g., image collection device, proximity sensor, temperature sensor, humidity sensor, VOC sensor, or other sensors) and the sensor data is provided directly to the home hub communication device on the auxiliary device. The sensors may include a pressure sensor configured to detect the pressure of a user's foot on the tile. The pressure sensor may be actuated by the user to switch between the functions of the tile (e.g., to switch between light, speaker, etc.). The tiles may include lights (e.g., light guide 9a). The tiles may include speakers for relaying information to the user from one or more of the auxiliary devices. The tiles may include microphones for receiving voice commands for one or more of the auxiliary devices. The tiles may include heaters and/or coolers for adjusting the ambient temperature. The heaters and/or coolers may be operated in response to temperature data received at one or more auxiliary devices. The heaters and/or coolers may be operated in response to the temperature or other temporary state of the user.

Therapy System

The home hub communication device may also instruct a therapy system. The therapy system may provide therapy to the user in response to the sensor data detected at one or more auxiliary devices. The therapy may include a multi-sensory experience that combines physical relaxation with virtual reality, using images, aroma, water, and light. The therapy system may treat the user with light or with guided imagery and biofeedback techniques. The therapy system may detect brain health to treat concussion, depression, anxiety, bipolar disorders, addiction, pain management, memory care, or other conditions non-invasively.

Light Guide System

The light guides, including light source 9a, which may be a light source array including one or more directional light sources, may project light on one or more other devices to guide the user to the device or help illuminate the area near the device. In response to a function being selected at one of the devices, user selection data, or a location and/or direction associated with a user selection, is transmitted to the light source 9a to define a direction for projecting the projected light guides 9b. The light guides may be incorporated in one or more of the auxiliary devices.

The light guide may be integrated with a home hub communication device. In one example, a control system for the light guide may include the components illustrated by FIG. 9. As such, the light guide may include a communication interface configured to connect with the network device 14 and/or the server 13 for communication with the auxiliary appliances. The communication interface may receive user data from at least one appliance, and the user data is indicative of an identity of a user. The light guide may include a controller configured to analyze the identity of the user and activate one or more directional light sources in response to the identity of the user. The light guide may include a memory including a lookup table for a plurality of users and user sequences for appliances within a predetermined distance of at least one direction light source in the light source array. The controller is configured to access the memory according the identity of the user to select the one or more activated directional light sources.

The light guide may include one or more sensors in a sensor array. The sensors may include a proximity sensor configured to detect at least a portion of a use in proximity to the light guide. The sensor may be a relative distance collection device such as a laser scanner. The sensors may include any of the environment sensors, microphones, or other sensors described herein. The sensor may be an image collection device with a lens such as a camera or an image collection device with a CCD. The sensor may be an audio sensor such as a microphone. The sensor may detect odors or VOCs.

The light guide may receive user input through voice commands received at the microphone or through a user interface at the light guide. The instruction from the user may trigger an auxiliary command for the auxiliary device. The data displayed at the user interface includes status data for the auxiliary device, settings data for the auxiliary device, configuration data for the user, or type data for the auxiliary device.

The auxiliary device may be an adjacent device within the same room as the light guide or less than a predetermined distance to the light guide. The auxiliary device may be a remote device in a different room from the light guide or greater than a predetermined distance from the light guide. With respect to the light guide, the adjacent devices may include bathroom devices such as the intelligent mirror 1, the programmable shower 2, the bathtub sensory device 3, the bathtub level device, the intelligent toilet 6, the toilet seat 7, the sink faucet 8, light guides, or a fan. With respect to the light guide, the remote devices may include kitchen devices such as the kitchen faucet 21, the dishwasher 22, the garbage disposal 23, the refrigerator 24, the water heater 25, and the water filter 26.

The control system for the light guide may select, based on the analysis of the sensor data, an auxiliary command for an auxiliary device coordinated with the light guide. The auxiliary command may be selected for a particular user. The auxiliary command for the auxiliary device is based on the instruction from the user received at the light guide and the data displayed at the user interface includes status data for the auxiliary device, settings data for the auxiliary device, configuration data for the user, or type data for the auxiliary device.

The analysis of the sensor data may determine an instruction received at the light guide. For example, the user may enter a command for the programmable shower 2 (e.g., select shower sequence or turn on/off shower), a command for the bathtub sensory device 3 (e.g., select a bath experience), a command for the bathtub level device (e.g., select a bath level), a command for the intelligent toilet 6 (e.g., flush or close the lid), a command for the toilet seat 7 (e.g., raise or lower the toilet seat), a command for the sink faucet 8 (e.g., select a temperature or volume), a command for light guides (e.g., a position or angle for the light), a command for the fan (e.g., a fan speed or on/off), a command for kitchen faucet 21 (e.g., select a temperature or volume), a command for the dishwasher 22 (e.g., a cleaning mode or on/off), a command for the garbage disposal 23 (e.g., a speed or on/off), a command for the refrigerator 24 (e.g., select a temperature), a command for the water heater 25, (e.g., select a temperature), or a command for the water filter 26 (e.g., activate or deactivate).

Settings data for the auxiliary device may be based on information received at the light guide from another of the auxiliary devices. That is, the light guide may receive data from one appliance, analyze the data, and send an instruction to another appliance. For example, data collected regarding height from a shower setting may be applied to a toilet seat position, a position of the user interface on the mirror substrate or a position of a light guide. Configuration data for the user may be based on the identification of the user or detection of the user and preferences previously established for the user. Type data for the auxiliary device may be used to apply a setting across a class of devices. For example, the user preferences may specify a temperature that is applied to all auxiliary devices with a temperature setting.

The light guide may include a speaker configured to provide audio for status data for the auxiliary device, settings data for the auxiliary device, configuration data for the user, or type data for the auxiliary device, as described herein. The light guide may include a microphone configured to collect audio (e.g., voice commands) for settings data for the auxiliary device, configuration data for the user, or type data for the auxiliary device. The microphone may be movable. The control module may engage a positioning mechanism (e.g., stepper motor or solenoid) to move the microphone and/or the speaker toward a user.

The voice commands received at the light guide may include device identifiers that describe the auxiliary device and device functions to be performed by the auxiliary device, which are described herein with respect to various appliances. In addition, the voice commands may include a device identifier for the light guide, or omitting the device identifier may default to the light guide, and a device function for the light guide. Example functions performed at the light guide may include control of the lights, control of the light guide, selection of the collected data and selection of the displayed data.

The control of the lights may include the color of the lights, brightness of the lights, intensity of the lights, or schedule for the lights, direction for the lights, hue for the lights, size of the light beam or focus for the lights. The control of the light guide may include an angle or position for the light is determined based on the auxiliary command selected for the user. For example, the voice command may instruct the light guide to illuminate handwashing in response to the voice command. The selection of the collected data may enable or disable one or more sensors. The selection of the displayed data may enable or disable the display of external data (e.g., weather) or data received from auxiliary devices.

The light guide may implement a user sequence including a series of light positions, which may be defined by angle or direction, duration, intensity, color or other factors. The control system for the light guide may include a lookup table that associate users with the preferred lighting sequence. The user sequence referenced in the lookup table includes a first appliance and a first time and a second appliance and a second time. The control system may use different lights at different times. For example, the control system may activate a first directional light source during the first time to illuminate at least a portion of the first appliance and activate a second directional light source during the second time to illuminate at least a portion of the second appliance. For example, a user's sequence may request that after turning on the lights, the sink is illuminated for a set time, then the toilet is illuminated for a set time, then the shower is illuminated for a set time. The user sequence may include a list of appliances and increment from one appliance on the list to the next appliances on the list after a voice command or other input is received for that appliance. For example, the sink is illuminated until the water is turned off, the toilet is illuminated until the toilet is flushed, or other examples. The user sequence may move from one appliance to the next automatically.

The light guide may receive voice commands for other appliances and illuminate those appliances according to specific tasks. For example, the controller for the light guide may receive a voice command for another appliance and parse the voice command for at least the device identifier and the device function. The control system may select one or more lights and a direction for the one or more lights in response to the device identifier and/or device functions. Device identifiers may indicate a direction for a particular appliance and device functions may indicate a direction for a particular portion of the appliance. The communication interface receives task selection data from the at least one appliance, and the control system is configured to analyze the task selection data to activate one or more directional light sources associated with a task in response to the task selection data. Example tasks include any of the device functions described herein such as turning on a sink, showering, opening a storage space, using a mirror, using a toilet, or filling a bathtub.

The light guide may implement the direction, intensity, and duration of the light according to user identity. The user identity may be determined by sensor data collected at any of the appliances according to examples herein. The communication interface of the light guide may receive user data from at least one appliance that is indicative of an identity of a user. The user identity is checked in memory against user preferences or configurations for the lights. The position of the lights may be based on the size of the user, the height of the user, the handedness of the user, or any other demographic characteristic of the user. The control system for the light guide analyzes the user data to identify at least one appliance to be illuminated for the user. The control of the light guide may also be based on the position of the user and any voice commands or other inputs received by the user. The control system generates a light command for a light source array comprising one or more directional light sources to illuminate at least a portion of the at least one appliance. The direction of the light sources, in addition to the identity of the user may be based on task selection data for the identity of the user. The light command for the light source array directs one or more directional light sources to illuminate at least a portion of the at least one appliance associated with a task from the task selection data.

In addition or in the alternative to the appliance itself, the one or more direction light sources associated with the task illuminate a path to the task or to the at least one appliance. The illumination of the task may be based on the user sequence, which is set by the user or learned from the user's historical activity. In this way, the task selection data includes a reminder for the user to perform the task. For example, the user sequence may specify that after the toilet is flushed, the sink should be used to wash hands. The reminder may instruct the user to pick up objects (e.g., clothes from the floor) or to put away objects (e.g., return the toothpaste to the drawer. Thus, the illumination of the task may correspond to handwashing. Other examples may be a guide to return to bed in the middle of the night or reach for a towel after showering. The sequence of light guides may encourage habit-building routines for children and those who may have cognitive issues. The control system may include a clock configured to track time of day, and the activated one or more directional light sources are modified according to the time of day.

Water Analysis

Any of the home hub communication devices (e.g., an appliance with an integrated home hub communication device or a standalone home hub communication device), the network device 14, or the server 13 may include a water analysis apparatus. The water analysis apparatus may be integrated with a water consuming device such as the programmable shower 2, the bathtub sensory device 3, the bathtub level device including the drain 4 and faucet 5, the intelligent toilet 6, the automated sink 8, the kitchen appliance 11, and the water system 12. The water consuming device is connected to a water supply or plumbing system.

The water analysis apparatus may include the components illustrated by FIG. 9. As such, the water analysis apparatus may include a communication interface configured to connect with the network device 14 and/or the server 13 for communication with the auxiliary appliances. The communication interface is configured to send a reporting message indicative of data collected by at least one appliance to the server 13.

The reporting message may include sensor data indicative of the water quality at one or more of the appliances. The sensors measuring water quality may include a water quality sensor, a pH sensor, oxygen sensor, or a chemical sensor that detects a specific substance, chemical, or element, such as mercury, iron, lead, The sensor may be a biological sensor that detects a type of bacteria or virus. The biological sensor may detect specific organisms such as *salmonella, e. coli, cryptosporidium* or *listeria*.

The sensor may be an image collection device that collects images of the user for determining an indication of illness, malnutrition, dehydration, or another condition or appearance of the user. The images may be analyzed for a change in color, pigment, or water content. Alternatively, the weight of the user may be monitored to detect signs of dehydration or sickness. The appearance of the user may be monitored to detect signs of illness, malnutrition, dehydration, or other conditions.

The reporting message may include device identifiers and timestamps associated with the collection of the sensor data. The reporting message may include geographic locations, which may be collected by a satellite positioning system, inferred from the IP address of the appliance, or entered directly by the user. The reporting message may include one or more sensor identifiers for the type of sensor used to collect the sensor data.

The reporting message may be received at another device such as the external device 30, the network device 14, or server 13. The network device 14 may analyze the sensor data across multiple appliances in the household. The server 13 or the external device 30 may analyze the sensor data across multiple households or a geographic region. The reporting message may be analyzed to determine an indication of a condition of water based on the sensor data. The condition of water may indicate that a foreign substance is in the water.

The external device 30, the network device 14, or server 13 may access a database according to the location where the sensor data was collected or other identifier to identify additional users or appliances in the geographic area where the sensor data was collected. The neighboring users may be defined according to water system (i.e., users on the same water system are considered in the same geographic area for the purpose of distribution the analysis message). An analysis message including the indication of the condition of water is generated in response to analysis of the sensor data and sent to the users or appliances in the geographic area. The water analysis apparatus receives the analysis message from the external device 30, the network device 14, or server 13.

The water analysis apparatus may perform geographic analysis on the sensor data from multiple locations. For example, the sensor data is analyzed for multiple appliances across multiple households or locations that are defined according to geographic location. A water condition database may correlate geographic areas with data collected by home appliances.

The water analysis apparatus may provide an alert in response to the analysis message. The alert may warn that a water anomaly has been detected. The alert may list the foreign substance detected in the water. The alert may provide instructions (e.g., boil water before use). The alert may include a rating for the water.

The water supply apparatus may monitor the usage of various appliances to determine whether the alert should be issued. For example, the water analysis message may indicate that a foreign substance is present in the water supply but is only harmful in specific quantities. When the flow sensor, or the aggregate flow sensors in a household, indicative that the appliances have used the specific quantities in a predetermined time interval, the water supply apparatus presents the alert. The alert may be based on a water limiting threshold for the volume of water or the type of water. The water limiting threshold limits the amount of water provided by the at least one second appliance or limits a type of water provided by the at least one second appliance.

The water analysis apparatus may instruct a filter setting according to the water analysis message. The filter setting may include filtering modes that target particular contaminants. A lead filtering mode may target removing lead from the water. A bacteria filtering mode may target removing bacteria from the water. A specific particulate filtering mode may target removing a specific particulate from the water. The filter setting may define a size of filter such as a particle trap opening, a thickness, or a variable path selected in response to the analysis message.

The water filtering may also be implemented by any faucet, the refrigerator 24, or the water heater 25. In addition, a water additive system may be implemented by any faucet, the refrigerator 24, the water heater 25, the water filter 26, or another water consuming device. The water analysis apparatus may instruct a water dispenser configured to selectively insert an additive to the water in response to the analysis message. The additive comprises a nutritional supplement, a flavor, an antibacterial agent, vaccine, vitamin, mineral, or a medicine.

The water analysis apparatus may perform a water circulation algorithm. The water circulation algorithm may open and close valve in water connections between one or more water consuming appliances and the water supply. Different appliances or different device functions may be applied to different types of water. Example types of water include potable water, cleaning water, recycled water, distilled water, or reclaimed filtered water. A set of rules may be applied to the device functions and/or the appliances. In one example, distilled water is preferred but at least potable water must be used in the water dispensing of the sink faucets 8 and the refrigerator 24, potable water is preferred but at least cleaning water may be used in the shower 2, the bathtub 600, or the dishwasher 22, and any type of water including reclaimed filtered water or runoff recycled water may be used in the intelligent toilet 6.

The water circulation algorithm may be activated by the voice command to route the water to one or more appliances according to the requirements of the appliances or device functions performed at the appliance. For example, the voice command to flush toilet may instruct the water circulation algorithm to open a valve that releases water of a first type to refill the toilet, and the voice command to turn on the shower instructs the water circulation algorithm to open a valve that releases water of a second type to the shower. The water circulation algorithm may analyze the voice command to route the water draining from one or more appliances to a tank for a specific type of water.

The water circulation algorithm may analyze sensor data at one or more of the appliances (e.g., at the drains) in order to classify the type of water and route the water to a tank for storing the water in future uses. The sensor data may describe the turbidity of the water or particulates of the water. For example, water in a shower may be recirculated until the water reaches a threshold level. When the threshold is reached the water circulation algorithm opens a valve to release the water to drain away from the household.

In one embodiment, the water analysis apparatus may be incorporated in any of the water consuming appliances. The appliances may include at least one sensor configured to collect data for a water condition associated with at least one first appliance and a controller configured to analyze the data for the water condition and identify or generate a resultant instruction in response to the analysis. The resultant instruction is sent to at least one second appliance.

Data Logging System

A data logging apparatus may be implemented by the home hub communication device, the network device 14, the server 13, or the external device 30. The data logging may be integrated with one of the appliances. The data logging apparatus may include the components illustrated by FIG. 9. As such, the water analysis apparatus may include a communication interface configured to connect with the network device 14 and/or the server 13 for communication with the auxiliary appliances.

The data logging apparatus receives sensor data from multiple appliances. The data logging apparatus may store the sensor data along with a sensor identification value, a device identification value, and/or a device function identifier. The data logging apparatus may store the sensor data with a time stamp. The data logging apparatus may provide the logged data from multiple appliances to a requesting appliance. For example, one appliance may request sensor data from multiple device to identify the user.

The data logging apparatus may analyze the sensor data to identify when one or more appliances should be serviced, upgraded, or replaced. For example, when a water heater temperature drops too quickly, the data logging apparatus may identify that an element should be replaced. When the water level of a bathtub drops to quickly, the data logging apparatus may detect a leak or an error with the leveling device, and inform the manufacturer, a service provider, or instruct the user to repair. The data logging apparatus may identify user patterns and recommend enhancements and recommend hardware upgrades to improve efficiencies in response to the user patterns. For example, the recommended hardware upgrades may include low flow toilets for a high traffic bathroom or a low flow shower head for heavily used showers. The data logging apparatus may recommend the user adjust behaviors such as bathing at certain times, taking shorter showers, or turn off the water when not in use.

The data logging apparatus may provide the logged data to a manufacturer to for monitoring design changes and marketing efforts. In some instances, the manufacturer may price product under cost or under market price to encourage data collection. The data logging apparatus may provide the logged data to a third party entity such as a municipal water company, an insurance provider, a city planner, or another entity according to any of the examples described herein.

Interchangeable Speaker

Figure 25:
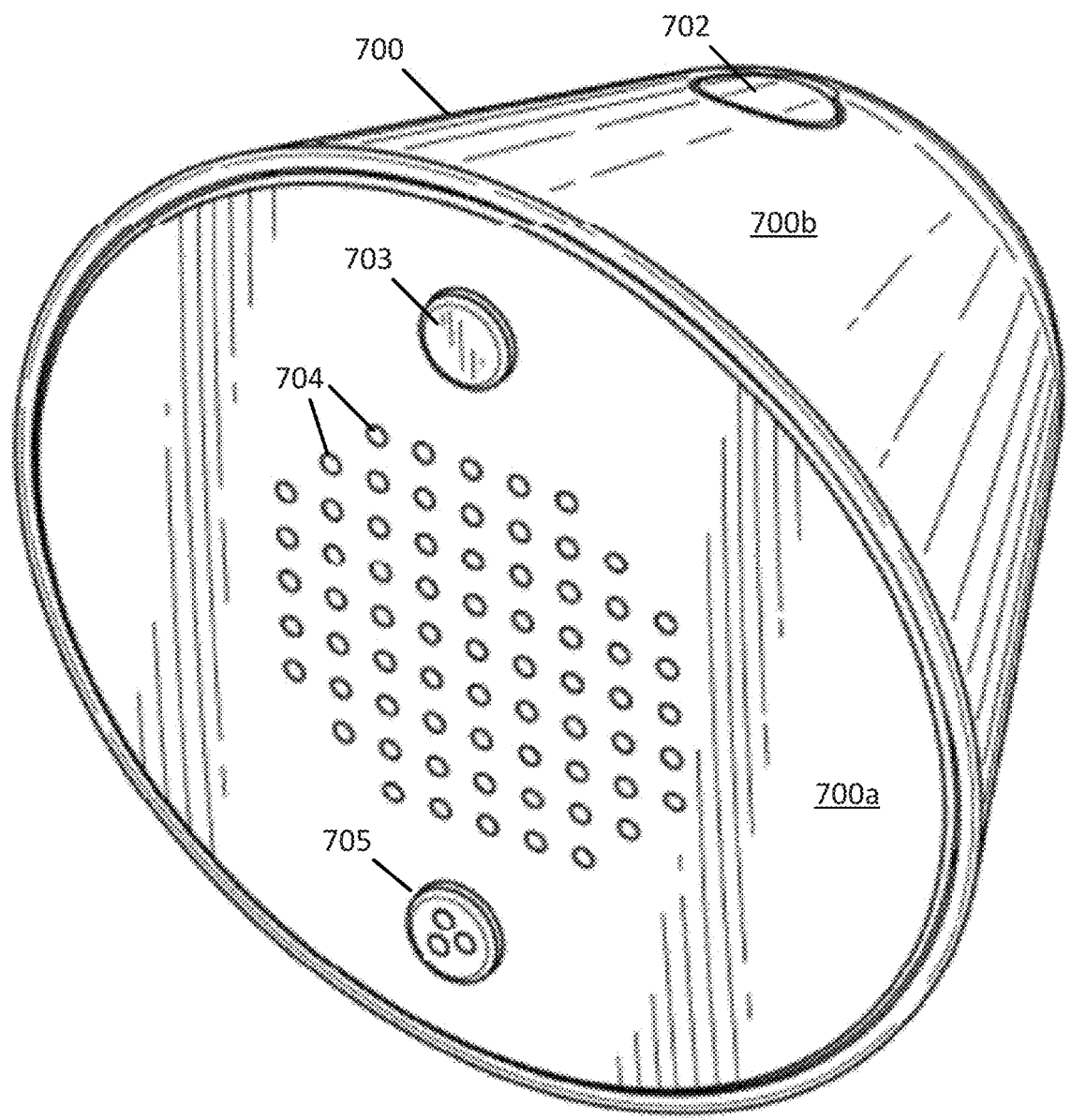
FIGS. 25 and 26 illustrate an interchangeable speaker.

FIG. 25 illustrates a front view of an interchangeable speaker 700, which may be a home hub communication device or an artificial intelligence device as described herein. The term voice controlled device encompasses these devices. The interchangeable speaker 700 may be incorporated into the network device 14 in any of the embodiments described herein. The interchangeable speaker 700 includes a switch 703, which may be a button for turning the speaker 700 on and off, and a microphone 705 configured to convert sounds to electrical signals. The microphone 705 may be omitted in some situations and may be disabled in some scenarios. As illustrated, the switch 703 may include a light indicator. For example, a light emitting diode behind a transparent shield that indicates whether the speaker is on (light indicator is on) or off (light indicator is off). Alternatively, the light indicator may indicate a mode, such as a low power mode (light indicator is on) or a normal mode (light indicator is off).

The interchangeable speaker 700 may internally include a controller configured to operate the audio function of the host appliance (e.g., receive verbal inputs and output sound) and also one or more primary functions of a host appliance (e.g., functions outlines herein with respect to the intelligent mirror 1, the programmable shower 2, the bathtub sensory device 3, the bathtub level device, the intelligent toilet 6, the toilet seat 7, the sink faucet 8, light source 9a and light guides 9b, the kitchen appliance 11, and the water system 12. The microphone 705 is configured to receive one or more voice inputs for the currently connected host appliance. For a controller that operates the audio function of the device, the controller may activate or deactivate one or more microphones 705, provide audio output through the speaker, and connect to the wireless network to receive data that is converted to the audio output provided through the speaker.

The controller may control additional functions of the host appliance and described in various embodiments herein. The interchangeable speaker 700 may be docked to the first appliance 31 and/or the second appliance 32, as illustrated in FIG. 4. The interchangeable speaker 700 may receive user data from one of the appliances (e.g., at least one water consuming device). The user data may describe sensor data collected at the first appliance 31 and/or the second appliance 32, entry data entered by the user at the first appliance 31 and/or the second appliance 32, logged data recorded at the first appliance 31 and/or the second appliance 32, or configuration data accessed the first appliance 31 and/or the second appliance 32.

The sensor data, or user data, is collected at the first appliance 31 and/or the second appliance 32 and describes the spatial position of the user or gestures of the user. The sensor data may be collected by a camera or image collection device. The entry data can be entered by the user at the first appliance 31 and/or the second appliance 32. The entry data may include login data or login credentials (e.g., a username and certifying information). The entry data may include a selection for operating the first appliance 31, which may be used to operate the second appliance 32. The logged data can be recorded at the first appliance 31 and/or the second appliance 32 to describe the habits or preferences of the users over time. The configuration data accessed the first appliance 31 and/or the second appliance 32 may relate to particular features or settings of the appliance.

The switch 703 may control additional systems associated with the interchangeable speaker 700, and the light indicator may indicate the selection of these additional systems. The switch 703 may switch the controller from one or more of a smart speaker mode, a room collaboration mode, and a host appliance control mode. Pressing the switch 703 may select the next of these modes, and the light indicator may illuminate a first color for the smart speaker mode, a second color for the room collaboration mode, and a third color for the host appliance control mode.

In the smart speaker mode, the interchangeable speaker 700 is configured to control the audio related functions of the interchangeable speaker 700. The audio related functions may include the volume level of the speaker. The audio related functions may include which microphones are activated (e.g., the number of microphones, the hardware address of the microphones, or the pattern of the microphones). The audio related functions may include receiving data from the wireless network or from the host appliance and providing audio in response to the received data.

In the room collaboration mode, the interchangeable speaker 700 is configured to receive and provide commands to other appliances other than the host appliances. In one example, the commands are received and sent through the wireless network. In another example, the commands are exchanged directly between the interchangeable speaker 700 and the other appliances (e.g., through Bluetooth, infrared, or other communication protocols).

In the host appliance control mode, the interchangeable speaker 700 is configured to control other functions of the host appliance. As described in other examples herein, the interchangeable speaker 700 receives data collected by the host appliances and analyzes the data according to user settings or preferences. The interchangeable speaker 700 generates user messages in response to the received data and/or generates commands for the host appliance in response to the received data.

The interchangeable speaker 700 may include a housing formed by coupling face 700a to cone 700b. The face 700a and the docking portion 700b may be welded together, attached by adhesive, or another technique to seal a speaker cone and a printed circuit board (PCB) from external elements such as water. The interchangeable speaker 700 includes a series of openings 704 that form a screen in the housing. Behind the screen, a seal may provide a water tight cavity that allows sound to transfer from the speaker and out of the interchangeable speaker 700. The microphone 705 may be flush with the face 700a or behind the face 700a.

Figure 26:
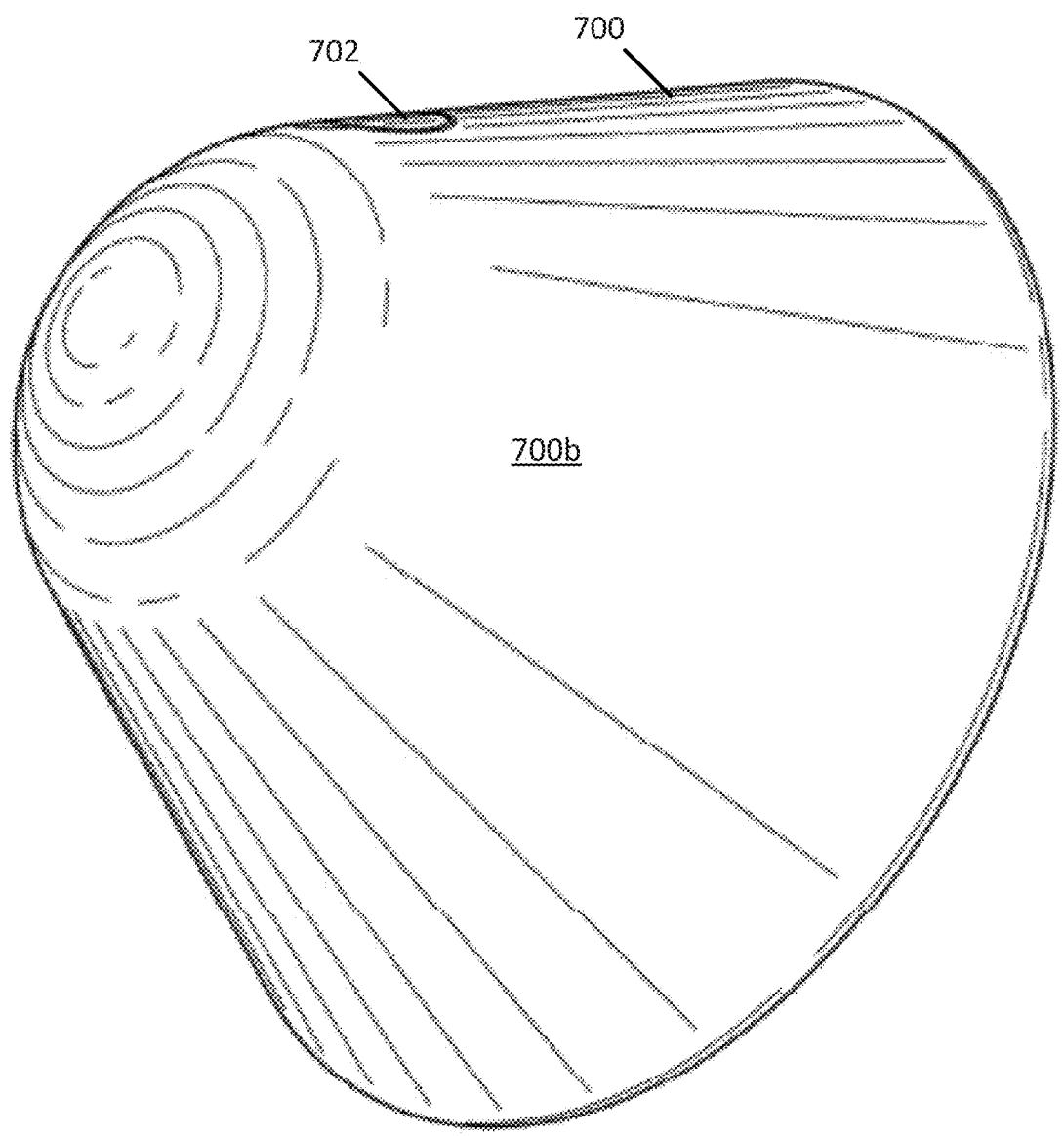

FIG. 26 illustrates a rear view of an interchangeable speaker 700. The interchangeable speaker 700 may have a variety of shapes including cone shaped, a cut-off cone shape, or a rounded cut-off cone shape as shown in FIG. 26.

The docking portion 700b may include securing mechanism that attached the housing to the host appliance. The securing mechanism may include a snap fit connection, a raised track for screwing the interchangeable speaker 700 into the host device, or a spring biased raised bearing for attaching the interchangeable speaker 700 to the host device.

Figure 27:
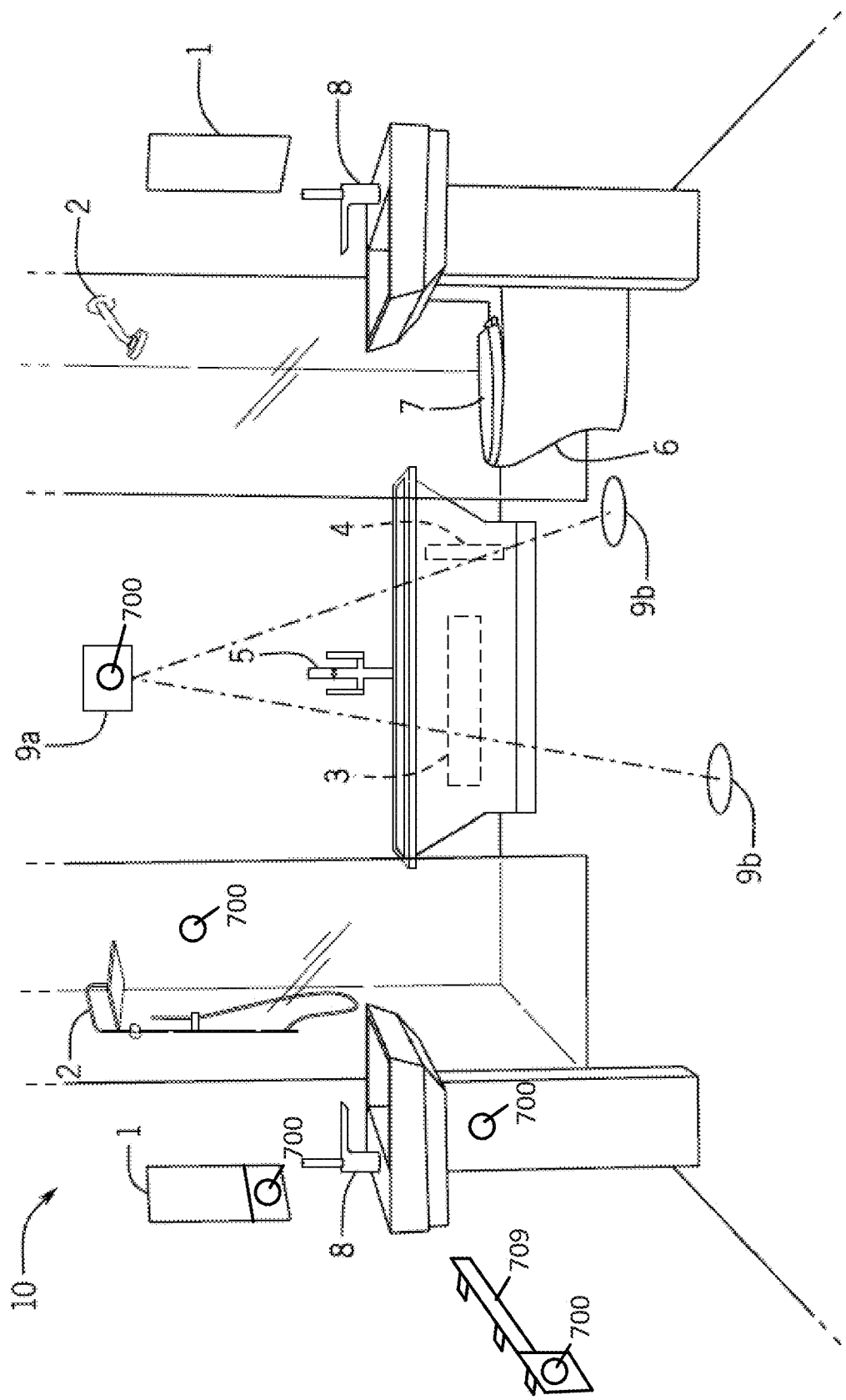
FIG. 27 illustrates a bathroom setting that includes multiple appliances or intelligent bathroom devices compatible with the interchangeable speaker.

FIG. 27 illustrates a bathroom setting that includes multiple appliances or intelligent bathroom devices compatible with the interchangeable speaker 700. The descriptions provided herein with respect to FIG. 1 may be applied to similar devices and components in FIG. 27. FIG. 27 also illustrates a towel bar 709 mounted to the wall and configured to hold garments or towels.

The docking portion 700b may be shaped to fit and interact with a variety of host devices or appliances, such as any of the intelligent bathroom devices described herein. Each of the intelligent bathroom devices is configured to receive the docking portion 700b of the interchangeable speaker 700. While any of the intelligent bathroom devices may also be configured to receive the interchangeable speaker 700, FIG. 27 illustrates that the towel bar 709 is configured to receive the interchangeable speaker 700, the intelligent mirror 1 is configured to receive the interchangeable speaker 700, the sink faucet 8 is configured to receive the interchangeable speaker 700, the shower walls or another shower structure is configured to receive the interchangeable speaker 700, the light guides (e.g., light source 9a and projected guides 9b) are configured to receive the interchangeable speaker 700. In addition, the programmable shower 2, the bathtub sensory device 3, the bathtub level device (e.g., including the drain 4 and faucet 5), and the intelligent toilet 6. In addition, or in the alternative, the docking portion 700b may be shaped to fit and interact with any of the intelligent kitchen devices, as shown in FIG. 2.

The docking portion 700b may be configured to mate with the intelligent mirror 1 through, for example, the control module housing 122 as illustrated in FIGS. 14A and 14B. The docking portion 700b may be configured to mate with the programmable shower 2, for example, at control module 195, as illustrated in FIG. 22. The docking portion 700b may be configured to mate with the bathtub sensory device 3 or the bathtub level device through a housing connected to bathtub 600, as illustrated by FIG. 24. The docking portion 700b may be configured to mate with the intelligent toilet 6 through control module 157, as illustrated in FIG. 17, or through control module 183, as illustrated in FIG. 18. The docking portion 700b may be configured to mate with the sink faucet 8, through control module 213, as shown by FIG. 21. The docking portion 700b may be configured to mate with the housing of the light guides 9a. The microphone 705 may be disabled when the interchangeable speaker 700 is docked with certain intelligent bathroom devices, such as the shower 2 or the intelligent toilet 6.

The interchangeable speaker 700 may be moved by the user from appliance to appliance. The transferability and interchangeability of the interchangeable speaker 700 provides multiple advantages.

First, in many examples the intelligent bathroom devices and/or intelligent kitchen devices have many redundant parts. For example, consider a bathroom with a separate speaker, microphones, and controller for each of a combination of the intelligent mirror 1, the programmable shower 2, the bathtub sensory device 3, the bathtub level device (e.g., including the drain 4 and faucet 5), the intelligent toilet 6, the sink faucet 8, and the light guides (e.g., light source 9a and projected guides 9b). The interchangeable speaker 700 reduces these redundant parts as multiple devices may use the same speaker, microphone, and controller as it is moved from host device to host device.

In some examples, the host devices may have permanent controllers and some of the functionality of the host devices is handled by the interchangeable speaker 700. The interchangeable speaker 700 may collect data at one appliance and apply that data at another appliance.

Second, the operation of multiple coordinating artificial intelligence devices may be coordinated and made more efficient by the interchangeable speaker 700. With a device (e.g., the device that is currently docked with the interchangeable speaker 700) designated as listener, the process of associating voice commands with their intended recipient is simplified. In other words, in a room with multiple devices with microphones listening for commands, the commands may be difficult to interpret.

The interchangeable speaker 700 may receive sensor data from one or more of the intelligent bathroom devices. In some examples, the sensor data may be indicative of the user identify or movement of the user. The sensor data may describe the spatial position of the user. For example, the sensor data may be collected by a motion sensor or a proximity sensor. The sensor data may include three-dimensional coordinates of the spatial position of the user of a portion of the user (e.g., feet, hands, or body). The sensor data may be collected by an eye gaze sensor that determines a line of sight or angular orientation of the face of the user. The sensor data may describe a gesture or movement made by the user. The sensor data may be collected by a camera or image collection device. The sensor data may describe the state of the body of the user using another characteristic such as heart rate, temperature, the presence of sweat, or odor. The user data may describe a condition of the user. Example conditions of the user includes a temperature, a heart rate, a height, a weight, a drowsiness, a complexion, a malnutrition, a hydration, or other conditions.

The interchangeable speaker 700 may collect any of these types of data types. The interchangeable speaker 700 may include at least one sensor configured to detect an ambient environment for the currently connected host appliance or user activity associated with the for the currently connected host appliance. The interchangeable speaker 700 may also receive entry data from a user such as login data or login credentials. The entry data may include a selection for operating any of the host appliances, or other appliances.

The interchangeable speaker 700 may access configuration data based on the sensor data. The selection of the configuration data may depend on where or what type of host appliance the interchangeable speaker 700 is docked to. For example, a particular user may have a preferred volume setting or use a mute setting to disable the speaker is certain situations.

Through first docking with one of the intelligent bathroom devices and subsequently docking with another one of the intelligent bathroom devices, the interchangeable speaker 700 may transfer data (e.g., sensor data) between the intelligent bathroom devices. The interchangeable speaker 700 may collect data from multiple intelligent bathroom devices and different times and log the data. The data from multiple intelligent bathroom devices may then be analyzed at the interchangeable speaker 700 or sent to the server 13 for analysis.

Figure 28A:
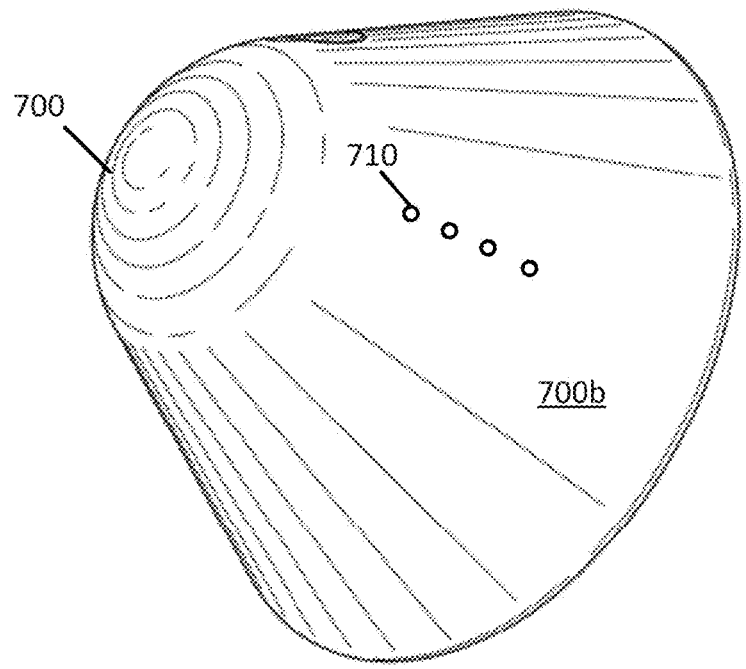
FIGS. 28A, 28B and 28C illustrate a docking detection system for the interchangeable speaker.
Figure 28B:
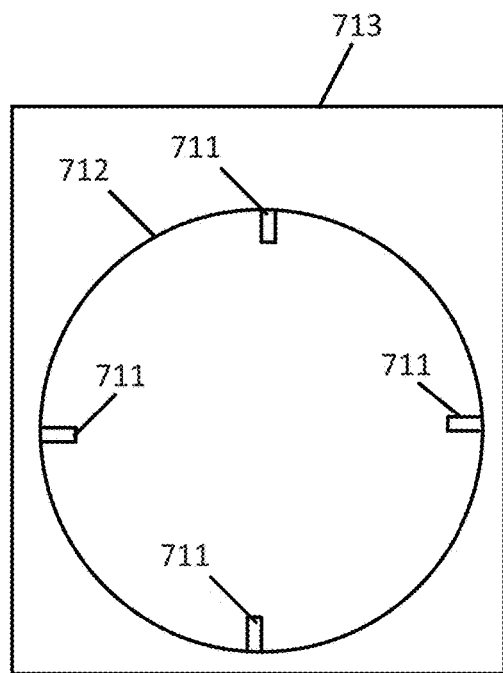
Figure 28C:
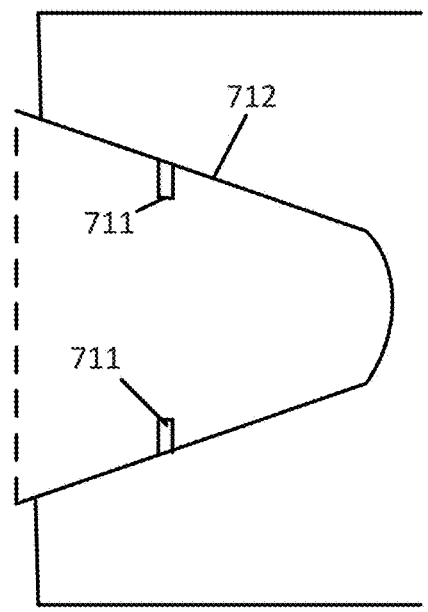

FIGS. 28A, 28B and 28C illustrate a docking detection system for the interchangeable speaker. The cone portion 700b of the housing of the interchangeable speaker 700 is an example a dock configured to connect the housing to any of the host appliances.

FIG. 28A illustrates the interchangeable speaker 700 including multiple openings 710, which are contact points. FIG. 28B illustrates a host appliance 713 including a docking receptacle 712 shaped to fit the interchangeable speaker 700. The docking receptacle 712 includes one or more protrusions 711, which are contact points. The multiple openings 710 of the interchangeable speaker 700 may be associated with different appliances for mounting the interchangeable speaker 700.

The contact points for openings 710 and the contacts points for protrusions 711 provide an electrical connection circuit that connects the interchangeable speaker 700 to the host appliance 713. The electrical connection circuit allows the interchangeable speaker 700 to detect the host appliance 713, or allows the host appliance 713 to detect the interchangeable speaker 700, or both. The detecting device (either the host appliance 713 or the interchangeable speaker 700) detects the detected device (the other of the host appliance 713 or the interchangeable speaker 700) and generates data or a signal that indicates that docking has occurred.

The different openings 710 may correspond to different host appliances 713 or types of host appliances. For example, one opening 710 may be aligned with protrusion 711 for the mirror 1, another opening 710 may be aligned with protrusion 711 for the shower 2, and another opening 710 may be aligned with protrusion 711 for the sink. A circuit internal to the interchangeable speaker 700 may include resistors, other circuit elements, or circuit paths that are energized differently depending on where the protrusion 711 makes contact with openings 710.

Alternatively, only one opening 710 may be used, and the protrusions 711 are located in similar positions for the host appliances 713, but another technique is used to identify the host appliance 713. In one example, the signal may have different voltage levels that corresponds to different host appliances. In another example, the signal may vary according to a resistance in the detected device. The controller of the interchangeable speaker 700 may detect the voltage level or resistance value to identify which host appliance is docked with the interchangeable speaker 700. The controller may access a set of commands or a mode of operation associated with the detect host appliance.

In another example, the communication in the electrical path between the opening 710 and the protrusion 711 may include data that identifies the docking between the devices or the identity of one of the devices (e.g., identity of the host appliance). The contact points for openings 710 and the contacts points for protrusions 711 provide coupling mechanism configured to receive an identification value indicative of docking between the voice controlled device and a currently connected host appliance. The coupling mechanism may include a first electrical contact through the opening 710 at a surface of the housing. The first electrical contact is operable to transfer the identification value through a second electrical contact at the protrusions 711 of the currently connected host appliance.

The identification value for the docking of the interchangeable speaker 700 to the host appliance may also be determined based on a user input. For example, the user may press button 703 (e.g., press and hold) to indicate that the interchangeable speaker 700 has been docked. In response any of the coupling mechanisms may be used to determine the identity of the host appliance. In addition, the user input may include the identification value (e.g., through a menu selection). A voice command may also indicate the identity of the host appliance (e.g., dock speaker to mirror).

The identification value for the docking of the interchangeable speaker 700 to the host appliance may also be determined based on communication between the interchangeable speaker 700 and the host appliance through the wireless network and/or server 13. The controller 804 may identify that the interchangeable speaker 700 is docked based on a connection to the wireless network (i.e., when the interchangeable speaker 700 is connected to the same network as the host appliance). The identification value for the docking of the interchangeable speaker 700 to the host appliance may also be determined based on GPS sensors. The identification value for the docking of the interchangeable speaker 700 to the host appliance may also be determined based on machine learning analysis of other habits of the user.

Commands may be provided to the host appliances based on the identification value that is indicative of the host appliance and/or based on one or more voice inputs received at the microphone 705. A command is provided based on the one or more voice inputs and the identification value. In some examples, the command is generated at the interchangeable speaker 700 to instruct the speaker to produce sounds in response to the one or more voice inputs and the identification value. In some examples, the command is generated at the interchangeable speaker 700 to instruct a display to provide information regarding the command or operation of the host appliance. In some examples, the command is generated at the interchangeable speaker 700 to instruct the host appliance to control a host appliance such as turn on a function of the host appliance (e.g., turn on water, turn on light), change a setting (e.g., water temperature, water flow rate or volume, or a light intensity), or provide information regarding the operation of the host appliance. The interchangeable speaker 700 may provide the information through the display or speaker. Thus, the operation of the speaker including the sounds produced by the speaker are adjusted based on the identification value.

The interchangeable speaker 700 or the host appliance may also include one or more light guides or illumination devices configured to produce light in response to the one or more voice inputs and the identification value. The light guides may include light source 9a and projected guides 9b but may also be included as light sources on any of the host appliances. The light guides may project light on one or more other devices to guide the user to the device or help illuminate the area near the device. The light guide from one of the host appliances may illuminate another host appliance to guide the use between appliances. In response to a function being selected at one of the devices, user selection data, or a location and/or direction associated with a user selection, is transmitted to the light guide to define a direction for projecting the projected light guides. The status of the light guides may be transmitted to and displayed by the display of the interchangeable speaker 700. In one alternative, the light guides are implemented as versatile tiles or tech tiles. The versatile tiles may include lights, speakers, sensors, and/or heaters implemented as flooring.

Figure 29A:
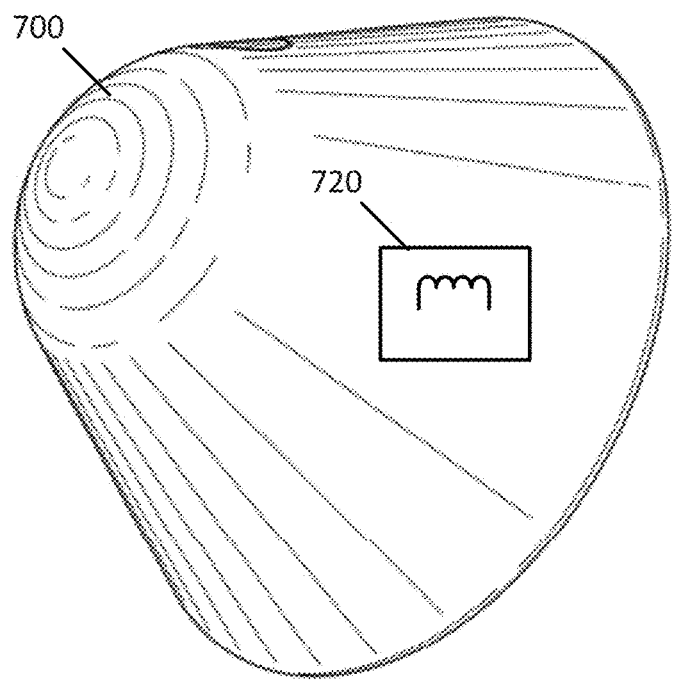
FIGS. 29A and 29B illustrate an inductive coupling system for the interchangeable speaker.
Figure 29B:
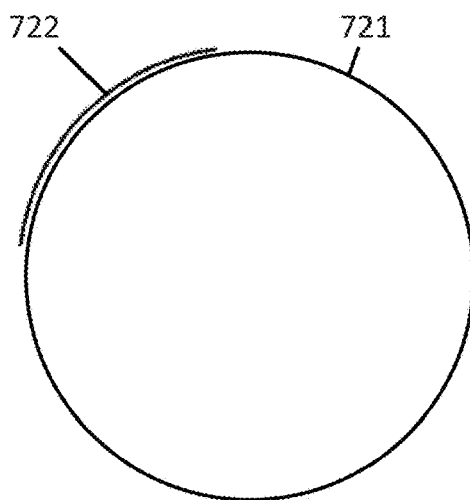

FIGS. 29A and 29B illustrate an inductive coupling system for the interchangeable speaker 700. The interchangeable speaker 700 may include an induction circuit 720 including an inductive coil that generates a magnetic field including the identification value or receives a magnetic field including the identification value. The host appliance may include an induction circuit 722 arranged inside the docking receptacle 712 or near the docking receptacle. The induction circuit 722 may include an inductive coil that generates a magnetic field including the identification value or receives a magnetic field including the identification value. The identification value may be modulated on the magnetic field. In other words, the inductive coil has a carrier frequency or amplitude that is modified according to an identification value from the induction circuit. The identification value corresponds to the type of host appliance, the specific identity of the host appliance, the type of interchangeable speaker 700, or the specific identity of the interchangeable speaker 700.

The inductive coupling system may include a coupling mechanism based on the cooperative relationship of the induction circuit 722 including a first induction coil attached to the voice controlled device. The first induction coil is operable to transfer the identification value through the magnetic wave to a to the induction circuit 720 including the induction coil attached to the currently connected host appliance. The inductive coupling system may include a coupling mechanism based on the cooperative relationship of the induction circuit 720 including a first induction coil attached to the voice controlled device. The first induction coil is operable to transfer the identification value through the magnetic wave to a to the induction circuit 722 including the induction coil attached to the currently connected host appliance.

FIGS. 30A, 30B and 30C illustrate a magnetic coupling system for the interchangeable speaker. The interchangeable speaker 700 may include one or more magnets 730 arranged at the surface of the housing or under the housing. The host appliance may include one or more magnets 734 at a surface of docking receptacle 721 or behind the surface of the docking receptacle 721. The magnets 730 of the interchangeable speaker 700 interact with the magnets 734 of the host appliance.

The magnets may provide a physical coupling or support for the interchangeable speaker 700 that is docked in the host appliance. Either or both of the magnets 730 of and the magnets 734 may supply a magnetic force to the other of the magnets 730 of and the magnets 734, which tends to provide a docking force between the interchangeable speaker 700 and the host appliance. In other words, the magnets 730 of and the magnets 734 may hold the interchangeable speaker 700 to the host appliance through magnetic force.

The magnets 730 of and the magnets 734 may be arranged in various patterns around the interchangeable speaker 700 and the docking receptacle 721, respectively. The arrangement of the magnets may ensure that the interchangeable speaker 700 is docked in the correct, upright position. For example, their may be only one way for the magnets 730 of and the magnets 734 to align to provide the docking force. Alternatively, a physical guide may provide the alignment between the interchangeable speaker 700 and the docking receptacle 721. For example, a guide rail 732 of the interchangeable speaker 700 may fit in a guide groove 735 of the docking receptacle to ensure that the interchangeable speaker 700 is docked in the correct, upright position. In other examples, the interchangeable speaker 700 may be docked in a variety of angles, with the magnets 730 of and the magnets 734 have multiple radial alignments possible.

The magnets 730 of and the magnets 734 may provide identification of the host appliance to the interchangeable speaker 700 or identification of the interchangeable speaker 700 to the host appliance. The magnets 730 of and the magnets 734 may be a coupling mechanism that physically couples and/or magnetically couples the at least a first magnet of magnets 730 of the voice controlled device to at least a second magnet of the magnets 734 attached to the host appliance. The identification may be provided through different arrangement of magnets in different docking receptacles associated with different host appliances.

The controller or control circuit of the interchangeable speaker 700 may include one or more magnetic sensors or magnetically completed circuit paths that correspond to the magnets 730. When the magnets 730 are coupled with magnets 734, the magnetically completed circuit paths are completed or the magnetic sensors are triggered to detect the docking of the interchangeable speaker 700. The controller may determine the identification value provided through the magnetic coupling.

The magnetic coupling system may include a coupling mechanism based on the cooperative relationship of the magnet 730 and the magnet 734. The controller is operable to detect the identification value through the detect of the relationship between the magnet 730 and the magnet 734.

FIGS. 30B and 30C illustrate two example arrangement of magnets 734 in two different types of host appliances. In FIG. 30B, the magnet 734 is arranged approximately at angle $a_1$ (e.g., 60 degrees) counter-clockwise from the guide groove 735. In FIG. 30C, the magnet 734 is arranged approximately at angle $a_2$ (e.g., 45 degrees) counter-clockwise from the guide groove 735. Host appliances may include multiple magnets in predetermined patterns in different radial positions as well as different lengthwise positions along the housing of the interchangeable speaker 700.

When the interchangeable speaker 700 is docked with the host appliance, different magnets 730 of the interchangeable speaker 700 are coupled depending on whether the host appliance in FIG. 30B with one magnetic position is docked with the interchangeable speaker 700, or the host appliance in FIG. 30C with another magnetic position is docked with the interchangeable speaker 700. The controller is configured to determine the magnetic position based on the magnetically completed circuit paths that are completed or the magnetic sensors that are triggered. The controller may access a magnetic lookup table according to the magnetic position. The magnetic lookup table associated magnetic positions (e.g., 160 degrees, 45 degrees, 60 degrees in combination with 90 degrees) that correspond to identification values that for example, correspond to different types of host appliances as described herein.

The interchangeable speaker 700 may include a command lookup table or access such a command lookup table from the server 13 or the host appliance. The command lookup table may be queried with the type of host appliance based. The command lookup table may return a set of commands available for the host appliance, or values for default or preferred settings of the host appliance.

In other words, the controller of the interchangeable speaker 700 may query the command lookup table using the identification value for the host appliance. The command lookup table may return a set of commands for the host appliance, which may be the commands available for the type of host appliance or the commands available to the current user. Because less than all possible commands may be available, the result from the command lookup table may be a reduction of the possible commands. With fewer commands available, the voice commands from the user may be more easily interpreted.

The controller may adjust the output of the interchangeable speaker 700 based on the identification of the host appliance. Examples include adjustment of the sound volume and light intensity of the interchangeable speaker 700. Certain host appliances may produce noises that interfere with the sound output of the interchangeable speaker 700. In addition, host appliances may be in a location that is a farther distance from the user that impedes sound travel. The interchangeable speaker 700 may adjust the volume of the sound according to the identification value for the host appliance. Similarly, host appliances may be in darker environments or farther distances from the user that interferes with the light output of the interchangeable speaker 700. The interchangeable speaker 700 may adjust the light intensity of a display or a light guide according to the identification value for the host appliance. As described in more detail below, the microphones and analysis of the interchangeable speaker 700 may be adjusted according to the host appliances or appliances in the vicinity of the interchangeable speaker 700. The controller may adjust the voice inputs based on the identification of the host appliance.

Figure 31:
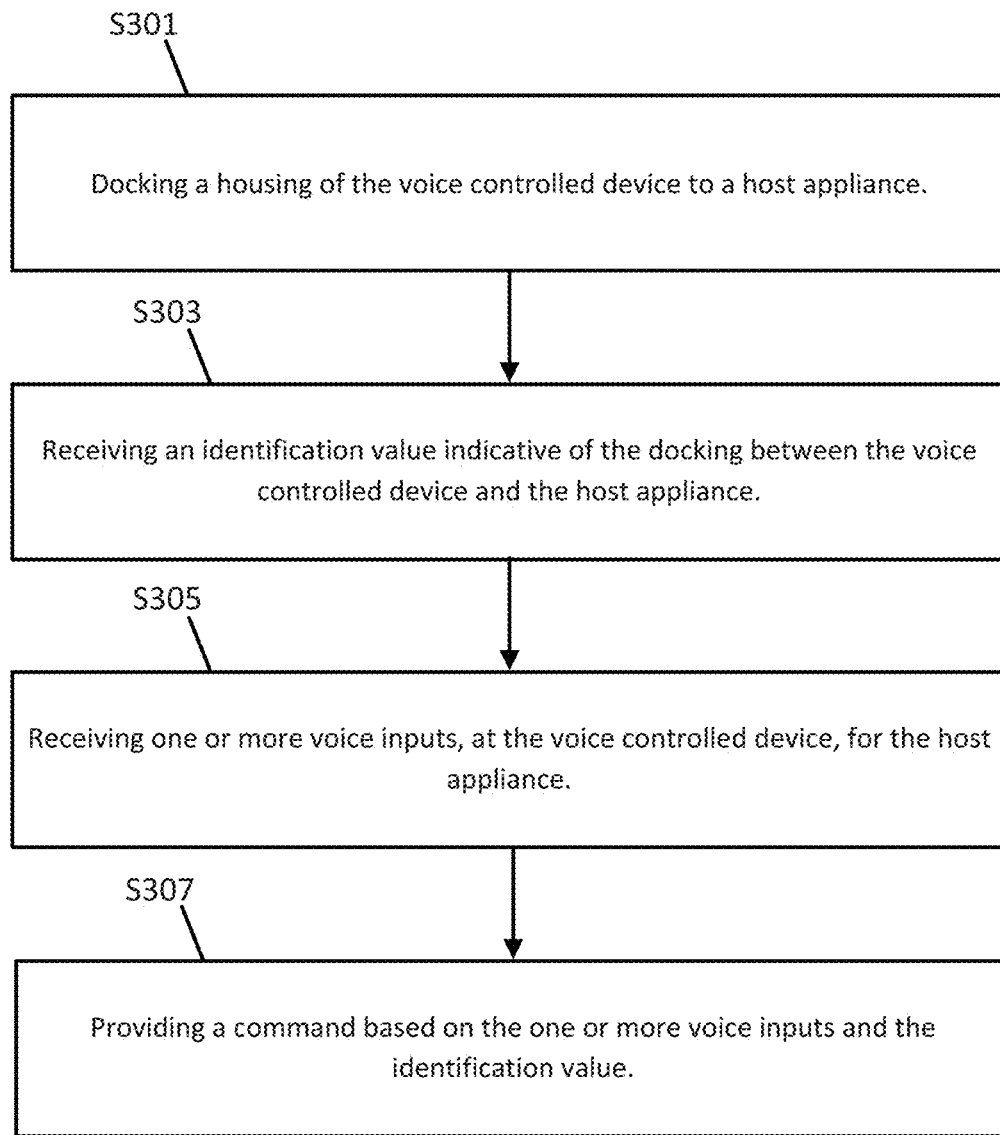
FIG. 31 illustrates a flow chart for the interchangeable speaker.

FIG. 31 illustrates a flow chart for the interchangeable speaker 700. The method may be performed by the interchangeable speaker 700 as a whole, or specific aspects of the method may be performed by the controller of the interchangeable speaker 700 or the coupling device or circuitry of the interchangeable speaker 700. Additional, different, or fewer acts may be included.

At act S301, the housing of the voice controlled device (e.g., interchangeable speaker 700) is docked to a host appliance. The docking may include one or more guiding mechanisms or locking mechanism that bring the voice controlled device in contact with and fixedly supported by the host appliance.

At act S303, the voice controlled device receives an identification value indicative of the docking between the voice controlled device and the host appliance. The identification value may be included in a data message that is transferred wirelessly. The identification value may be determined based on inductive coupling or magnetic coupling between the voice controlled device and the host appliance. Act S303 may also include magnetically coupling a first magnet attached to the voice controlled device to a second magnet attached to the host appliance, such that the identification value is provided through the magnetic coupling and a force for docking the voice controlled device to the host appliance is provided through the magnetic coupling. Act S303 may also include energizing a first induction coil attached to the voice controlled device to transfer the identification value through a magnetic wave to a second induction coil attached to the host appliance. Act S303 may also include electrically coupling a first electrical contact at a surface of the housing to transfer the identification value through a second electrical contact of the host appliance.

At act S305, the voice controlled device receives one or more voice inputs for the host appliance. The voice inputs may be sounds produced by a user providing instruction to the host appliance or the voice controlled device.

At act S307, the voice controlled device provides a command based on the one or more voice inputs and the identification value. In addition, the voice controlled device may provide audio output from a speaker of the voice controlled device in response to the one or more voice inputs and the identification value. The audio output content may depend on the identification value. That is, the voice controlled device provides different audio output when the host appliance is a mirror rather than a toilet. The voice controlled device may adjust the audio output produced by the speaker are adjusted in volume, pitch, or speed based on the identification value. Different host appliances may be associated with different volumes or other sounds characteristics so that the audio output is easier to hear or the host appliance as a signature sound (e.g., different style of voice for different host appliance). The style of voice may be gender or famous voices. A different famous voice may be applied to different host appliances. In addition, the style of voice may be language. The language may be adjusted according to the location (e.g., country) of the host appliance.

Filtering Sound for Intelligent Bathroom Devices

The home hub communication devices and well as the interchangeable speaker 700 in preceding sections may be configured to adjust the analysis of voice inputs as a function of the environment of the home hub communication device, the appliances in the vicinity of the home hub communication device, or the operation state of the appliances in the vicinity of the home hub communication device.

Figure 32:
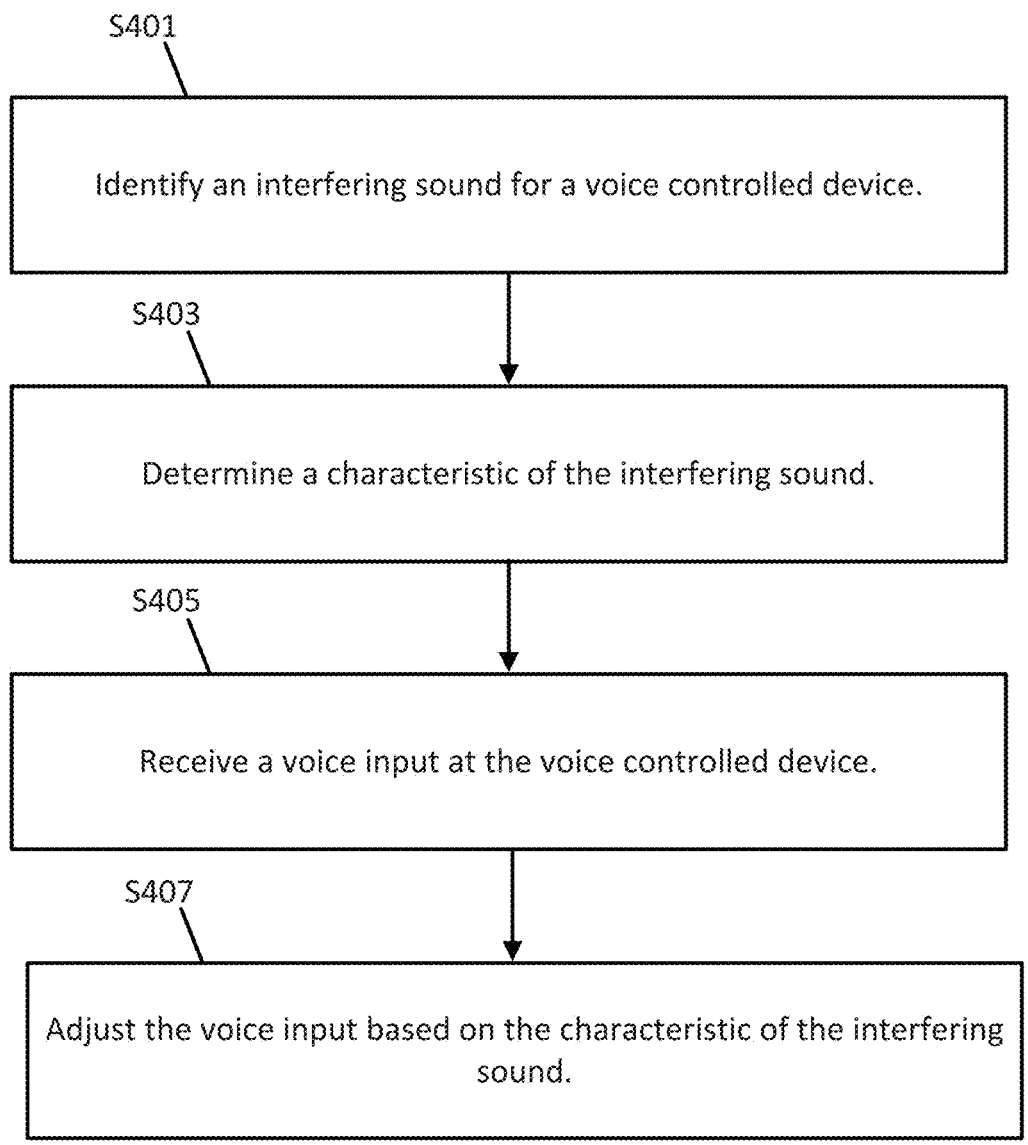
FIG. 32 illustrates a flow chart for sound filtering based on intelligent bathroom devices.

FIG. 32 is a flow chart for sound filtering for a voice controlled device, which may include any of the home hub communication systems or intelligent bathroom devices described herein. The method may be performed by the voice controlled device as a whole, or specific aspects of the method may be performed by the server 13. Additional, different, or fewer acts may be included.

At act S401, the voice controlled device identifies an interfering sound. The interfering sound may be a sound caused by water usage of the intelligent bathroom device. The interfering sound may be the sound of water spraying and hitting surfaces in the shower, the sound of a toilet flushing and/or filling the tank, or the sound of water flowing from a faucet or shower head. The interfering sound may be non-water based sounds such as operation of a fan or a heater. Many other sounds are possible.

The identification of the interfering sound may be made in a variety of techniques. The interfering sound may be detected directly through a microphone. The interfering sound may be determined based on the settings of the appliance producing the sound. That is, the voice controlled device may have instructed the shower to turn on or be aware (such as through communication with another interconnected device) that an instruction was sent to the shower to turn on, and determine that the shower is producing the interfering sound based on the instruction. The voice controlled device may determine the presence of the interfering sound based on another factor or combination of factors, such as time of day, humidity detected in the air, detection of a change in characteristic of a device (such as detection of water flowing through a system or detection of a circuit or relay changing states).

At act S403, the voice controlled device determines a characteristic of the interfering sound. The characteristic may be the volume or amplitude of the sound waves. The characteristic may include the frequency or spectrum of the sound waves. The voice controlled device, or another device in communication with the voice controlled device, may include sensors and supporting circuitry to detect the amplitude of the output of the interfering sound and/or the frequency spectrum of the interfering sound. The characteristic may be the types of sound (e.g., shower, toilet, or faucet). In addition, the voice controlled device may include a temporal characteristic that describes when the interfering noise is expected to start or end.

At act S405, the voice controlled device receives a voice input. The voice input may be words spoken by the user to the voice controlled device and in the vicinity of the appliance producing the interfering noise. In some examples, the user may be closer to the appliance producing the interfering noise than to the voice controlled device. For example, a user may be providing the voice input from inside the shower to the voice controlled device at the mirror across the bathroom. In other instances, the user may be near the voice controlled device, but the interfering sound may normally cause disruption in the ability of the voice controlled device to differentiate a voice from the noise.

At act S407, the voice controlled device adjusts the voice input based on the characteristic of the interfering sound. The voice controlled device may apply a software or hardware based filter based on the amplitude of the output of the interfering sound and/or the frequency spectrum of the interfering sound. The voice controlled device may apply equalizer settings based on the amplitude of the output of the interfering sound and/or the frequency spectrum of the interfering sound. For example, the voice controlled device may amplify or attenuate frequency bands of the voice input in response to the detected characteristics of the interfering sound. The adjustment of the voice input may vary in real time. The interfering sounds may change over time in intensity and/or frequency. The voice controlled device may detect these changes and adjust the voice inputs accordingly. The voice controlled device may perform a noise cancellation algorithm or logic to reduce or eliminate the interfering noise.

The voice controlled device may apply a filter according to the sound characteristic. The voice controlled device may store in memory multiple filters. Each of the appliances or intelligent bathroom devices may be assigned a filter according to the sound that the device makes. Each of the appliances or intelligent bathroom devices may be assigned a filter for a specific user according to the sounds that the user makes with the particular device.

Because the voice input has been adjusted to account for the interfering sound, the voice controlled device may perform voice recognition at a higher confidence level. That is, voice commands for the user may be more easily interpreted even in the presence of the interfering sound. Alternatively, the voice controlled device may record the voice inputs and forward sound files or messages to the server 13, and the server 13 can more easily interpret the voice commands even in the presence of the interfering sound.

The server 13 or the voice controlled device may also store filters or voice input modification data for different types of devices that are in different environments. When a voice input is received, the voice input modification data is accessed for a current environment of the voice controlled device. The current environment may depend on the usage of any of the appliances or a setting of any of the appliances.

For example, the server 13 or the voice controlled device may receive data that indicates that a particular appliance (e.g., a shower) is being used. The home hub communication devices, or the interchangeable speaker 700, that is in the vicinity or the same room as the particular appliance (even if it is not at the particular appliance) may modify subsequent voice inputs based on the usage of the particular appliance. For example, a sensor at the valve of the shower 2 or the lever of the toilet 6 may report that the appliance is being used, and accordingly there will be noise. The server 13 or the voice controlled device may access the filter for one of these scenarios, and subsequently (for a predetermined time) modify voice inputs that are received through the microphone of the voice controlled device.

In some alternative methods, the voice controlled device may, before, during or after determining an interfering sound, adjust listening behavior or requirements. For example, a voice controlled device may perform any of the filtering and/or cancellation techniques with all sounds received at the voice controlled device automatically and immediately upon starting at S401, thereby ultimately performing step S407 right after determining of potential interfering noise. Many other variations are possible.

In some systems, control and operation of an interchangeable speaker 700 may vary as a result of determination of an interfering noise (such as at S401). In some systems, output characteristics (such as amplitude and/or frequency) of sound waves emitted from the speaker 700 may be modified to accommodate different sound characteristics present in the setting. For example, when the system detects the operation of a fan, the speaker 700 output may be modified to increase the amplitude of sound within various frequency spectrums to cancel undesirable noise interference, or accentuate desirable frequencies of sound. Many other variations are possible.

Power Modes

Figure 33:
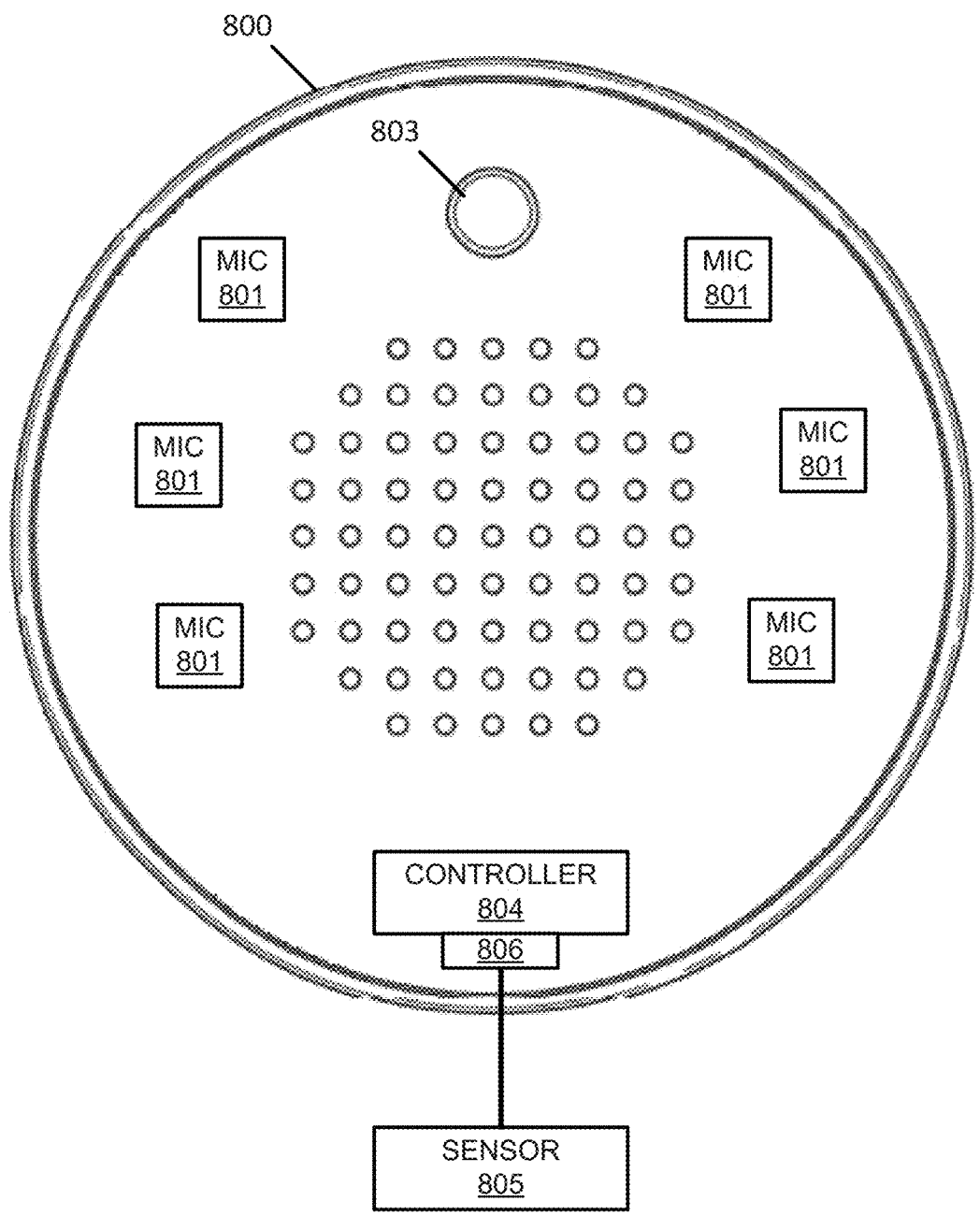
FIG. 33 illustrates a microphone array for a speaker.

FIG. 33 illustrates a microphone array for an artificial intelligence device 800. The artificial intelligence device 800 may be the interchangeable speaker 700, or included in any of the voice controlled devices or intelligent bathroom devices described herein, or network device 14. The artificial intelligence device 800 includes an array of microphones 801 and a controller. The artificial intelligence device 800 may optionally include a least one sensor 805 and may optionally include one or more user inputs (e.g., button 803). In some embodiments, at least one sensor 805 is external to the speaker or artificial intelligence device 800, for example located in any of the appliances or intelligent bathroom devices described herein. Additional, different, or fewer components may be included.

Figure 34:
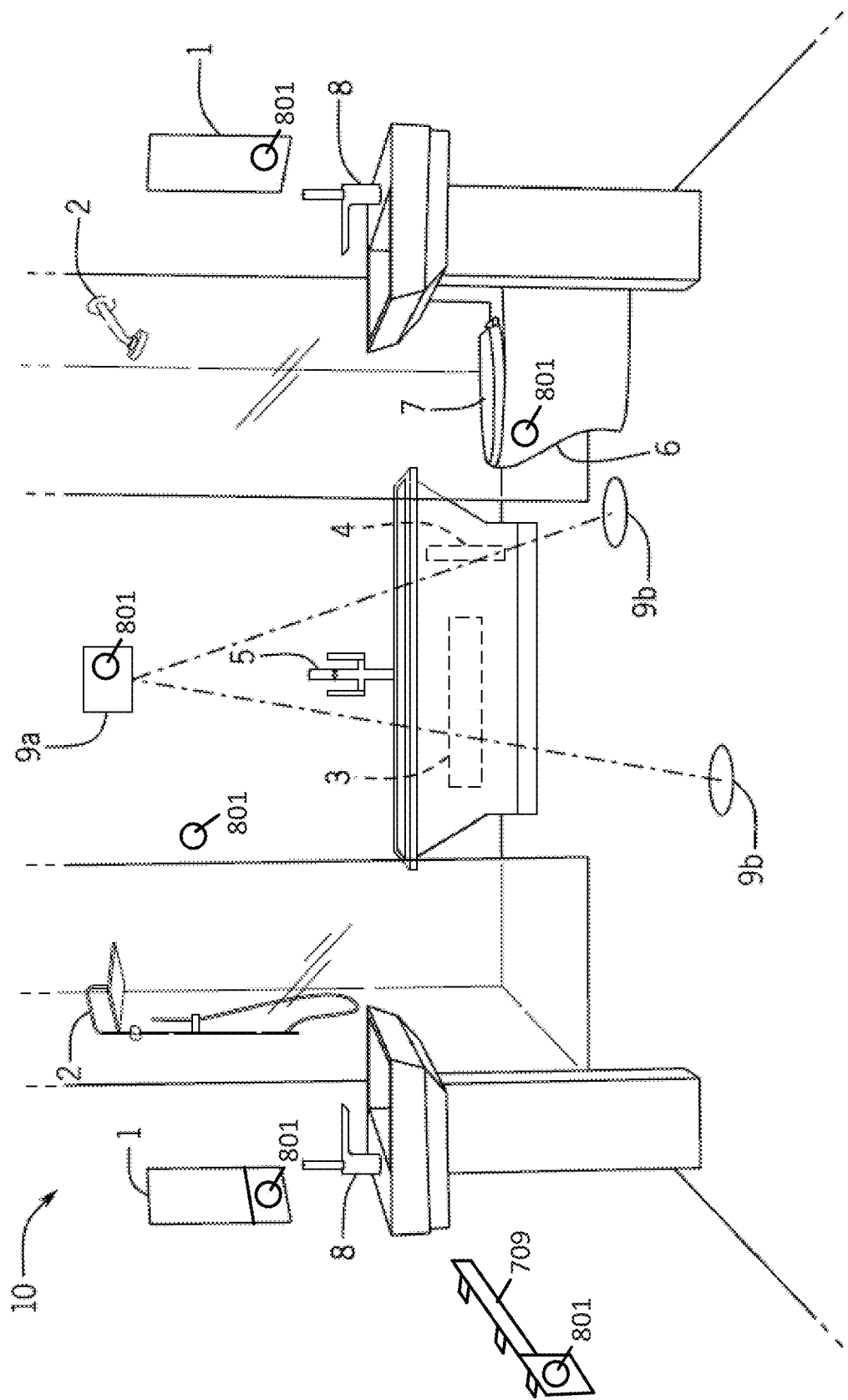
FIG. 34 illustrates a microphone array across multiple appliances.

FIG. 34 illustrates a microphone array 801 across multiple appliances. The devices may be anyone of the appliances (e.g., intelligent bathroom devices or intelligent kitchen devices) described herein. Each, some, or all of the appliances may include one or more microphones 801. Additional, different or fewer components may be included.

The array of microphones 801 are configured to receive voice inputs from one or more users for the operation of the artificial intelligence device 800 or other devices. In some smart speaker configurations, the microphones may be "always listening" for voice commands. The term always listening means that the microphones are powered and can detect voice commands at any time. The artificial intelligence device 800 may be powered only by battery, or in some configurations or docking arrangements, may be powered only by battery. With microphones that are always listening, battery storage may become problematic because power is always being consumed. The following embodiments provide techniques for the artificial intelligence device 800 that reduce battery consumption and improve the duration between charges for a battery operated artificial intelligence device 800. The artificial intelligence device 800 may be docked or associated with a first appliance, and the artificial intelligence device 800 may be woken up (mode change) by sensor data from the operation of a second appliance and/or detected by the second appliance.

The artificial intelligence device 800 may include a communication interface 806 that is configured to receive sensor data from an external appliance. The external appliance may be any of the appliances (e.g., intelligent bathroom device, intelligent kitchen devices, or host appliances) described herein. The external appliance may include a sensor 805, or be associated with the sensor 805. The sensor data describes an environment of the artificial intelligence device 800. The sensor data describes one or more events, users, or activity in the environment of the artificial intelligence device 800 that indicates the likelihood that the artificial intelligence device 800 will soon receive voice commands.

Examples of the sensor 805 include a flow sensor, an inertial sensor, a humidity, a pressure sensor, a light sensor, a proximity sensor, or a gesture sensor.

The flow sensor may detect a water flow in the external appliance. The flow sensor may measure water flowing through a pipe using a pressure sensor, ultrasonic sensor or light sensor. The light sensor may measure the quantity of water that passes a light beam. The ultrasonic sensor generates an ultrasonic wave that travels through the flow of water and is received at a received. Based on the received ultrasonic wave the volume and/or speed of the flow of water is detected. Alternatively, the flow sensor may determine whether a flow of water in the external appliance is on or off, which may be tied to a lever or a valve that opens the flow of water.

The external appliance with the flow sensor may be a water consuming device such as the programmable (automated) shower 2, the bathtub level device including the drain 4 and faucet 5, the intelligent (automated) toilet 6, the sink faucet (automated sink) 8, the kitchen appliance 11, and the water system 12. Other water consuming devices are possible.

The humidity sensor may detect humidity in the vicinity of the artificial intelligence device 800. For a bathroom, an increase in humidity indicates that the shower or another water consuming device is in operation and indicates user activity in proximity to the voice controlled device.

The pressure sensor may be incorporated in the automated toilet 6 or toilet seat 7. The pressure sensor generates sensor data that indicates whether pressure from the user (e.g., seated at the toilet) has been received. The presence of the user indicates that the bathroom is in use and indicates user activity in proximity to the voice controlled device. Similar pressure sensors may be incorporated into flooring or tiles (e.g., versatile tile including lights, speakers, sensors, and/or heaters implemented as flooring). Other pressure sensors may be used to measure water flow.

The light sensor may be incorporated into the intelligent mirror (mirror assembly) 1, the programmable (automated) shower 2, the bathtub sensory device 3, the bathtub level device including the drain 4 and faucet 5, the intelligent (automated) toilet 6, the toilet (automated) seat 7, the sink faucet (automated sink) 8, or the light source 9a and light guides 9b. The change in light in the bathroom indicates that the bathroom is in use and indicates user activity in proximity to the voice controlled device.

The inertial sensor may include a gyroscope, an accelerometer, or an impact sensor. The inertial sensor may be included in the artificial intelligence device 800. When the artificial intelligence device 800 is moved, bumped, turned, or otherwise experiences motion. The output of the inertial sensor changes. The controller 804 is configured to monitor the output of the inertial sensor to detect the change, or compare the value of the output of the inertial sensor to a threshold. When the output of the inertial sensor changes or exceeds the threshold, the controller 804 determines that a user is present or the bathroom is in use.

Other sensors may directly measure the movement or presence of a user in the bathroom. A proximity sensor may detect a presence of use in a predetermined distance or within a predetermined distance range. The proximity sensor may include a microwave or radar sensor. Another specific type of proximity sensor is a gesture sensor that measures movements of the user. The controller 804 may identify a gesture from a predetermined said of gestures based on the movement of the user. The presence of the user, or a specific gesture from the user, may indicate that the bathroom is in use and indicates user activity in proximity to the voice controlled device. The proximity sensors may be included in any of the intelligent bathroom devices or appliances described herein.

Rather than sensor 805, one of the microphones 801 may detect a sound characteristic of the water consuming appliances such as a water faucet, a toilet, or a shower. The controller 804 may activate more microphone 801 in response to the sound characteristic.

The controller 804 may select a mode in response to the sensor data. The modes may be defined on the operation of the microphones 801. The controller 804 is configured to operate a first subset of the microphones 801, or no microphones, in response sensor data describing one type of event and operate a second subset of the microphones 801 in response to sensor data describing another type of event. The first type of event may be the absence of a user in the proximity to the artificial intelligence device 800. The first type of event may trigger a dormant mode. The second type of event may be the presence of a user in the proximity to the artificial intelligence device 800. The second type of event may trigger a listening mode.

When the microphones 801 are in the same device such as artificial intelligence device 800, as shown in FIG. 33, the first subset of microphones 801 is at least one microphone in the device and the second subset of microphones 801 is a number of microphones greater than the first subset of microphones. When the microphones 801 are distributed across multiple appliances, as shown in FIG. 34, the first subset of microphones 801 may be zero microphones for a particular device, but across the system is one or more microphones such that at least one microphone in the setting (e.g., room or bathroom) is always listening in the dormant mode. In the listening mode, the second subset of microphones may include all microphones 801 across all devices in the setting, or multiple microphones in the room.

The first type of event may be detected by sensor 805 (e.g., a flow sensor, a humidity, a pressure sensor, a light sensor, a proximity sensor, or a gesture sensor) has not detected the presence of a user within a predetermined amount of time. Examples for the predetermined amount of time may include 2 minutes, 10 minutes, or 30 minutes. The second type of event may be detected by sensor 805 when the presence of a user has been detected within the predetermined amount of time.

More microphones (e.g., all microphones) all powered when the second type of event has been detected by the sensor 805. Fewer microphones (e.g., 20% of microphones, only 1 microphone, only 2 microphones, or another quantity of microphones) that is less than all microphones all powered when the first type of event has been detected by the sensor 805.

In addition or in the alternative to microphones, the controller 804 may select a full power mode or a low power mode for operation of the artificial intelligence device 800 in response to the sensor data. The controller 204 may select a low power mode for the voice controlled device in response to the first type of sensor data and the controller selects a full power mode for the voice controlled device in response to the second type of sensor data. In the low power mode, in addition to selected microphones, the artificial intelligence device 800 may deactivate the speaker and/or wireless communication.

Figure 35:
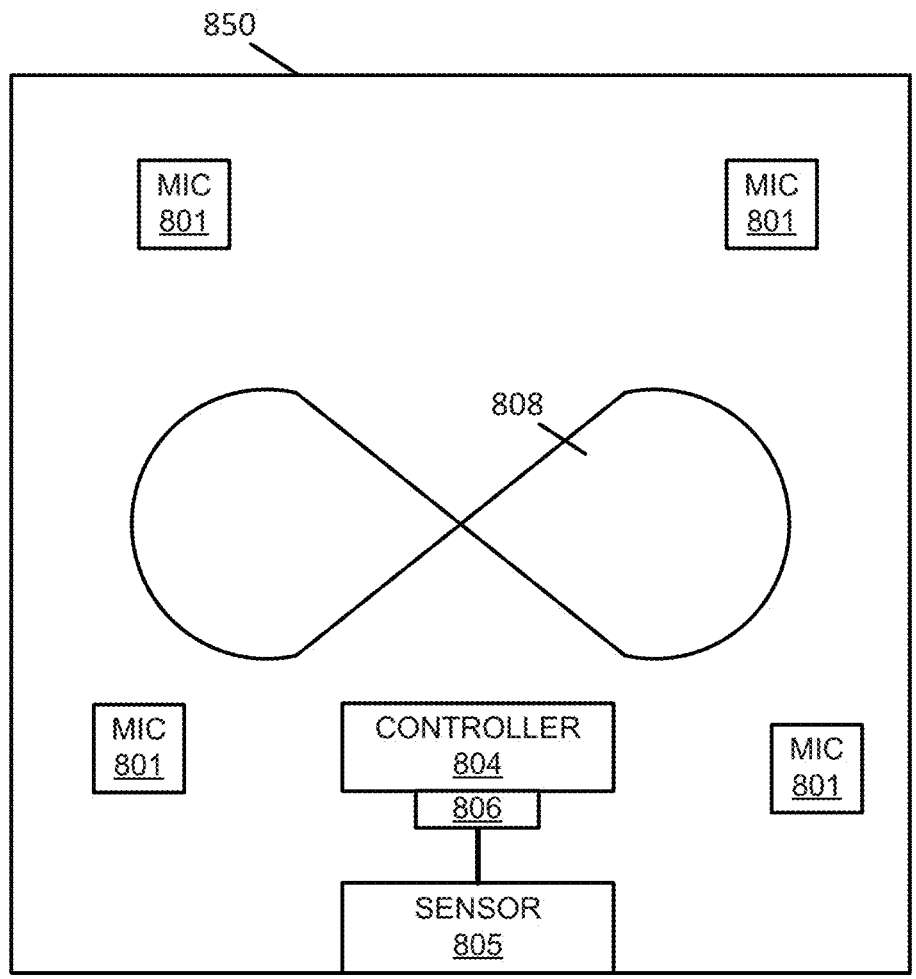
FIG. 35 illustrates a fan including a microphone array.

FIG. 35 illustrates another example of the artificial intelligence device 800 as a fan assembly 850, including a fan 808 in addition to the microphone array 801, the controller 804, the communication interface 806, and the sensor 805. The fan assembly 850 may also include a heater or a light, which may be steerable as a light guide. Additional, different, or fewer components may be included.

The sensor 805 of the fan assembly 850 may collect sensor data on the quality of air in the bathroom. The sensor 805 may detect oxygen levels or other chemical levels in the air. The sensor 805 may detect odors. The sensor 805 may detect volatile organic compounds (VOCs) or other carbon based (organic) chemicals (compounds) that are indicative of odor.

The sensor 805 of the fan may include any of the motion detectors or gesture sensors described herein to detect motion in proximity of any of the appliances of the bathroom. The sensor 805 of the fan may include a humidity sensor that detects the amount of water in the air. The microphone 801 in the fan assembly 850 may collect data indicative of sounds in the room. The sounds detected by the centrally located fan assembly 850 may include voice commands for any of the other intelligent bathroom devices.

The controller 804 may select a mode for the fan assembly 850 in response to the sensor data. In a power saving mode, the controller 804 is configured to operate a first subset of the microphones 801 in response to the sensor data indicating that no user is present in the bathroom. In a normal mode, the controller 804 is configured to operate a second subset of the microphones 801 in response to sensor data describing that a user is present in the bathroom or has been present for a predetermined amount of time.

Figure 36:
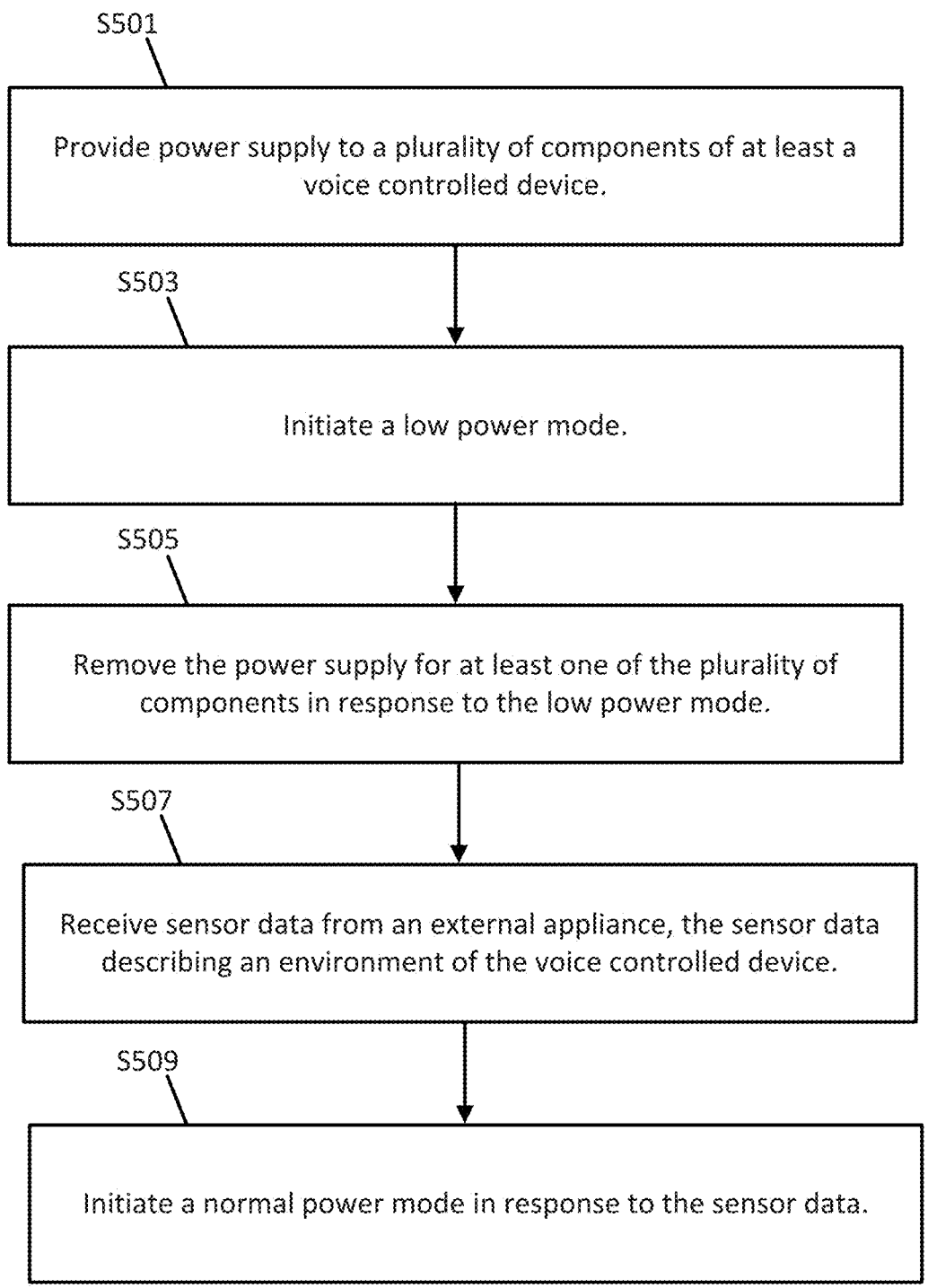
FIG. 36 illustrates a flow chart for operation of the microphone array.

FIG. 36 illustrates a flow chart for operation of the microphone array. The acts of the flow chart may be performed by controller 804 or another component. Acts may be repeated. Fewer or additional acts may be included.

At act S501, the controller 804 provides power supply to components of one or more bathroom devices and/or of one or multiple voice controlled devices. The bathroom devices may be additional devices in the vicinity of the voice controlled device. The power supply may be provided by maintaining closed switches or other circuit elements in circuit paths including each of the components. The components may include microphones 801. Other examples for the components include speakers, sensors, or lights. Any combination may be included.

At act S503, the controller 804 initiates a low power mode. The low power mode may be applied to the voice controlled device or to at least one additional devices in the vicinity of the voice controlled device. The lower power mode may be initiated in response to a timer. When a predetermined time has elapsed according to the timer, the lower power mode is initiated.

At act S505, the power supply is removed for at least one of the components in response to the low power mode. For additional devices, the power supply may be removed for all components, all microphones, or the entire device. For the individual voice controlled device, the controller 804 may remove the power supply for one or more components by opening switches or other circuit elements in circuit paths including each of the components. For the low power mode, the power supply may be removed from a specific set of components. The specific set of components may be designated as non-vital components. The specific set of components may be all components except a single microphone and supporting circuitry. The specific set of components may be the controller 804 and a small number of microphones 801. In the case of additional devices At act S507, the controller 804 receives sensor data from an external appliance, the sensor data describing an environment of the voice controlled device. The sensor data may include any of the examples described herein. In one example, the external appliance is a toilet seat and the sensor data are pressure data indicative of pressure on the toilet seat. In another example, the external device is a water consuming device and the sensor indicates a water flow of the water consuming device. In another example, the external device is a water faucet, a toilet, or a shower, and the sensor data includes a sound characteristic for water of the water faucet, the toilet, or the shower. In another example, the external device is a fan and the sensor data include a sound characteristic, an air characteristic, a humidity characteristic, or a light characteristic. In another example, the external device is any appliance and the sensor data are generated by a proximity sensor describing a user in proximity to the appliance.

At act S509, the controller 804 initiates a normal power mode in response to the sensor data. The normal mode provides power supply to the components. To initiate the normal power mode, the controller 804 closes switches or changes the state of other circuit elements in circuit paths including each of the components.

Remote Charging

Figure 37:
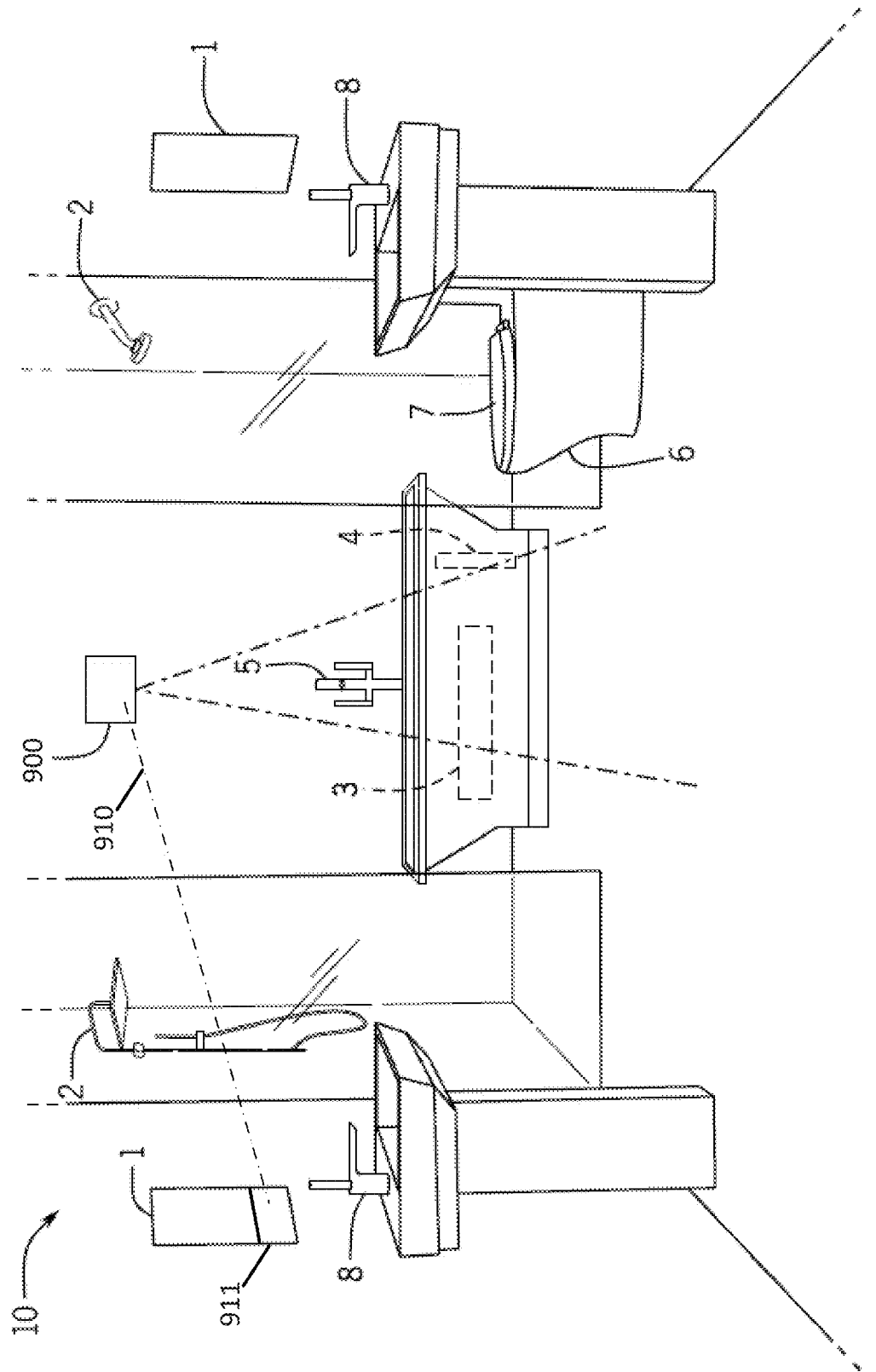
FIG. 37 illustrates a remote charging and detection system.

FIG. 37 illustrates a remote charging and detection system 900 for the bathroom setting 10 that includes multiple appliances or intelligent bathroom devices that may be connected through at least one home hub communication device. The remote charging and detection system 900 may combined with the fan assembly 850 into a single device. The intelligent bathroom devices may include one or more of an intelligent mirror 1, a programmable shower 2, a bathtub sensory device 3, a bathtub level device including a drain 4 and faucet 5, an intelligent toilet 6, a toilet seat 7, a sink faucet 8, and light guides described herein.

The remote charging and detection system 900 generates one or more charging beams 910 that are configured to scan the bathroom setting 10 to identify one or more intelligent bathroom devices. One charging beam or multiple charging beams may be used. The charging beams 910 may scan along a regular (e.g., grid) pattern in the room, or a random pattern in the room, to identify intelligent bathroom devices in the path of the scan. In one example, an intelligent bathroom device is identified when the charging beam 910 meets a charging receptor. An example charging receptor 911 for the mirror 1 is illustrated. Any of the appliances may include a charging receptor.

Once the charging receptor is found the charging beam 910 may remain in contact with the charging receptor for a duration selected by the remote charging and detection system 900. The duration may be a predetermined amount of time. The duration may be an amount of time to fully charge a batter of the intelligent bathroom device or charge the battery of the intelligent bathroom device above a threshold level. The battery level of the intelligent bathroom device may be communicated to the remote charging and detection system 900 directly or through one of the home hub communication devices described herein. The charging beam 910 may charge the battery through radio frequency energy that is collected by the intelligent bathroom device. The charging beam 910 may charge the battery through a laser beam or other light beam that is collected by a photovoltaic sensor.

Additional Hardware Architecture

Processor 300 may be a general purpose or specific purpose processor, an application specific integrated circuit (ASIC), one or more programmable logic controllers (PLCs), one or more field programmable gate arrays (FPGAs), a group of processing components, or other suitable processing components. Processor 300 is configured to execute computer code or instructions stored in memory 352 or received from other computer readable media (e.g., embedded flash memory, local hard disk storage, local ROM, network storage, a remote server, etc.). The processor 300 may be a single device or combinations of devices, such as associated with a network, distributed processing, or cloud computing.

Memory 352 may include one or more devices (e.g., memory units, memory devices, storage devices, etc.) for storing data and/or computer code for completing and/or facilitating the various processes described in the present disclosure. Memory 352 may include random access memory (RAM), read-only memory (ROM), hard drive storage, temporary storage, non-volatile memory, flash memory, optical memory, or any other suitable memory for storing software objects and/or computer instructions. Memory 352 may include database components, object code components, script components, or any other type of information structure for supporting the various activities and information structures described in the present disclosure. Memory 352 may be communicably connected to processor 300 via a processing circuit and may include computer code for executing (e.g., by processor 300) one or more processes described herein. For example, memory 298 may include graphics, web pages, HTML files, XML files, script code, shower configuration files, or other resources for use in generating graphical user interfaces for display and/or for use in interpreting user interface inputs to make command, control, or communication decisions.

In addition to ingress ports and egress ports, the communication interface 353 may include any operable connection. An operable connection may be one in which signals, physical communications, and/or logical communications may be sent and/or received. An operable connection may include a physical interface, an electrical interface, and/or a data interface. The communication interface 353 may be connected to a network. The network may include wired networks (e.g., Ethernet), wireless networks, or combinations thereof. The wireless network may be a cellular telephone network, an 802.11, 802.16, 802.20, or WiMax network, a Bluetooth pairing of devices, or a Bluetooth mesh network. Further, the network may be a public network, such as the Internet, a private network, such as an intranet, or combinations thereof, and may utilize a variety of networking protocols now available or later developed including, but not limited to TCP/IP based networking protocols.

While the computer-readable medium (e.g., memory 352) is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored. The computer-readable medium may be non-transitory, which includes all tangible computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

What is claimed is:

1. A voice controlled device comprising:
   a plurality of microphones configured to receive voice inputs from one or more users for operation of the voice controlled device;
   a communication interface configured to receive sensor data from an external device, the sensor data describing an environment of the voice controlled device; and
   a controller configured to operate a first subset of the plurality of microphones independent of the voice inputs and in response to first sensor data and a second subset of the plurality of microphones independent of the voice inputs and in response to second sensor data.

2. The voice controlled device of claim 1, wherein the controller is configured to select a low power mode for the voice controlled device in response to the first sensor data and the controller is configured to select a full power mode for the voice controlled device in response to the second sensor data.

3. The voice controlled device of claim 1, wherein the controller is configured to operate in a dormant mode in response to the first sensor data and operates in a listening mode in response to the second sensor data.

4. The voice controlled device of claim 1, wherein the first sensor data is configured to indicate user activity in proximity to the voice controlled device.

5. The voice controlled device of claim 1, wherein the external device is a water consuming device.

6. The voice controlled device of claim 1, wherein the external device is a water faucet, a toilet, or a shower, and the sensor data includes a sound characteristic of the water faucet, the toilet, or the shower.

7. The voice controlled device of claim 1, wherein the external device is a fan and the sensor data describe humidity in a proximity of the fan.

8. The voice controlled device of claim 1, wherein the first sensor data describes a flow of water.

9. The voice controlled device of claim 1, wherein the voice controlled device is associated with a first appliance, and the first sensor data describes operation of a second appliance.

10. A system of voice controlled devices comprising:
    a plurality of microphones distributed across multiple voice controlled devices, the plurality of microphones configured to receive voice inputs from one or more users;
    a sensor configured to collect sensor data describing an environment of a voice controlled device; and
    a controller configured to operate a first subset of the plurality of microphones independent of the voice inputs and in response to a first sensor data and a second subset of the plurality of microphones independent of the voice inputs and in response to a second sensor data.

11. The system of voice controlled devices of claim 10, wherein the sensor is an accelerometer or a light sensor.

* * * * *